United States Patent
Nissink et al.

(10) Patent No.: US 10,323,028 B2
(45) Date of Patent: Jun. 18, 2019

(54) 1,3,4-THIADIAZOLE COMPOUNDS AND THEIR USE IN TREATING CANCER

(71) Applicants: AstraZeneca AB, Sodertalje (SE); Cancer Research Technology Limited, London (GB)

(72) Inventors: Johannes Wilhelmus Maria Nissink, Cambridge (GB); Maurice Raymond Verschoyle Finlay, Cambridge (GB); Mark David Charles, Cambridge (GB)

(73) Assignees: AstraZeneca AB, Sodertalje (SE); Cancer Research Technology Limited, London (GB)

( * ) Notice: Subject to any disclaimer, the term of this patent is extended or adjusted under 35 U.S.C. 154(b) by 71 days.

(21) Appl. No.: 15/363,030

(22) Filed: Nov. 29, 2016

(65) Prior Publication Data
US 2017/0152255 A1   Jun. 1, 2017

Related U.S. Application Data

(60) Provisional application No. 62/260,789, filed on Nov. 30, 2015.

(51) Int. Cl.
*C07D 417/14*    (2006.01)

(52) U.S. Cl.
CPC .................. *C07D 417/14* (2013.01)

(58) Field of Classification Search
CPC .................................................. C07D 417/14
See application file for complete search history.

(56) References Cited

U.S. PATENT DOCUMENTS 9,938,265 B2 *  4/2018  Nissink ................. C07D 417/14
10,040,788 B2 *  8/2018  Finlay ................... C07D 417/14

FOREIGN PATENT DOCUMENTS

| WO | 2013078123 A1 | 5/2013 |
| WO | 2015101957 A2 | 7/2015 |
| WO | 2015181539 A1 | 12/2015 |

* cited by examiner

Primary Examiner — Golam M Shameem

(57) ABSTRACT

A compound of Formula (I):

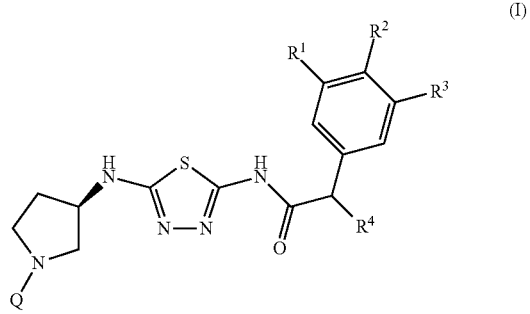

or a pharmaceutically acceptable salt thereof, where: Q can be 1,2,4-triazin-3-yl, pyridazin-3-yl, 6-methylpyridazin-3-yl, or 6-fluoropyridazin-3-yl; $R^1$ can be hydrogen, methoxy, trifluoromethoxy, oxetan-3-yl, 3-fluoroazetidin-1-yl, 3-methoxyazetidin-1-yl, or 3,3-difluoroazetidin-1-yl; $R^2$ can be hydrogen or fluoro; $R^3$ can be hydrogen or methoxy; and $R^4$ can be methoxy, ethoxy, or methoxymethyl; provided that when $R^1$ is hydrogen, methoxy or trifluoromethoxy, then $R^3$ is not hydrogen, and/or $R^4$ is methoxymethyl. The compound of formula (I) can inhibit glutaminase, e.g., GLS1.

9 Claims, No Drawings

1,3,4-THIADIAZOLE COMPOUNDS AND THEIR USE IN TREATING CANCER

CROSS-REFERENCE TO RELATED APPLICATIONS

This application claims the benefit under 35 U.S.C. § 119(e) to U.S. Application No. 62/260,789 filed on 30 Nov. 2015, the entirety of which is hereby incorporated by reference.

TECHNICAL FIELD

The specification generally relates to substituted 1,3,4-thiadiazole compounds and pharmaceutically acceptable salts thereof. These compounds act on the glutaminase 1 enzyme ("GLS1"), and the specification therefore also relates to the use of such compounds and salts thereof to treat or prevent GLS1-mediated disease, including cancer. The specification further relates to pharmaceutical compositions comprising such compounds and salts; kits comprising such compounds and salts; methods of manufacture of such compounds and salts; intermediates useful in the manufacture of such compounds and salts; and to methods of treating GLS1 mediated disease, including cancer, using such compounds and salts.

BACKGROUND

Glutamine is the most abundant plasma amino acid and is involved in many growth promoting pathways. In particular, glutamine is involved in oxidation in the TCA cycle and in maintaining cell redox equilibrium, and also provides nitrogen for nucleotide and amino acid synthesis (Curi et al., *Front. Biosci.* 2007, 12, 344-57; DeBerardinis and Cheng, *Oncogene* 2010, 313-324, each of which is incorporated by reference in its entirety). Many cancer cells rely on glutamine metabolism as a consequence of metabolic changes in the cell, including the Warburg effect where glycolytic pyruvate is converted to lactic acid rather than being used to create acetyl CoA (Koppenol et al., *Nature Reviews* 2011, 11, 325-337, which is incorporated by reference in its entirety). As a consequence of this reliance on glutamine metabolism, such cancer cells are sensitive to changes in exogenous glutamine levels. Furthermore, existing evidence suggests that glutaminolysis plays a key role in certain cancer types (Hensley et al., *J. Clin. Invest.* 2013, 123, 3678-3684, which is incorporated by reference in its entirety), and is associated with known oncogenic drivers such as Myc (Dang, *Cancer Res.* 2010, 70, 859-863, which is incorporated by reference in its entirety).

The first step of glutamine catabolism to glutamate is catalysed by glutaminase, which exists as two isoforms, GLS1 and GLS2, originally identified as being expressed in the kidney and liver, respectively. Kidney glutaminase (GLS1) is known to be more ubiquitously expressed than liver glutaminase (GLS2), and has 2 splice variants, KGA and the shorter GAC isoform, both of which are located in the mitochondria. (Elgadi et al., *Physiol. Genomics* 1999, 1, 51-62; Cassago et al., *Proc. Natl. Acad. Sci.* 2012, 109, 1092-1097, each of which is incorporated by reference in its entirety). GLS1 expression is associated with tumour growth and malignancy in a number of disease types (Wang et al., *Cancer Cell* 2010, 18, 207-219; van der Heuval et al., *Cancer Bio. Ther.* 2012, 13, 1185-1194, each of which is incorporated by reference in its entirety). Inhibitors of GLS1 are therefore expected to be useful in the treatment of cancer, as monotherapy or in combination with other anti-cancer agents.

SUMMARY

In one aspect, a compound of Formula (I):

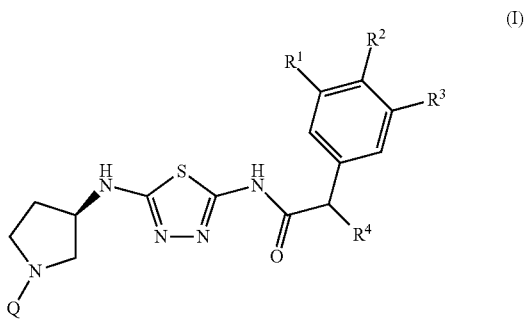

or a pharmaceutically acceptable salt thereof, where:

Q can be 1,2,4-triazin-3-yl, pyridazin-3-yl, 6-methylpyridazin-3-yl, or 6-fluoropyridazin-3-yl;

$R^1$ can be hydrogen, methoxy, trifluoromethoxy, oxetan-3-yl, 3-fluoroazetidin-1-yl, 3-methoxyazetidin-1-yl, or 3,3-difluoroazetidin-1-yl;

$R^2$ can be hydrogen or fluoro;

$R^3$ can be hydrogen or methoxy; and $R^4$ can be methoxy, ethoxy, or methoxymethyl;

provided that when $R^1$ is hydrogen, methoxy or trifluoromethoxy, then $R^3$ is not hydrogen, and/or $R^4$ is methoxymethyl.

In another aspect, a compound, or a pharmaceutically acceptable salt thereof, selected from the group consisting of:

(2S)-2-ethoxy-N-[5-[[(3R)-1-pyridazin-3-ylpyrrolidin-3-yl]amino]-1,3,4-thiadiazol-2-yl]-2-[3-(trifluoromethoxy)phenyl]acetamide;

(2R)-2-[4-fluoro-3-(trifluoromethoxy)phenyl]-2-methoxy-N-[5-[[(3R)-1-pyridazin-3-ylpyrrolidin-3-yl]amino]-1,3,4-thiadiazol-2-yl]acetamide;

(2S)-2-[4-fluoro-3-(trifluoromethoxy)phenyl]-2-methoxy-N-[5-[[(3R)-1-pyridazin-3-ylpyrrolidin-3-yl]amino]-1,3,4-thiadiazol-2-yl]acetamide; and (2S)-[3-(difluoromethoxy)phenyl]-2-ethoxy-N-[5-[[(3R)-1-pyridazin-3-ylpyrrolidin-3-yl]amino]-1,3,4-thiadiazol-2-yl]acetamide.

In another aspect, a pharmaceutical composition includes a compound as described above, or a pharmaceutically acceptable salt thereof, and at least one pharmaceutically acceptable diluent or carrier.

In another aspect, a compound as described above, or a pharmaceutically acceptable salt thereof, for use in therapy.

In another aspect, a compound as described above, or a pharmaceutically acceptable salt thereof, for use in the treatment of cancer.

In another aspect, use of a compound as described above, or a pharmaceutically acceptable salt thereof, for the manufacture of a medicament for the treatment of cancer.

In another aspect, a method for treating cancer in a warm blooded animal in need of such treatment, includes administering to the warm-blooded animal a therapeutically effective amount of a compound as described above, or a pharmaceutically acceptable salt thereof.

Other aspects will be apparent from the specification and the claims.

DETAILED DESCRIPTION

Many embodiments are detailed throughout the specification and will be apparent to a reader skilled in the art. The invention is not to be interpreted as being limited to any particular embodiment(s) thereof.

A compound of Formula (I) is provided:

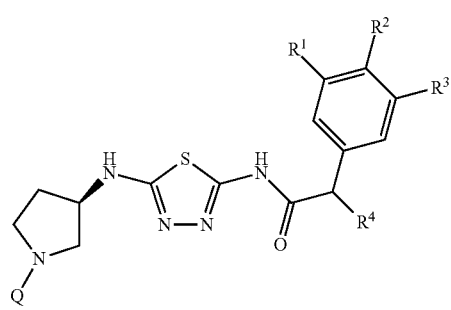

(I)

or a pharmaceutically acceptable salt thereof, where:

Q can be 1,2,4-triazin-3-yl, pyridazin-3-yl, 6-methylpyridazin-3-yl, or 6-fluoropyridazin-3-yl;

$R^1$ can be hydrogen, methoxy, trifluoromethoxy, oxetan-3-yl, 3-fluoroazetidin-1-yl; 3-methoxyazetidin-1-yl, or 3,3-difluoroazetidin-1-yl;

$R^2$ can be hydrogen or fluoro;

$R^3$ can be hydrogen or methoxy; and $R^4$ can be methoxy, ethoxy, methoxymethyl, or ethoxymethyl;

provided that when $R^1$ is hydrogen, methoxy or trifluoromethoxy, then $R^3$ is not hydrogen, and/or $R^4$ is methoxymethyl.

1,2,4-triazin-3-yl, pyridazin-3-yl, 6-methylpyridazin-3-yl, and 6-fluoropyridazin-3-yl rings have the following structures:

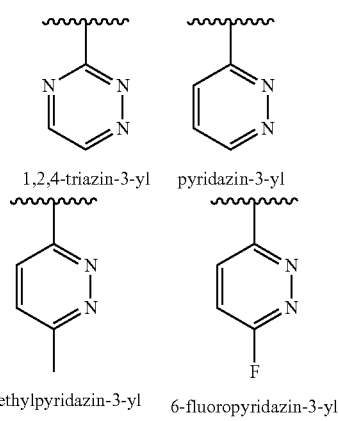

Oxetan-3-yl, 3-fluoroazetidin-1-yl; 3-methoxyazetidin-1-yl, and 3,3-difluoroazetidin-1-yl rings have the following structures:

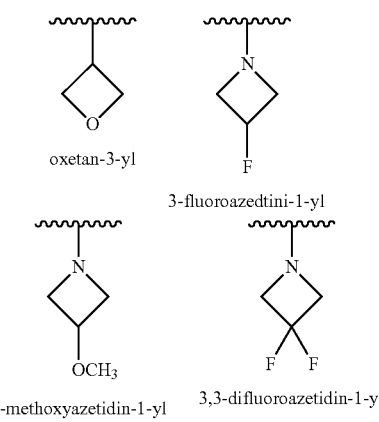

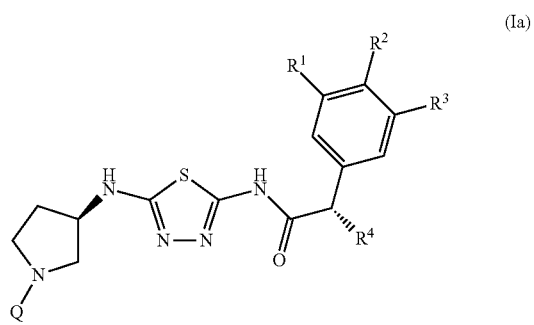

In some embodiments, the compound of Formula (I) has the following Formula (Ia):

(Ia)

wherein Q, $R^1$, $R^2$, $R^3$, and $R^4$ as defined as above.

A compound, or a pharmaceutically acceptable salt thereof, selected from the group consisting of:

(2S)-2-ethoxy-N-[5-[[(3R)-1-pyridazin-3-ylpyrrolidin-3-yl]amino]-1,3,4-thiadiazol-2-yl]-2-[3-(trifluoromethoxy)phenyl]acetamide;

(2R)-2-[4-fluoro-3-(trifluoromethoxy)phenyl]-2-methoxy-N-[5-[[(3R)-1-pyridazin-3-ylpyrrolidin-3-yl]amino]-1,3,4-thiadiazol-2-yl]acetamide;

(2S)-2-[4-fluoro-3-(trifluoromethoxy)phenyl]-2-methoxy-N-[5-[[(3R)-1-pyridazin-3-ylpyrrolidin-3-yl]amino]-1,3,4-thiadiazol-2-yl]acetamide; and (2S)-[3-(difluoromethoxy)phenyl]-2-ethoxy-N-[5-[[(3R)-1-pyridazin-3-ylpyrrolidin-3-yl]amino]-1,3,4-thiadiazol-2-yl]acetamide;

is also provided.

The term "pharmaceutically acceptable" is used to specify that an object (for example a salt, dosage form, diluent or carrier) is suitable for use in patients. An example list of pharmaceutically acceptable salts can be found in the *Handbook of Pharmaceutical Salts: Properties, Selection and Use*, P. H. Stahl and C. G. Wermuth, editors, Weinheim/Zürich: Wiley-VCH/VHCA, 2002, which is incorporated by reference in its entirety. A suitable pharmaceutically acceptable salt of a compound of Formula (I) is, for example, an acid-addition salt. An acid addition salt of a compound of Formula (I) may be formed by bringing the compound into contact with a suitable inorganic or organic acid under conditions known to the skilled person. An acid addition salt may be formed using, for example, an inorganic acid such as hydrochloric acid, hydrobromic acid, sulphuric acid, and phosphoric acid. An acid addition salt may also be formed using, for example, an organic acid such as trifluoroacetic acid, methanesulfonic acid, or benzenesulfonic acid.

Therefore, in one embodiment there is provided a compound of Formula (I) or a pharmaceutically acceptable salt thereof, where the pharmaceutically acceptable salt is a hydrochloric acid, hydrobromic acid, sulphuric acid, phosphoric acid, trifluoroacetic acid, methanesulfonic acid, or benzenesulfonic acid salt.

In one embodiment there is provided a compound of Formula (I) or a pharmaceutically acceptable salt thereof, where the pharmaceutically acceptable salt is a hydrochloric acid or hydrobromic acid salt.

A further suitable pharmaceutically acceptable salt of a compound of Formula (I) is a base-addition salt. A base addition salt of a compound of Formula (I) may be formed by bringing the compound into contact with a suitable inorganic or organic base under conditions known to the skilled person. A base addition salt may for example be formed using, for example, an inorganic base such as an alkali metal hydroxide (such as sodium, potassium, or lithium hydroxide) or an alkaline earth metal hydroxide (such as calcium hydroxide or magnesium hydroxide). A base addition salt may also be formed using, for example, an organic base such as methylamine, dimethylamine, trimethylamine, piperidine, morpholine, or tris-(2-hydroxyethyl) amine.

Therefore, in one embodiment there is provided a compound of Formula (I) or a pharmaceutically acceptable salt thereof, where the pharmaceutically acceptable salt is a sodium hydroxide, potassium hydroxide, lithium hydroxide, calcium hydroxide, magnesium hydroxide, methylamine, dimethylamine, trimethylamine, piperidine, morpholine, or tris-(2-hydroxyethyl)amine salt.

In one embodiment there is provided a compound of Formula (I) or a pharmaceutically acceptable salt thereof, where the pharmaceutically acceptable salt is a hydrochloric acid, hydrobromic acid, sulphuric acid, phosphoric acid, trifluoroacetic acid, methanesulfonic acid, benzenesulfonic acid, sodium hydroxide, potassium hydroxide, lithium hydroxide, calcium hydroxide, magnesium hydroxide, methylamine, dimethylamine, trimethylamine, piperidine, morpholine, or tris-(2-hydroxyethyl)amine salt.

A further embodiment provides any of the embodiments defined herein (for example the embodiment of claim 1) with the proviso that one or more specific Examples (for instance one, two or three specific Examples, or alternatively one specific Example) selected from the group consisting of Examples 1(a), 1(b), 2(a), 2(b), 3(a), 3(b), 4(a), 4(b), 5(a), 5(b), 6(a), 6(b), 7(a), 7(b), 8(a), 8(b), 9(a), 9(b), 10(a), 10(b), 11(a), 11(b), 12(a), 12(b), 13(a), 13(b), 14(a), 14(b), 15(a), 15(b), 16(a), 16(b), 17(a), 17(b), 18(a), 18(b), 19(a), 19(b), 20(a), 20(b), 21(a), 21(b), 22(a), 22(b), 23, 24, 25, 26, 27, 28, 29, 30, 31, 32, 33, 34, 35, 36, 37, 38, 39, 40, 41, 42, 43, 44, 45(a), 45(b), 46(a), 46(b), 47(a), 47(b), 48(a), 48(b), 49(a), 49(b), 50(a), 50(b), 51(a), 51(b), 52(a), 52(b), 53(a), 53(b), 54(a), and 54(b) is individually disclaimed.

Some values of variable groups in Formula (I) are as follows. Such values may be used in combination with any of the definitions, claims (for example claim 1), or embodiments defined herein to provide further embodiments.

$R^1$ can be methoxy or trifluoromethoxy.
$R^1$ can be methoxy and $R^3$ can be methoxy.
$R^1$ can be oxetan-3-yl, 3-fluoroazetidin-1-yl, 3-methoxyazetidin-1-yl, or 3,3-difluoroazetidin-1-yl.
$R^1$ can be oxetan-3-yl.
$R^1$ can be 3-fluoroazetidin-1-yl.
$R^1$ can be 3-methoxyazetidin-1-yl.
$R^1$ can be 3,3-difluoroazetidin-1-yl.
$R^2$ can be H.
$R^2$ can be fluoro.
$R^3$ can be methoxy.
$R^4$ can be methoxy or ethoxy.
$R^4$ can be methoxy.
$R^4$ can be methoxymethyl.
Q can be 1,2,4-triazin-3-yl or pyridazin-3-yl.
Q can be 1,2,4-triazin-3-yl.
Q can be pyridazin-3-yl.
Q can be 6-methylpyridazin-3-yl or 6-fluoropyridazin-3-yl.
Q can be 6-methylpyridazin-3-yl.
Q can be 6-fluoropyridazin-3-yl.

In one embodiment there is provided a compound of Formula (I), or a pharmaceutically acceptable salt thereof, where:
Q is 1,2,4-triazin-3-yl, pyridazin-3-yl, 6-methylpyridazin-3-yl, or 6-fluoropyridazin-3-yl;
$R^1$ is methoxy, trifluoromethoxy, oxetan-3-yl, 3-fluoroazetidin-1-yl, 3-methoxyazetidin-1-yl, or 3,3-difluoroazetidin-1-yl;
$R^2$ is hydrogen or fluoro;
$R^3$ is hydrogen or methoxy; and
$R^4$ is methoxy, ethoxy, or methoxymethyl;
provided that when $R^1$ is methoxy or trifluoromethoxy, then $R^3$ is not hydrogen, and/or $R^4$ is methoxymethyl.

In one embodiment there is provided a compound of Formula (I), or a pharmaceutically acceptable salt thereof, where:
Q is pyridazin-3-yl; and
$R^1$ is methoxy or trifluoromethoxy.

In one embodiment there is provided a compound of Formula (I), or a pharmaceutically acceptable salt thereof, where:
Q is pyridazin-3-yl; and
$R^1$ is oxetan-3-yl, 3-fluoroazetidin-1-yl, 3-methoxyazetidin-1-yl, or 3,3-difluoroazetidin-1-yl.

In one embodiment there is provided a compound of Formula (I), or a pharmaceutically acceptable salt thereof, where:
Q is pyridazin-3-yl;
$R^1$ is methoxy; and
$R^3$ is methoxy.

In one embodiment there is provided a compound of Formula (I), or a pharmaceutically acceptable salt thereof, where:
Q is 6-methylpyridazin-3-yl or 6-fluoropyridazin-3-yl; and
$R^1$ is 3-fluoroazetidin-1-yl, 3-methoxyazetidin-1-yl, or 3,3-difluoroazetidin-1-yl.

In one embodiment there is provided a compound of Formula (I), or a pharmaceutically acceptable salt thereof, where the compound is selected from the group consisting of:
(2S)-2-[3-(3-fluoroazetidin-1-yl)phenyl]-2-methoxy-N-[5-[[(3R)-1-pyridazin-3-ylpyrrolidin-3-yl]amino]-1,3,4-thiadiazol-2-yl]acetamide;
(2S)-2-(3,5-dimethoxyphenyl)-2-methoxy-N-[5-[[(3R)-1-(6-methylpyridazin-3-yl)pyrrolidin-3-yl]amino]-1,3,4-thiadiazol-2-yl]acetamide;
(2S)-2-[3-(3,3-difluoroazetidin-1-yl)phenyl]-2-methoxy-N-[5-[[(3R)-1-pyridazin-3-ylpyrrolidin-3-yl]amino]-1,3,4-thiadiazol-2-yl]acetamide;

(2S)-2-methoxy-2-[3-(3-methoxyazetidin-1-yl)phenyl]-N-[5-[[(3R)-1-pyridazin-3-ylpyrrolidin-3-yl]amino]-1,3,4-thiadiazol-2-yl]acetamide;
(2S)-2-(3,5-dimethoxyphenyl)-2-methoxy-N-[5-[[(3R)-1-(1,2,4-triazin-3-yl)pyrrolidin-3-yl]amino]-1,3,4-thiadiazol-2-yl]acetamide;
(2R)-3-methoxy-2-(3-methoxyphenyl)-N-[5-[[(3R)-1-pyridazin-3-ylpyrrolidin-3-yl]amino]-1,3,4-thiadiazol-2-yl]propanamide;
(2S)-2-(3,5-dimethoxyphenyl)-2-ethoxy-N-[5-[[(3R)-1-pyridazin-3-ylpyrrolidin-3-yl]amino]-1,3,4-thiadiazol-2-yl]acetamide;
(2S)-2-[4-fluoro-3-(3-methoxyazetidin-1-yl)phenyl]-2-methoxy-N-[5-[(3R)-3-(pyridazin-3-ylamino)pyrrolidin-1-yl]-1,3,4-thiadiazol-2-yl]acetamide;
(2S)—N-[5-[[(3R)-1-(6-fluoropyridazin-3-yl)pyrrolidin-3-yl]amino]-1,3,4-thiadiazol-2-yl]-2-methoxy-2-[3-(3-methoxyazetidin-1-yl)phenyl]acetamide;
(2S)-2-[3-(3-fluoroazetidin-1-yl)-5-methoxy-phenyl]-2-methoxy-N-[5-[[(3R)-1-pyridazin-3-ylpyrrolidin-3-yl]amino]-1,3,4-thiadiazol-2-yl]acetamide;
(2S)-2-methoxy-2-[3-methoxy-5-(trifluoromethoxy)phenyl]-N-[5-[[(3R)-1-pyridazin-3-ylpyrrolidin-3-yl]amino]-1,3,4-thiadiazol-2-yl]acetamide;
(2R)-2-methoxy-2-[3-methoxy-5-(trifluoromethoxy)phenyl]-N-[5-[[(3R)-1-pyridazin-3-ylpyrrolidin-3-yl]amino]-1,3,4-thiadiazol-2-yl]acetamide;
(2S)-2-(4-fluorophenyl)-2-methoxy-N-[5-[[(3R)-1-(5-methylpyridazin-3-yl)pyrrolidin-3-yl]amino]-1,3,4-thiadiazol-2-yl]acetamide;
(2S)-2-methoxy-2-[3-(3-methoxyazetidin-1-yl)phenyl]-N-[5-[[(3R)-1-(6-methylpyridazin-3-yl)pyrrolidin-3-yl]amino]-1,3,4-thiadiazol-2-yl]acetamide;
(2S)-2-[4-fluoro-3-(3-fluoroazetidin-1-yl)phenyl]-2-methoxy-N-[5-[[(3R)-1-pyridazin-3-ylpyrrolidin-3-yl]amino]-1,3,4-thiadiazol-2-yl]acetamide;
(2S)-2-[3-(3,3-difluoroazetidin-1-yl)phenyl]-2-methoxy-N-[5-[[(3R)-1-(1,2,4-triazin-3-yl)pyrrolidin-3-yl]amino]-1,3,4-thiadiazol-2-yl]acetamide;
(2S)-2-methoxy-2-[3-(3-methoxyazetidin-1-yl)phenyl]-N-[5-[[(3R)-1-(1,2,4-triazin-3-yl)pyrrolidin-3-yl]amino]-1,3,4-thiadiazol-2-yl]acetamide;
(2S)-2-[3-(3-fluoroazetidin-1-yl)phenyl]-2-methoxy-N-[5-[[(3R)-1-(1,2,4-triazin-3-yl)pyrrolidin-3-yl]amino]-1,3,4-thiadiazol-2-yl]acetamide; and
(2S)-2-methoxy-2-[3-(oxetan-3-yl)phenyl]-N-[5-[[(3R)-1-pyridazin-3-ylpyrrolidin-3-yl]amino]-1,3,4-thiadiazol-2-yl]acetamide.

In one embodiment there is provided a compound of Formula (I), or a pharmaceutically acceptable salt thereof, where the compound is selected from the group consisting of:
(2S)-2-ethoxy-N-[5-[[(3R)-1-pyridazin-3-ylpyrrolidin-3-yl]amino]-1,3,4-thiadiazol-2-yl]-2-[3-(trifluoromethoxy)phenyl]acetamide;
(2R)-2-[4-fluoro-3-(trifluoromethoxy)phenyl]-2-methoxy-N-[5-[[(3R)-1-pyridazin-3-ylpyrrolidin-3-yl]amino]-1,3,4-thiadiazol-2-yl]acetamide;
(2S)-2-[4-fluoro-3-(trifluoromethoxy)phenyl]-2-methoxy-N-[5-[[(3R)-1-pyridazin-3-ylpyrrolidin-3-yl]amino]-1,3,4-thiadiazol-2-yl]acetamide; and
(2S)-2-[3-(difluoromethoxy)phenyl]-2-ethoxy-N-[5-[[(3R)-1-pyridazin-3-ylpyrrolidin-3-yl]amino]-1,3,4-thiadiazol-2-yl]acetamide.

Compounds and salts described in this specification may exist in solvated forms and unsolvated forms. For example, a solvated form may be a hydrated form, such as a hemi-hydrate, a mono-hydrate, a di-hydrate, a tri-hydrate or an alternative quantity thereof. The present invention encompasses all such solvated and unsolvated forms of compounds of Formula (I).

Atoms of the compounds and salts described in this specification may exist in different isotopic forms. The present invention encompasses all isotopic forms of compounds of Formula (I) including an $^{11}C$ or $^{13}C$ carbon and $^{1}H$, $^{2}H$ (deuterium) or $^{3}H$ (tritium)hydrogen.

Compounds and salts described in this specification may exist as a mixture of tautomers. "Tautomers" are structural isomers that exist in equilibrium resulting from the migration of a hydrogen atom. The present invention includes all tautomers of compounds of Formula (I).

Compounds of Formula (I) can be prepared in different diastereomeric forms. The present invention includes all diastereomeric forms of the compounds of Formula (I).

In one embodiment there is provided a compound of Formula (I), or a pharmaceutically acceptable salt thereof, which is a single diastereomer being in an diastereomeric excess (% de) of ≥95%, ≥98% or ≥99%. In one embodiment, the single diastereomer is present in diastereomeric excess (% de) of ≥99%.

Compounds believed to inhibit GLS1, i.e., the compounds of Formula (I), and pharmaceutically acceptable salts thereof are expected to be useful in therapy, for example in the treatment of diseases or medical conditions mediated at least in part by GLS1, including cancer.

Where "cancer" is mentioned, this includes both non-metastatic cancer and also metastatic cancer, such that treating cancer involves treatment of both primary tumours and also tumour metastases.

In one embodiment the cancer is metastatic cancer.

In one embodiment the cancer is non-metastatic cancer.

"GLS1 inhibitory activity" refers to a decrease in the activity of GLS1 as a direct or indirect response to the presence of a compound of Formula (I), or pharmaceutically acceptable salt thereof, relative to the activity of GLS1 in the absence of compound of Formula (I), or pharmaceutically acceptable salt thereof. Such a decrease in activity may be due to the direct interaction of the compound of Formula (I), or pharmaceutically acceptable salt thereof with GLS1, or due to the interaction of the compound of Formula (I), or pharmaceutically acceptable salt thereof with one or more other factors that in turn affect GLS1 activity. For example, the compound of Formula (I), or pharmaceutically acceptable salt thereof, may decrease GLS1 by directly binding to GLS1; by causing (directly or indirectly) another factor to decrease GLS1 activity; or by (directly or indirectly) decreasing the amount of GLS1 present in the cell or organism.

The term "therapy" is intended to have its normal meaning of treating a disease or correcting or compensating for the underlying pathology. The term "therapy" also includes "prophylaxis" unless there are specific indications to the contrary. The terms "therapeutic" and "therapeutically" should be interpreted in a corresponding manner.

The term "therapeutically effective amount" refers to an amount of a compound of Formula (I) as described in any of the embodiments herein which is effective to provide therapy in a subject. In the case of cancer, the therapeutically effective amount may cause any of the changes observable or measurable in a subject as described in the definition of "therapy", "treatment" and "prophylaxis" above. For example, the effective amount can reduce the number of cancer or tumor cells; reduce the overall tumor size; inhibit or stop tumor cell infiltration into peripheral organs including, for example, the soft tissue and bone; inhibit and stop tumor metastasis; inhibit and stop tumor growth; relieve to some extent one or more of the symptoms associated with the cancer; reduce morbidity and mortality; improve quality of life; or a combination of such effects. An effective amount may be an amount sufficient to decrease the symptoms of a disease responsive to inhibition of GLS1 activity. For cancer therapy, efficacy in-vivo can, for example, be measured by assessing the duration of survival, time to disease progression (TTP), the response rates (RR), duration of response, and/or quality of life. As recognized by those skilled in the art, effective amounts may vary depending on route of administration, excipient usage, and co-usage with other agents. For example, where a combination therapy is used, the amount of the compound of Formula (I) or pharmaceutically acceptable salt described in this specification and the amount of the other pharmaceutically active agent(s) are, when combined, jointly effective to treat a targeted disorder in the animal patient. In this context, the combined amounts are in a "therapeutically effective amount" if they are, when combined, sufficient to decrease the symptoms of a disease responsive to inhibition of GLS1 activity as described above. Typically, such amounts may be determined by one skilled in the art by, for example, starting with the dosage range described in this specification for the compound of Formula (I) or pharmaceutically acceptable salt thereof and an approved or otherwise published dosage range(s) of the other pharmaceutically active compound(s).

The term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease.

The term "treatment" is used synonymously with "therapy". Similarly the term "treat" can be regarded as applying therapy where "therapy" is as defined herein.

In one embodiment there is provided a pharmaceutical composition including the compound of Formula (I), or a pharmaceutically acceptable salt thereof, and at least one pharmaceutically acceptable diluent or carrier. In one embodiment, the pharmaceutical composition includes a compound of Formula (I) as a free base. In another embodiment, the pharmaceutical composition includes a a pharmaceutically acceptable salt of a compound of Formula (I).

In one embodiment there is provided a compound of Formula (I), or a pharmaceutically acceptable salt thereof, for use in therapy.

In one embodiment there is provided a compound of Formula (I), or a pharmaceutically acceptable salt thereof, for use in the treatment of cancer.

In one embodiment there is provided the use of the compound of Formula (I), or a pharmaceutically acceptable salt thereof, for the manufacture of a medicament for the treatment of cancer.

In one embodiment there is provided a compound of Formula (I), or a pharmaceutically acceptable salt thereof, for use in the treatment of a disease mediated by GLS1. In one embodiment, the disease mediated by GLS1 is cancer. In some embodiments, the cancer can be breast cancer (for example triple negative breast cancer), lung cancer (for example non-small cell lung cancer), pancreatic cancer, renal cancer, or hepatocellular cancer.

"Triple negative breast cancer" is any breast cancer that does not express, or underexpresses, the genes for the estrogen receptor, progesterone receptor and Her2/neu.

In one embodiment there is provided the use of the compound of Formula (I), or a pharmaceutically acceptable salt thereof, for the manufacture of a medicament for the treatment of a disease mediated by GLS1. In one embodiment, the disease mediated by GLS1 is cancer. In some embodiments, the cancer can be breast cancer (for example triple negative breast cancer), lung cancer (for example non-small cell lung cancer), pancreatic cancer, renal cancer, or hepatocellular cancer.

In one embodiment there is provided the use of the compound of Formula (I), or a pharmaceutically acceptable salt thereof, for the manufacture of a medicament for the treatment of cancer.

In one embodiment there is provided a method of inhibiting GLS1 which includes administering a compound of Formula (I).

In one embodiment there is provided a method for treating a disease in which inhibition of GLS1 is beneficial in a warm-blooded animal in need of such treatment, which includes administering to the warm-blooded animal a therapeutically effective amount of a compound of Formula (I), or a pharmaceutically acceptable salt thereof.

"Warm-blooded animals" include, for example, humans.

In one embodiment there is provided a method for treating cancer in a warm-blooded animal in need of such treatment, which includes administering to the warm-blooded animal a therapeutically effective amount of a compound of Formula (I), or a pharmaceutically acceptable salt thereof. In some embodiments, the cancer can be breast cancer (for example triple negative breast cancer), lung cancer (for example non-small cell lung cancer), pancreatic cancer, renal cancer, or hepatocellular cancer.

The treatment for cancer described in this specification may be applied as a sole therapy, or may involve, in addition to administration of the compound of Formula (I), conventional surgery, radiotherapy, or chemotherapy; or a combination of such additional therapies. Such conventional surgery, radiotherapy, or chemotherapy may be administered simultaneously, sequentially, or separately to treatment with the compound of Formula (I).

Therefore, in one embodiment there is provided a compound of Formula (I), or a pharmaceutically acceptable salt thereof, and at least one additional anti-tumour substance, for use in the treatment of cancer.

In one embodiment there is provided a compound of Formula (I), or a pharmaceutically acceptable salt thereof, and at least one additional anti-tumour substance for use in the simultaneous, separate or sequential treatment of cancer.

In one embodiment there is provided a compound of Formula (I), or a pharmaceutically acceptable salt thereof, for use in the treatment of cancer, where the compound of Formula (I) is administered simultaneously, separately, or sequentially with at least one additional anti-tumour substance.

In one embodiment there is provided a method of treating cancer in a warm-blooded animal who is in need of such treatment, which includes administering to the warm-blooded animal a compound of Formula (I), or a pharmaceutically acceptable salt thereof and at least one additional anti-tumour substance, wherein the amounts of the compound of Formula (I), or a pharmaceutically acceptable salt thereof, and the additional anti-tumour substance are jointly effective in producing an anti-cancer effect.

In one embodiment there is provided a method of treating cancer in a warm-blooded animal who is in need of such treatment, which includes administering to the warm-blooded animal a compound of Formula (I), or a pharmaceutically acceptable salt thereof, and simultaneously, separately or sequentially administering at least one additional anti-tumour substance to the warm-blooded animal, wherein the amounts of the compound of Formula (I), or pharmaceutically acceptable salt thereof, and the additional anti-tumour substance are jointly effective in producing an anti-cancer effect.

In any embodiment the additional anti-tumour substance is a taxane. In one embodiment the taxane is paclitaxel. In one embodiment the taxane is docetaxel.

In any embodiment the additional anti-tumour substance is a platinum therapy. In one embodiment the platinum therapy is cisplatin, oxaliplatin, or carboplatin.

According to a further embodiment there is provided a kit comprising:
- a) A compound of Formula (I), or a pharmaceutically acceptable salt thereof, in a first unit dosage form;
- b) A second anti-tumour substance in a second unit dosage form;
- c) A container for containing the first and second unit dosage forms; and, optionally,
- d) Instructions for use.

The compounds of Formula (I), and pharmaceutically acceptable salts thereof, may be administered as pharmaceutical compositions, comprising one or more pharmaceutically acceptable diluents or carriers. Accordingly, in one embodiment there is provided a pharmaceutical composition comprising a compound of Formula (I), or a pharmaceutically acceptable salt thereof, and at least one pharmaceutically acceptable diluent or carrier.

The compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular dosing), or as a suppository. The compositions may be obtained by conventional procedures using conventional pharmaceutical excipients. Thus, compositions intended for oral use may contain, for example, one or more coloring, sweetening, flavoring, and/or preservative agents.

In one embodiment there is provided a pharmaceutical composition comprising a compound of Formula (I), or a pharmaceutically acceptable salt thereof, and at least one pharmaceutically acceptable diluent or carrier, for use in therapy.

In one embodiment there is provided a pharmaceutical composition comprising a compound of Formula (I), or a pharmaceutically acceptable salt thereof, and at least one pharmaceutically acceptable diluent or carrier, for use in the treatment of cancer. In some embodiments the cancer can be breast cancer (for example triple negative breast cancer), lung cancer (for example non-small cell lung cancer), pancreatic cancer, renal cancer, or hepatocellular cancer.

The compound of Formula (I) will normally be administered to a warm-blooded animal at a unit dose within the range 5-5000 mg/m$^2$ body area of the animal, i.e., approximately 0.1-100 mg/kg, and this normally provides a therapeutically-effective dose. A unit dose form such as a tablet or capsule will usually contain, for example 1-250 mg of active ingredient. The daily dose will necessarily be varied depending upon the host treated, the particular route of administration, any therapies being co-administered, and the severity of the illness being treated. Accordingly the practitioner who is treating any particular patient may determine the optimum dosage.

EXAMPLES

The various embodiments are illustrated by the following Examples. The invention is not to be interpreted as being limited to the Examples.

During the preparation of the Examples, generally:
- a) Operations were carried out at ambient temperature, i.e. in the range of about 17 to 30° C. and under an atmosphere of an inert gas such as nitrogen unless otherwise stated;
- b) Evaporations were carried out by rotary evaporation or utilising Genevac equipment in vacuo and work-up procedures were carried out after removal of residual solids by filtration;
- c) Flash chromatography purifications were performed on an automated Isco Combiflash Companion using Grace Resolve prepacked silica columns, and (reverse phase flash) Isco Combiflash Rf using RediSep Gold C18 columns;
- d) Yields, where present, are not necessarily the maximum attainable;
- e) Structures of end-products of Formula (I) were confirmed by nuclear magnetic resonance (NMR) spectroscopy, with NMR chemical shift values measured on the delta scale. Proton magnetic resonance spectra were determined using a Bruker Avance 700 (700 MHz), Bruker Avance 500 (500 MHz), Bruker 400 (400 MHz) or Bruker 300 (300 MHz) instrument; $^{19}$F NMR were determined at 282 MHz or 376 MHz; $^{13}$C NMR were determined at 75 MHz or 100 MHz; measurements were taken at around 20-30° C. unless otherwise specified; the following abbreviations have been used: s, singlet; d, doublet; t, triplet; q, quartet; m, multiplet; dd, doublet of doublets; ddd, doublet of doublet of doublet; dt, doublet of triplets; bs, broad signal;
- f) End-products of Formula (I) were also characterised by mass spectroscopy following liquid chromatography (LCMS), using a HPLC system based on a Waters 2790/95 LC system with a 2996 PDA and a 2000 amu ZQ single quadrupole mass spectrometer. The solvents used were A=Water, B=Acetonitrile, C=50:50 acetonitrile:water 0.1% formic acid and D=50:50 acetonitrile:water 0.1% ammonium hydroxide. At a flow rate of 1.1 mL/min 5 μL of sample was injected onto a 50×2.1 5 μm Phenomenex Gemini NX column. The gradient ran from 95% A to 95% B for 4.0 mins with a constant 5% infusion of C (for acid analysis, D is used for base analysis). The flow was held at 95% B for 0.5 mins before returning to start conditions. The Data was acquired from 150 to 850 amu in both positive and negative mode on the Mass Spectrometer and 220-320 nm on the PDA. LCMS was also performed on a UPLC system utilising a Waters Acquity Binary pump with sample manager, Acquity PDA and an SQD Mass spectrometer. The solvents used were A1=0.1% formic acid (aq), B1 0.1% formic acid in acetonitrile, A2=0.1% ammonium hydroxide (aq) and B2 0.1% ammonium hydroxide in acetonitrile. At a flow rate of 1 mL/min 1 μL of sample was injected onto a 50×2.1 1.7 um Waters BEH column (at 40° C.). The gradient ran from 97% A1 to 97% B1 over 1.30 mins before being held for 0.2 min and returning to start conditions (substitute A1 and B1 for A2 and B2 for base analysis).

Data was acquired from 150-1000 amu in positive and negative ion mode on the mass spectrometer and 245-320 amu on the PDA;

g) Intermediates were not generally fully characterised and purity was assessed by thin layer chromatographic, mass spectral, HPLC and/or NMR analysis;

h) The following abbreviations have been used: h=hour(s); r.t.=room temperature (~17-30° C.); conc.=concentrated; FCC=flash column chromatography using silica; AIBN=azobisisobutyronitrile; DCM=dichloromethane; DIPEA=di-isopropyl ethylamine; DMA=N,N-dimethylacetamide; DMF=N,N-dimethylformamide; DMSO=dimethylsulfoxide; EDC=1-Ethyl-3-(3-dimethylaminopropyl)carbodiimide; Et$_2$O=diethyl ether; EtOAc=ethyl acetate; EtOH=ethanol; HATU=1-[bis(dimethylamino)methylene]-1H-1,2,3-triazolo[4,5-b]pyridinium 3-oxid hexafluorophosphate; HOBT=hydroxybenzotriazole; K$_2$CO$_3$=potassium carbonate; MeOH=methanol; MeCN=acetonitrile; MgSO$_4$=anhydrous magnesium sulphate; Na$_2$SO$_4$=anhydrous sodium sulphate; NBS=N-bromo succinimide; TFA=trifluoroacetic acid; THF=tetrahydrofuran; sat.=saturated aqueous solution.

In a number of the examples below, a diastereomeric pair of compounds is described. For example, the compounds of Example 1(a) and Example 1(b) represent a diastereomeric pair of compounds, formed as a mixture in the product of a single reaction and subsequently separated. In such examples, any assignment of stereochemistry is not absolute. By way of illustration, Examples 1(a) and 1(b) relate to the (2S,3R) and (2R,3R) diastereomers of the named compound; however, it is not intended convey that Example 1(a) is definitively assigned as the (2S,3R) diastereomer and Example 1(b) as the (2R,3R) diastereomer.

Example 1(a) and 1(b)

(2S)-2-[3-(3-Fluoroazetidin-1-yl)phenyl]-2-methoxy-N-[5-[[(3R)-1-pyridazin-3-ylpyrrolidin-3-yl]amino]-1,3,4-thiadiazol-2-yl]acetamide and (2R)-2-[3-(3-Fluoroazetidin-1-yl)phenyl]-2-methoxy-N-[5-[[(3R)-1-pyridazin-3-ylpyrrolidin-3-yl]amino]-1,3,4-thiadiazol-2-yl]acetamide

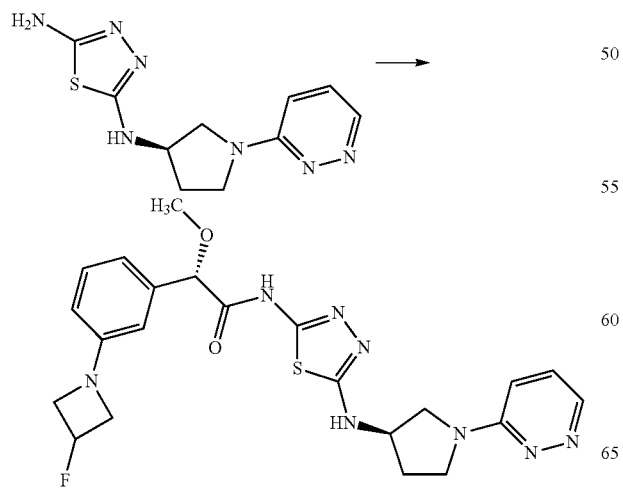

-continued

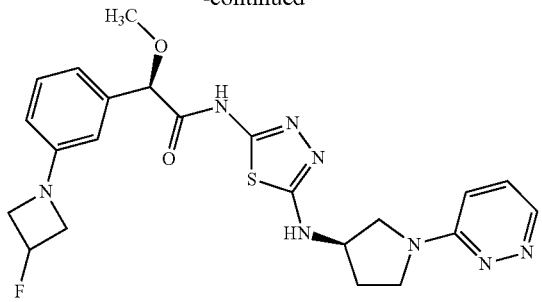

HATU (351 mg, 0.92 mmol) was added to [2-[3-(3-fluoroazetidin-1-yl)phenyl]-2-methoxy-acetyl]oxylithium (Intermediate 17, 170 mg, 0.71 mmol), N2-[(3R)-1-pyridazin-3-ylpyrrolidin-3-yl]-1,3,4-thiadiazole-2,5-diamine (Intermediate 1, 187 mg, 0.71 mmol) and DIPEA (0.372 mL, 2.13 mmol) in N-methyl-2-pyrrolidinone (2 mL) and DMF (3 mL) at r.t. The resulting solution was stirred at r.t. for 45 minutes. This solution was diluted with MeOH (15 mL) and passed through a 20 g SCX cartridge, flushing with MeOH followed by 1N NH$_3$ in MeOH to elute the product. The solvent was evaporated under reduced pressure to yield crude product which was dissolved in MeOH/DCM and evaporated onto silica gel. The residue was purified by FCC (SiO$_2$, 0 to 12% MeOH in DCM). Pure fractions were evaporated to dryness to afford the mixture of diastereoisomers as a gum (280 mg). The diastereoisomers were separated by preparative HPLC (Phenomenex Lux C4 column, 20 m, 50 mm×250 mm, MeOH at 120 mL/min) to give:

First eluted isomer example 1(a), 2-[3-(3-fluoroazetidin-1-yl)phenyl]-2-methoxy-N-[5-[[(3R)-1-pyridazin-3-ylpyrrolidin-3-yl]amino]-1,3,4-thiadiazol-2-yl]acetamide (65 mg, 23%). $^1$H NMR (400 MHz, DMSO-d6, 30° C.) δ 2.07 (1H, dq), 2.23-2.32 (1H, m), 3.40-3.59 (3H, m), 3.71-3.78 (1H, m), 3.80-3.93 (2H, m), 4.14 (2H, dt), 4.37 (1H, dt), 4.87 (1H, s), 5.48 (1H, dtt), 6.43 (1H, dd), 6.58 (1H, s), 6.80 (1H, d), 6.85 (1H, dd), 7.17 (1H, t), 7.32 (1H, dd), 7.64 (1H, d), 8.47 (1H, dd), 12.10 (1H, s). m/z: ES$^+$ [M+H]$^+$ 485.

Second eluted isomer example 1(b) 2-[3-(3-fluoroazetidin-1-yl)phenyl]-2-methoxy-N-[5-[[(3R)-1-pyridazin-3-ylpyrrolidin-3-yl]amino]-1,3,4-thiadiazol-2-yl]acetamide (68 mg, 24%). $^1$H NMR (400 MHz, DMSO-d6, 30° C.) δ2.06 (1H, dd), 2.28 (1H, td), 3.42-3.59 (3H, m), 3.75 (1H, dd), 3.8-3.93 (2H, m), 4.14 (2H, dt), 4.37 (1H, dt), 4.88 (1H, s), 5.48 (1H, ddd), 6.44 (1H, dd), 6.57-6.61 (1H, m), 6.81 (1H, d), 6.86 (1H, dd), 7.18 (1H, t), 7.32 (1H, dd), 7.65 (1H, d), 8.47 (1H, dd), 12.12 (1H, s). m/z: ES$^+$ [M+H]$^+$ 485.

Example 2(a) and 2(b)

(2S)-2-[3-(3,3-Difluoroazetidin-1-yl)phenyl]-2-methoxy-N-[5-[[(3R)-1-pyridazin-3-ylpyrrolidin-3-yl]amino]-1,3,4-thiadiazol-2-yl]acetamide and (2R)-2-[3-(3,3-Difluoroazetidin-1-yl)phenyl]-2-methoxy-N-[5-[[(3R)-1-pyridazin-3-ylpyrrolidin-3-yl]amino]-1,3,4-thiadiazol-2-yl]acetamide

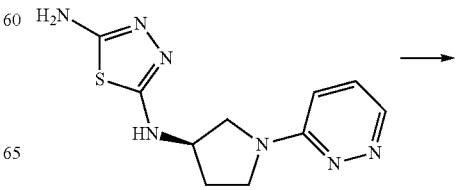

15

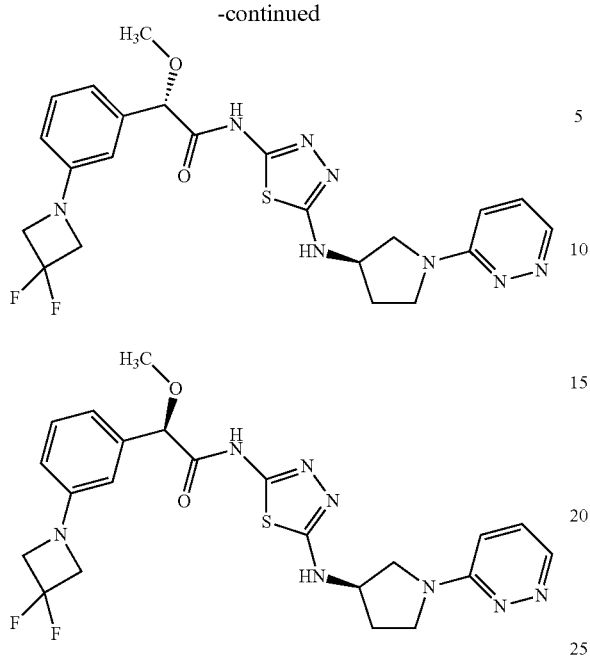

HATU (225 mg, 0.59 mmol) was added to 2-[3-(3,3-difluoroazetidin-1-yl)phenyl]-2-methoxy-acetic acid (Intermediate 22, 117 mg, 0.46 mmol), N2-[(3R)-1-pyridazin-3-ylpyrrolidin-3-yl]-1,3,4-thiadiazole-2,5-diamine (Intermediate 1, 120 mg, 0.46 mmol) and DIPEA (0.239 mL, 1.37 mmol) in N-methyl-2-pyrrolidinone (2 mL) and DMF (3 mL) at r.t. The resulting solution was stirred at r.t. for 45 minutes. This solution was diluted with MeOH (15 mL) and passed through a 20 g SCX2 cartridge, flushing with MeOH to remove impurities followed by a 1N solution of NH₃ in MeOH to elute the product. The solvent was evaporated under reduced pressure to yield crude product which was purified by FCC (SiO₂, 0 to 6% MeOH in DCM). Pure fractions were evaporated to afford the product as a mixture of diastereoisomers as a gum (135 mg). The diastereoisomers were separated by preparative HPLC (Phenomenex Lux C2 column, 20 m, 50 mm×250 mm, MeOH/EtOH at 120 mL/min) to give:

First eluted isomer example 2(a) 2-[3-(3,3-difluoroazetidin-1-yl)phenyl]-2-methoxy-N-[5-[[(3R)-1-pyridazin-3-ylpyrrolidin-3-yl]amino]-1,3,4-thiadiazol-2-yl]acetamide (55 mg, 41%). ¹H NMR (400 MHz, DMSO-d6, 30° C.) δ2.07 (1H, dt), 2.22-2.32 (1H, m), 3.48 (1H, dd), 3.51-3.59 (2H, m), 3.74 (1H, dd), 4.25 (4H, t), 4.37 (1H, dq), 4.89 (1H, s), 6.49-6.56 (1H, m), 6.67 (1H, d), 6.81-6.91 (2H, m), 7.21 (1H, t), 7.31 (1H, dd), 7.64 (1H, d), 8.46 (1H, dd), 12.11 (1H, s). m/z: ES⁺ [M+H]⁺ 503.

Second eluted isomer example 2(b) 2-[3-(3,3-difluoroazetidin-1-yl)phenyl]-2-methoxy-N-[5-[[(3R)-1-pyridazin-3-ylpyrrolidin-3-yl]amino]-1,3,4-thiadiazol-2-yl]acetamide (61 mg, 45%). ¹H NMR (400 MHz, DMSO-d6, 30° C.) 2.00-2.11 (1H, m), 2.22-2.31 (1H, m), 3.48 (1H, dd), 3.52-3.59 (2H, m), 3.74 (1H, dd), 4.25 (4H, t), 4.36 (1H, dt), 4.88 (1H, s), 6.52 (1H, dd), 6.66 (1H, s), 6.82-6.91 (2H, m), 7.21 (1H, t), 7.31 (1H, dd), 7.61 (1H, d), 8.47 (1H, dd), 12.11 (1H, s). m/z: ES⁺ [M+H]⁺ 503.

16

Example 3(a) and 3(b)

(2S)-2-Methoxy-2-[3-(3-methoxyazetidin-1-yl)phenyl]-N-[5-[[(3R)-1-pyridazin-3-ylpyrrolidin-3-yl]amino]-1,3,4-thiadiazol-2-yl]acetamide and (2R)-2-Methoxy-2-[3-(3-methoxyazetidin-1-yl)phenyl]-N-[5-[[(3R)-1-pyridazin-3-ylpyrrolidin-3-yl]amino]-1,3,4-thiadiazol-2-yl]acetamide

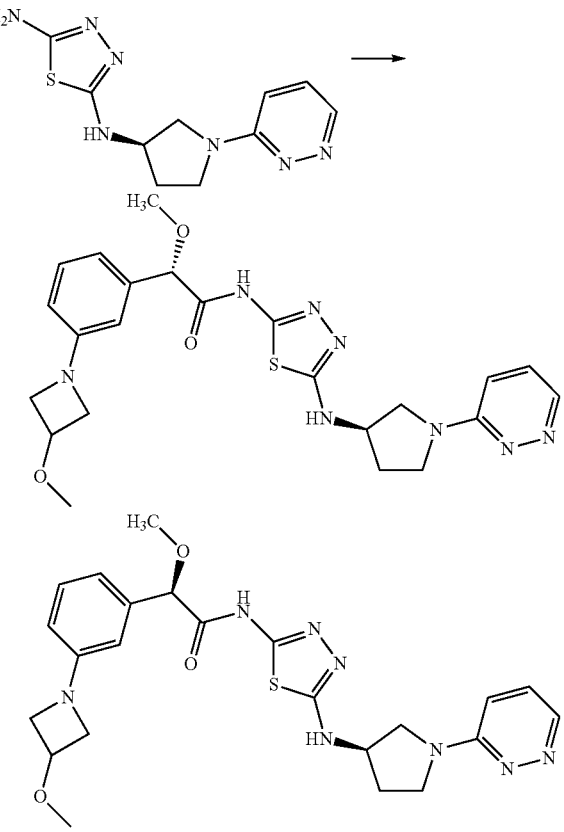

HATU (216 mg, 0.57 mmol) was added to 2-methoxy-2-[3-(3-methoxyazetidin-1-yl)phenyl]acetic acid (Intermediate 25, 110 mg, 0.44 mmol), N2-[(3R)-1-pyridazin-3-ylpyrrolidin-3-yl]-1,3,4-thiadiazole-2,5-diamine (Intermediate 1, 115 mg, 0.44 mmol) and DIPEA (0.229 mL, 1.31 mmol) in N-methyl-2-pyrrolidinone (2 mL) and DMF (3 mL) at r.t. The resulting solution was stirred at r.t. for 45 minutes. This solution was diluted with MeOH (15 mL) and passed through a 20 g SCX2 cartridge, flushing with MeOH to remove impurities followed by a 1N solution of NH₃ in MeOH to elute the product. The solvent was evaporated under reduced pressure to yield crude product. The crude product was dissolved in MeOH/DCM and evaporated down onto silica gel. The residue was purified by FCC (SiO₂, 0 to 10% MeOH in DCM). Pure fractions were evaporated to dryness to afford the product as a mixture of diastereoisomers (140 mg) as a gum. The combined diastereoisomers were separated by preparative HPLC (Lux C4 column, 20 μm, 50 mm×250 mm, 100% MeOH at 120 mL/min) to give:

First eluted isomer example 3(a) 2-methoxy-2-[3-(3-methoxyazetidin-1-yl)phenyl]-N-[5-[[(3R)-1-pyridazin-3-ylpyrrolidin-3-yl]amino]-1,3,4-thiadiazol-2-yl]acetamide (74 mg, 15%). ¹H NMR (400 MHz, DMSO-d6, 30° C.)

δ2.13 (1H, td), 2.3-2.38 (1H, m), 3.30 (3H, s), 3.35 (3H, s), 3.54 (1H, dd), 3.58-3.67 (4H, m), 3.81 (1H, dd), 4.05-4.12 (2H, m), 4.37 (1H, ddd), 4.44 (1H, dq), 4.92 (1H, s), 6.45 (1H, dd), 6.61 (1H, d), 6.82 (1H, d), 6.91 (1H, dd), 7.21 (1H, t), 7.38 (1H, dd), 7.71 (1H, d), 8.53 (1H, dd), 12.16 (1H, s). m/z: ES+ [M+H]+ 497.

Second eluted isomer example 3(b) 2-methoxy-2-[3-(3-methoxyazetidin-1-yl)phenyl]-N-[5-[[(3R)-1-pyridazin-3-ylpyrrolidin-3-yl]amino]-1,3,4-thiadiazol-2-yl]acetamide (67 mg, 14%). ¹H NMR (400 MHz, DMSO-d6, 30° C.) δ2.11 (1H, dq), 2.33 (1H, dt), 3.29 (3H, s), 3.34 (3H, s), 3.54 (1H, dd), 3.58-3.66 (4H, m), 3.80 (1H, dd), 4.05-4.12 (2H, m), 4.36 (1H, ddd), 4.4-4.47 (1H, m), 4.91 (1H, s), 6.44 (1H, dd), 6.60 (1H, s), 6.82 (1H, d), 6.91 (1H, dd), 7.20 (1H, t), 7.37 (1H, dd), 7.69 (1H, d), 8.53 (1H, dd), 12.15 (1H, s). m/z: ES+ [M+H]+ 497.

Example 4(a) and 4(b)

(2S)-2-(3,5-Dimethoxyphenyl)-2-methoxy-N-[5-[[(3R)-1-(6-methylpyridazin-3-yl)pyrrolidin-3-yl]amino]-1,3,4-thiadiazol-2-yl]acetamide and (2R)-2-(3,5-Dimethoxyphenyl)-2-methoxy-N-[5-[[(3R)-1-(6-methylpyridazin-3-yl)pyrrolidin-3-yl]amino]-1,3,4-thiadiazol-2-yl]acetamide

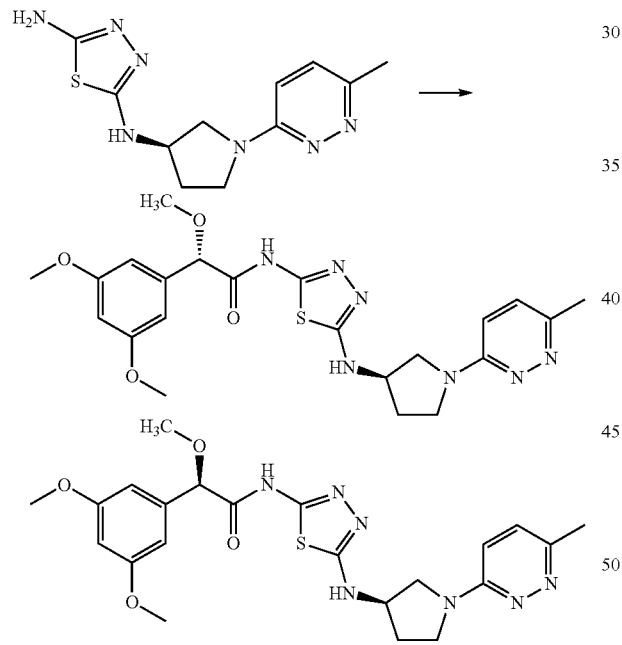

HATU (329 mg, 0.87 mmol) was added to 2-(3,5-dimethoxyphenyl)-2-methoxy-acetic acid (Intermediate 28, 196 mg, 0.87 mmol), N2-[(3R)-1-(6-methylpyridazin-3-yl)pyrrolidin-3-yl]-1,3,4-thiadiazole-2,5-diamine (Intermediate 6, 200 mg, 0.72 mmol) and DIPEA (0.252 mL, 1.44 mmol) in DMF (6 mL) at 21° C. under nitrogen. The resulting solution was stirred at 21° C. for 2 hours. The crude mixture was purified by ion exchange chromatography, using an SCX column. The desired product was eluted from the column using 1M NH₃ in MeOH and pure fractions were evaporated to dryness to afford crude product which was purified by FCC (SiO₂, 0 to 12% MeOH in DCM). Pure fractions were evaporated to dryness to afford a brown gum which was repurified by FCC (SiO₂, 0 to 8% MeOH in DCM). Pure fractions were evaporated to dryness to afford the mixture of diastereoisomers as a yellow gum. The diastereoisomers were separated by preparative HPLC (Lux C2 column, 20 m, 50 mm×250 mm, 100% MeOH at 120 mL/min) to give:

First eluted isomer example 4(a) 2-(3,5-dimethoxyphenyl)-2-methoxy-N-[5-[[(3R)-1-(6-methylpyridazin-3-yl)pyrrolidin-3-yl]amino]-1,3,4-thiadiazol-2-yl]acetamide (21 mg, 6%). ¹H NMR (400 MHz, DMSO-d6, 27° C.) δ1.98-2.10 (1H, m), 2.18-2.31 (1H, m), 2.40 (3H, s), 3.30 (9H, s), 3.43 (1H, m), 3.47-3.61 (2H, m), 3.72 (1H, m), 4.36 (1H, m), 4.87 (1H, s), 6.45 (1H, t), 6.62 (2H, d), 6.81 (1H, d), 7.21 (1H, d), 7.64 (1H, s), 12.12 (1H, s). m/z: ES+ [M+H]+ 486.

Second eluted isomer example 4(b) 2-(3,5-dimethoxyphenyl)-2-methoxy-N-[5-[[(3R)-1-(6-methylpyridazin-3-yl)pyrrolidin-3-yl]amino]-1,3,4-thiadiazol-2-yl]acetamide (18 mg, 5%). ¹H NMR (400 MHz, DMSO-d6, 27° C.) δ1.98-2.10 (1H, m), 2.18-2.31 (1H, m), 2.40 (3H, s), 3.30 (9H, s), 3.43 (1H, m), 3.47-3.61 (2H, m), 3.72 (1H, m), 4.36 (1H, m), 4.87 (1H, s), 6.45 (1H, t), 6.62 (2H, d), 6.81 (1H, d), 7.21 (1H, d), 7.64 (1H, s), 12.12 (1H, s). m/z: ES+ [M+H]+ 486.

Example 5(a) and 5(b)

(2R)-3-Methoxy-2-(3-methoxyphenyl)-N-[5-[[(3R)-1-pyridazin-3-ylpyrrolidin-3-yl]amino]-1,3,4-thiadiazol-2-yl]propanamide and (2S)-3-Methoxy-2-(3-methoxyphenyl)-N-[5-[[(3R)-1-pyridazin-3-ylpyrrolidin-3-yl]amino]-1,3,4-thiadiazol-2-yl]propanamide

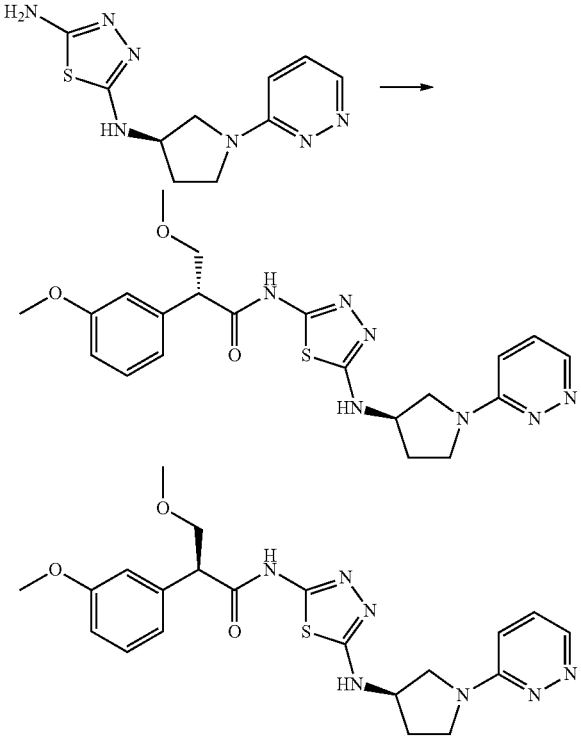

DIPEA (0.1 mL, 0.57 mmol), HATU (173.28 mg, 0.456 mmol) and 3-methoxy-2-(3-methoxyphenyl)propanoic acid (Intermediate 29, 0.09 g, 0.418 mmol) were added to a solution of N2-[(3R)-1-pyridazin-3-ylpyrrolidin-3-yl]-1,3,4- thiadiazole-2,5-diamine (Intermediate 1, 0.1 g, 0.38 mmol) in DMF (4 mL). The mixture was stirred at r.t. for 18 h. This was diluted with water (5 mL), extracted into DCM (10 mL), evaporated and purified by preparative HPLC (SunFire C18 column, 5 m, 50 mm×19 mm, flow rate 25 mL/min). Decreasingly polar ratios of water and MeCN containing 0.1% formic acid were used as a mobile phase. Pure fractions were passed down an SCX cartridge washing with methanol and then eluting with 2M NH$_3$ in MeOH. The basic fraction was evaporated to dryness and the mixture of diastereoisomers were separated by SFC (Lux C1 column 5 μm, 21.2 mm×250 mm, at 40° C. at a flow rate of 50 mL/min, 50:50 MeOH:CO$_2$ containing 0.1% v/v NH$_3$) to give:

First eluted isomer example 5(a) 3-methoxy-2-(3-methoxyphenyl)-N-[5-[[(3R)-1-pyridazin-3-ylpyrrolidin-3-yl]amino]-1,3,4-thiadiazol-2-yl]propanamide (25.3 mg, 14.6%). $^1$H NMR (400 MHz, DMSO-d6, 25° C.) δ2.00-2.12 (1H, m), 2.22-2.31 (1H, m), 3.25 (3H, s), 3.45-3.59 (4H, m), 3.71-3.79 (4H, m), 3.97 (1H, t), 4.03-4.10 (1H, m), 4.31-4.43 (1H, m), 6.83-6.94 (4H, m), 7.26 (1H, t), 7.33 (1H, dd), 7.68 (1H, d), 8.48 (1H, dd), 12.23 (1H, s). m/z: ES$^+$ [M+H]$^+$ 456.

Second eluted isomer example 5(b) 3-methoxy-2-(3-methoxyphenyl)-N-[5-[[(3R)-1-pyridazin-3-ylpyrrolidin-3-yl]amino]-1,3,4-thiadiazol-2-yl]propanamide (22.3 mg, 12.8%). $^1$H NMR (400 MHz, DMSO-d6, 25° C.) δ2.00-2.14 (1H, m), 2.22-2.36 (1H, m), 3.25 (3H, s), 3.43-3.52 (2H, m), 3.52-3.61 (2H, m), 3.69-3.78 (4H, m), 3.97 (1H, t), 4.01-4.10 (1H, m), 4.31-4.43 (1H, m), 6.79-6.95 (4H, m), 7.26 (1H, t), 7.33 (1H, dd), 7.68 (1H, d), 8.47 (1H, dd), 12.23 (1H, s). m/z: ES$^+$ [M+H]$^+$ 456.

Example 6(a) and 6(b)

(2S)-2-(3,5-Dimethoxyphenyl)-2-ethoxy-N-[5-[[(3R)-1-pyridazin-3-ylpyrrolidin-3-yl]amino]-1,3,4-thiadiazol-2-yl]acetamide and (2R)-2-(3,5-Dimethoxyphenyl)-2-ethoxy-N-[5-[[(3R)-1-pyridazin-3-ylpyrrolidin-3-yl]amino]-1,3,4-thiadiazol-2-yl]acetamide

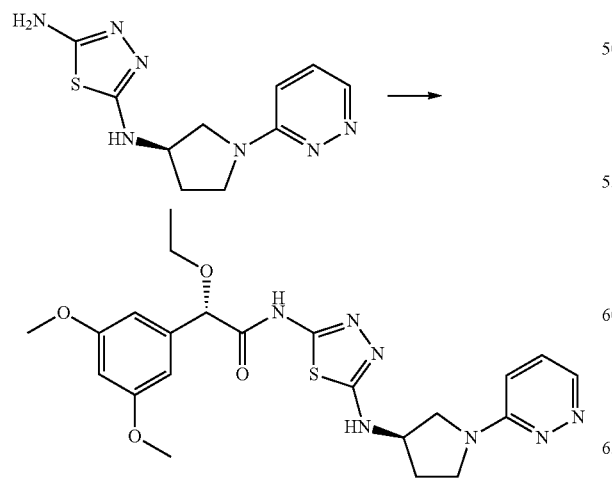

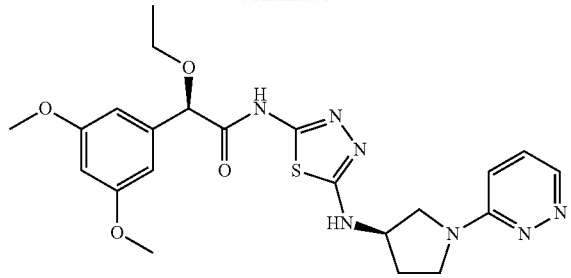

N2-[(3R)-1-Pyridazin-3-ylpyrrolidin-3-yl]-1,3,4-thiadiazole-2,5-diamine (Intermediate 1, 0.2 g, 0.76 mmol) and 2-(3,5-dimethoxyphenyl)-2-ethoxy-acetic acid (Intermediate 33, 0.18 g, 0.76 mmol) were dissolved in DMF (2 mL) at r.t under N$_2$. The mixture was stirred for 5 min before addition of DIPEA (0.34 mL, 1.943 mmol) and HATU (0.29 g, 0.76 mmol), then at r.t. for 1 h. The crude mixture was passed through a 5 g SCX column washed with MeOH then eluted with 2N NH$_3$ in MeOH. The basic fraction was purified by preparative HPLC (SunFire C18 column, 5 m, 50 mm×19 mm, flow rate 25 mL/min). Decreasingly polar ratios of water and MeCN containing 0.1% formic acid were used as a mobile phase. Pure fractions were evaporated under reduced pressure and passed through a 2 g SCX column washed with MeOH then eluted with 2N NH$_3$ in MeOH. The basic fraction was evaporated under reduced pressure to give the product as a mixture of diastereoisomers as a beige foam. The diastereoisomers were separated by SFC (Amy-C column, 5 μm, 20 mm×250 mm, MeOH/CO$_2$ 45% containing NH$_3$ as modifier at 50 mL/min) to give:

First eluted isomer example 6(a) 2-(3,5-dimethoxyphenyl)-2-ethoxy-N-[5-[[(3R)-1-pyridazin-3-ylpyrrolidin-3-yl]amino]-1,3,4-thiadiazol-2-yl]acetamide (70 mg, 19%). $^1$H NMR (400 MHz, DMSO-d6, 21° C.) δ1.16 (3H, t), 2.04 (1H, dq), 3.38-3.50 (3H, m), 3.51-3.58 (2H, m), 3.66-3.78 (7H, m), 4.35 (1H, q), 4.96 (1H, s), 6.44 (1H, t), 6.62 (2H, d), 6.84 (1H, dd), 7.30 (1H, dd), 7.67 (1H, d), 8.45 (1H, dd), 11.96 (1H, s). m/z: ES$^+$ [M+H]$^+$ 486.

Second eluted isomer example 6(b) 2-(3,5-dimethoxyphenyl)-2-ethoxy-N-[5-[[(3R)-1-pyridazin-3-ylpyrrolidin-3-yl]amino]-1,3,4-thiadiazol-2-yl]acetamide (74 mg, 20%). $^1$H NMR (400 MHz, DMSO-d6, 21° C.) δ1.18 (3H, t), 2.07 (1H, dt), 2.27 (1H, dt), 3.60-3.39 (5H, m), 3.79-3.70 (6H, m), 4.38 (1H, q), 4.99 (1H, s), 6.47 (1H, t), 6.64 (2H, d), 6.88 (1H, dd), 7.34 (1H, dd), 7.71 (1H, d), 8.48 (1H, dd), 12.15 (1H, s). m/z: ES$^+$ [M+H]$^+$ 486.

Example 7(a) and 7(b)

(2S)-2-[4-Fluoro-3-(3-methoxyazetidin-1-yl)phenyl]-2-methoxy-N-[5-[(3R)-3-(pyridazin-3-ylamino)pyrrolidin-1-yl]-1,3,4-thiadiazol-2-yl]acetamide and (2R)-2-[4-Fluoro-3-(3-methoxyazetidin-1-yl)phenyl]-2-methoxy-N-[5-[(3R)-3-(pyridazin-3-ylamino)pyrrolidin-1-yl]-1,3,4-thiadiazol-2-yl]acetamide

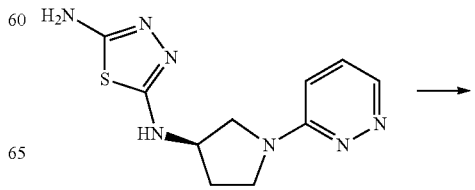

-continued

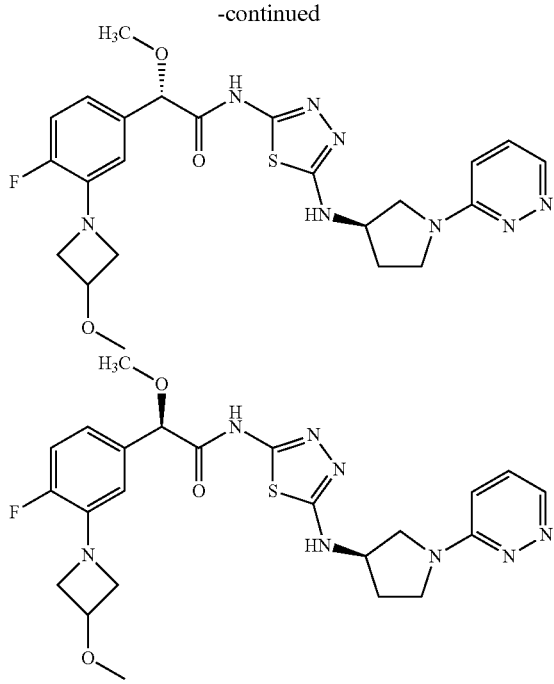

N2-[(3R)-1-Pyridazin-3-ylpyrrolidin-3-yl]-1,3,4-thiadiazole-2, 5-diamine (Intermediate 1, 108 mg, 0.41 mmol) and 2-[4-fluoro-3-(3-methoxyazetidin-1-yl)phenyl]-2-methoxy-acetic acid (Intermediate 34, 110 mg, 0.41 mmol) were dissolved in DMF (3.5 mL) at r.t. under nitrogen. The mixture was stirred for 5 minutes before addition of DIPEA (0.11 mL, 0.61 mmol) and HATU (186 mg, 0.49 mmol) then stirred at r.t. overnight. The crude mixture was diluted with water (50 mL) and then extracted into DCM (3×50 mL). The organic layer was dried (MgSO$_4$), filtered and then evaporated to give an orange gum which was purified by preparative HPLC (SunFire C18 column, 5 µm, 50 mm×19 mm, flow rate 25 mL/min). Decreasingly polar ratios of water and MeCN containing 0.1% formic acid were used as a mobile phase. Fractions containing the desired product were combined, evaporated and passed through a 5 g SCX column washed with MeOH then eluted with 2 M NH$_3$ in MeOH. The basic fraction was evaporated to give the mixture of diastereoisomers. The diastereoisomers were then separated by SFC (Lux C3 column, 5 m, 21.2 mm×250 mm, MeOH/CO$_2$ 30% containing NH$_3$ modifier, 50 mL/min) to give:

First eluted isomer example 7(a) 2-[4-fluoro-3-(3-methoxyazetidin-1-yl)phenyl]-2-methoxy-N-[5-[(3R)-3-(pyridazin-3-ylamino)pyrrolidin-1-yl]-1,3,4-thiadiazol-2-yl]acetamide (11 mg, 5%). $^1$H NMR (400 MHz, DMSO-d6, 21° C.) δ1.94-2.12 (1H, m), 2.19-2.36 (1H, m), 3.23 (3H, s), 3.27 (3H, s), 3.43-3.61 (3H, m), 3.62-3.77 (3H, m), 4.07-4.19 (2H, m), 4.22-4.30 (1H, m), 4.32-4.43 (1H, m), 4.87 (1H, s), 6.66 (1H, dd), 6.73-6.84 (1H, m), 6.86 (1H, dd), 7.04 (1H, dd), 7.32 (1H, dd), 7.70 (1H, d), 8.47 (1H, dd), 12.18 (1H, s). m/z: ES$^+$[M+H]$^+$ 515.

Second eluted isomer example 7(b) 2-[4-fluoro-3-(3-methoxyazetidin-1-yl)phenyl]-2-methoxy-N-[5-[(3R)-3-(pyridazin-3-ylamino)pyrrolidin-1-yl]-1,3,4-thiadiazol-2-yl]acetamide (11 mg, 5%). $^1$H NMR (400 MHz, DMSO-d6, 21° C.) δ2.00-2.13 (1H, m), 2.22-2.34 (1H, m), 3.23 (3H, s), 3.28 (3H, s), 3.42-3.60 (3H, m), 3.63-3.80 (3H, m), 4.09-4.18 (2H, m), 4.24-4.33 (1H, m), 4.43-4.45 (1H, m), 4.87 (1H, s), 6.67 (1H, dd), 6.75-6.83 (1H, m), 6.87 (1H, dd), 7.05 (1H, dd), 7.33 (1H, dd), 7.70 (1H, d), 8.48 (1H, dd), 12.18 (1H, s). m/z: ES$^+$[M+H]$^+$ 515.

Example 8(a) and 8(b)

(2S)-2-[4-Fluoro-3-(3-fluoroazetidin-1-yl)phenyl]-2-methoxy-N-[5-[[(3R)-1-pyridazin-3-ylpyrrolidin-3-yl]amino]-1,3,4-thiadiazol-2-yl]acetamide and (2R)-2-[4-Fluoro-3-(3-fluoroazetidin-1-yl)phenyl]-2-methoxy-N-[5-[[(3R)-1-pyridazin-3-ylpyrrolidin-3-yl]amino]-1,3,4-thiadiazol-2-yl]acetamide

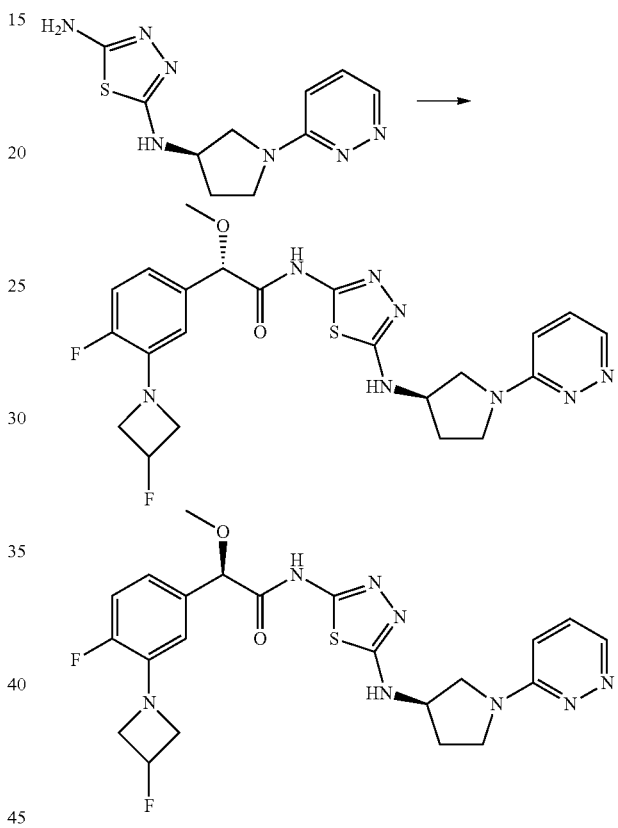

N2-[(3R)-1-Pyridazin-3-ylpyrrolidin-3-yl]-1,3,4-thiadiazole-2,5-diamine (Intermediate 1, 100 mg, 0.38 mmol) and lithium 2-[4-fluoro-3-(3-fluoroazetidin-2.33 (1H, m-yl)phenyl], 3.49-2-methoxy-acetate (Intermediate 38, 100 mg, 0.38 mmol) were dissolved in DMF (2.0 mL) at r.t under N$_2$. The mixture was stirred for 5 minutes before addition of DIPEA (0.10 mL, 0.57 mmol) and HATU (173 mg, 0.46 mmol) then stirred at r.t. overnight. The crude mixture was passed through a 5 g SCX column, washed with MeOH, then eluted with 2M NH$_3$ in MeOH. The basic fraction was evaporated to give an orange gum. The crude product was purified by preparative HPLC (SunFire C18 column, 5 m, 50 mm×19 mm at 25 mL/min). Decreasingly polar ratios of water and MeCN containing 0.1% formic acid were used as a mobile phase. Fractions containing the product were combined, evaporated and passed through a 5 g SCX column washed with MeOH then eluted with 2M NH$_3$ in MeOH. The basic fraction was evaporated to give the mixture of diastereoisomers as an off-white solid (94 mg). The diastereoisomers were separated by preparative HPLC (Lux C4 column, 20 m, 50 mm×250 mm, MeOH/EtOH at 120 mL/min) to give:

First eluted isomer example 8(a) 2-[4-fluoro-3-(3-fluoroazetidin-1-yl)phenyl]-2-methoxy-N-[5-[[(3R)-1-pyridazin-3-ylpyrrolidin-3-yl]amino]-1,3,4-thiadiazol-2-yl]acetamide (33 mg, 17%). ¹H NMR (400 MHz, DMSO, 31° C.) 2.03-2.13 (1H, m), 2.24-2.33 (1H, m), 3.49 (1H, dd), 3.54-3.61 (2H, m), 3.75 (1H, dd), 3.97 (2H, dd), 4.19-4.31 (2H, m), 4.35-4.43 (1H, m), 4.89 (1H, s), 5.36-5.56 (1H, m), 6.71 (1H, dd), 6.8-6.89 (2H, m), 7.07 (1H, dd), 7.32 (1H, dd), 7.65 (1H, d), 8.48 (1H, dd), 12.13 (1H, s). m/z: ES⁺ [M+H]⁺ 503.

Second eluted isomer example 8(b) 2-[4-fluoro-3-(3-fluoroazetidin-1-yl)phenyl]-2-methoxy-N-[5-[[(3R)-1-pyridazin-3-ylpyrrolidin-3-yl]amino]-1,3,4-thiadiazol-2-yl]acetamide (34 mg, 18%). ¹H NMR (400 MHz, DMSO, 30° C.) 2.01-2.11 (1H, m), 2.24-2.34 (1H, m), 3.47-3.61 (3H, m), 3.76 (1H, dd), 3.97 (2H, dd), 4.18-4.32 (2H, m), 4.35-4.43 (1H, m), 4.88 (1H, s), 5.35-5.57 (1H, m), 6.71 (1H, dd), 6.81-6.89 (2H, m), 7.07 (1H, dd), 7.33 (1H, dd), 7.64 (1H, d), 8.48 (1H, d), 12.14 (1H, s), 21 assigned Hs: plus OMe protons not observed—obscured by solvent at 3.30 ppm. m/z: ES⁺ [M+H]⁺ 503.

Example 9(a) and 9(b)

(2S)—N-[5-[[(3R)-1-(6-Fluoropyridazin-3-yl)pyrrolidin-3-yl]amino]-1,3,4-thiadiazol-2-yl]-2-methoxy-2-[3-(3-methoxyazetidin-1-yl)phenyl]acetamide and (2R)—N-[5-[[(3R)-1-(6-Fluoropyridazin-3-yl)pyrrolidin-3-yl]amino]-1,3,4-thiadiazol-2-yl]-2-methoxy-2-[3-(3-methoxyazetidin-1-yl)phenyl]acetamide

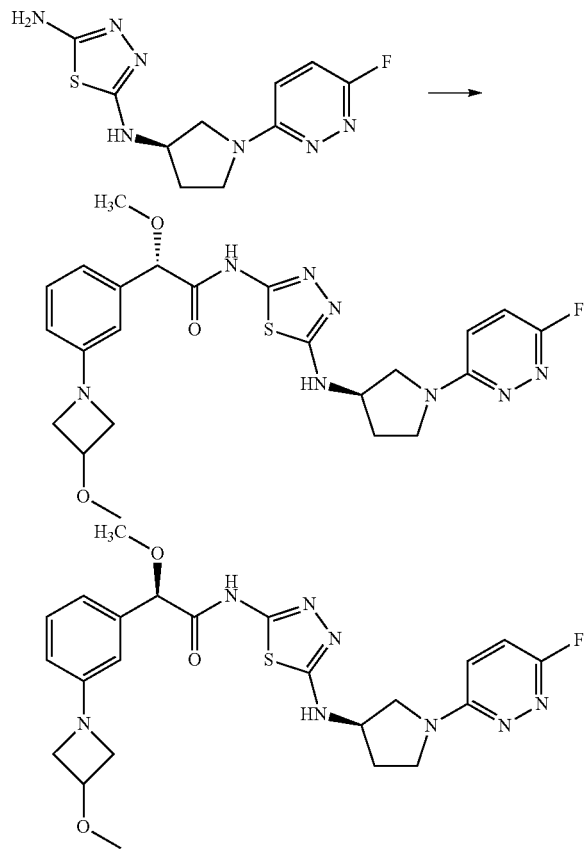

N2-[(3R)-1-(6-Fluoropyridazin-3-yl)pyrrolidin-3-yl]-1,3,4-thiadiazole-2,5-diamine (Intermediate 9, 0.11 g, 0.389 mmol) and [2-methoxy-2-[3-(3-methoxyazetidin-1-yl)phenyl]acetyl]oxylithium (Intermediate 24, 0.12 g, 0.466 mmol) were dissolved in DMF (2 mL) at r.t under N₂. The mixture was stirred for 5 min before addition of DIPEA (0.34 mL, 1.943 mmol), and HATU (0.4 mL, 0.389 mmol), then at r.t. for 2 h. The crude mixture was left to sit overnight, then passed through a 5 g SCX column washed with MeOH then eluted with 2N NH₃ in MeOH. The basic fraction was evaporated to give an orange gum which was purified by preparative HPLC (SunFire C18 column, 5 μm, 50 mm×19 mm, flow rate 25 mL/min). Decreasingly polar ratios of water and MeCN containing 0.1% formic acid were used as a mobile phase. Pure fractions were combined, evaporated and passed through a 1 g SCX column washed with MeOH then eluted with 2N NH₃ in MeOH to give the mixture of diastereoisomers as an off-white solid. The mixture of diastereoisomers was separated by preparative chiral HPLC (Phenomenex Lux C4 column, 20 μm, 50 mm×250 mm, eluent MeOH at 120 mL/min) to give:

First eluted isomer example 9(a) N-[5-[[(3R)-1-(6-fluoropyridazin-3-yl)pyrrolidin-3-yl]amino]-1,3,4-thiadiazol-2-yl]-2-methoxy-2-[3-(3-methoxyazetidin-1-yl)phenyl]acetamide (39.1 mg, 19.5%). ¹H NMR (400 MHz, DMSO-d6, 21° C.) δ2.07 (1H, dt), 2.27 (1H, dt), 3.24 (3H, s), 3.28 (3H, s), 3.46 (1H, dd), 3.50-3.61 (4H, m), 3.73 (1H, dd), 4.00-4.07 (2H, m), 4.27-4.42 (2H, m), 4.84 (1H, s), 6.39 (1H, dd), 6.55 (1H, s), 6.76 (1H, d), 7.12-7.20 (2H, m), 7.36 (1H, dd), 7.63 (1H, d), 12.16 (1H, s). m/z: ES⁺ [M+H]⁺ 515.

Second eluted isomer example 9(b) N-[5-[[(3R)-1-(6-fluoropyridazin-3-yl)pyrrolidin-3-yl]amino]-1,3,4-thiadiazol-2-yl]-2-methoxy-2-[3-(3-methoxyazetidin-1-yl)phenyl]acetamide (42.8 mg, 21.4%). ¹H NMR (400 MHz, DMSO-d6, 21° C.) δ2.05 (1H, td), 2.27 (1H, dt), 3.24 (3H, s), 3.28 (3H, s), 3.47 (1H, dd), 3.5-3.6 (4H, m), 3.73 (1H, dd), 3.99-4.07 (2H, m), 4.27-4.4 (2H, m), 4.83 (1H, s), 6.39 (1H, dd), 6.55 (1H, d), 6.77 (1H, d), 7.12-7.2 (2H, m), 7.36 (1H, dd), 7.59 (1H, d), 12.17 (1H, s). m/z: ES⁺ [M+H]⁺ 515.

Example 10(a) and 10(b)

(2S)-2-[3-(3-Fluoroazetidin-1-yl)-5-methoxy-phenyl]-2-methoxy-N-[5-[[(3R)-1-pyridazin-3-ylpyrrolidin-3-yl]amino]-1,3,4-thiadiazol-2-yl]acetamide and (2R)-2-[3-(3-Fluoroazetidin-1-yl)-5-methoxy-phenyl]-2-methoxy-N-[5-[[(3R)-1-pyridazin-3-ylpyrrolidin-3-yl]amino]-1,3,4-thiadiazol-2-yl]acetamide

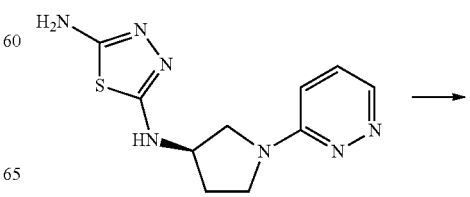

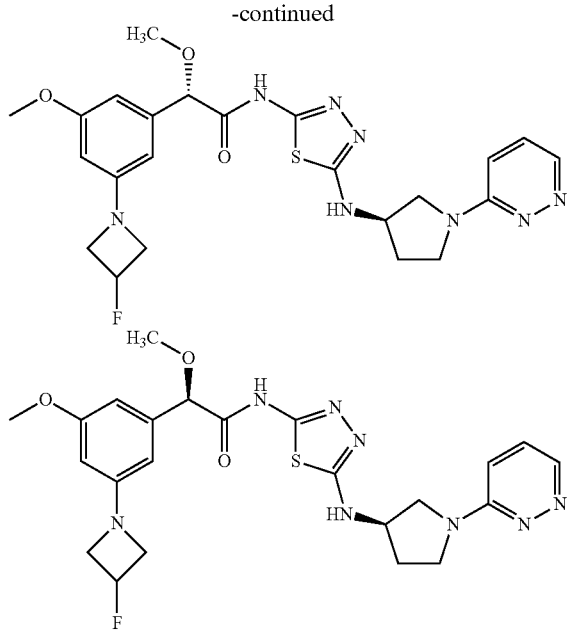

N2-[(3R)-1-pyridazin-3-ylpyrrolidin-3-yl]-1,3,4-thiadiazole-2, 5-diamine (Intermediate 1, 134 mg, 0.51 mmol) and lithium 2-[3-(3-fluoroazetidin-1-yl)-5-methoxy-phenyl]-2-methoxy-acetate (Intermediate 40, 137 mg, 0.51 mmol) were dissolved in DMF (2 mL) at r.t under $N_2$. The mixture was stirred for 5 minutes before addition of DIPEA (0.13 mL, 0.76 mmol) and HATU (232 mg, 0.61 mmol) then stirred at r.t. overnight. The crude mixture was passed through a 5 g SCX column, washed with MeOH, then eluted with 2 M $NH_3$ in MeOH. The basic fraction was evaporated to give an orange gum which was purified by preparative HPLC (SunFire C18 column, 5 m, 50 mm×19 mm, flow rate 25 mL/min. Decreasingly polar ratios of water and MeCN containing 0.1% formic acid were used as a mobile phase. Fractions containing the desired mass were combined, evaporated and passed through a 5 g SCX column, washed with MeOH, then eluted with 2M $NH_3$ in MeOH. The basic fraction was evaporated to give the mixture of diastereoisomers as an off-white solid (123 mg). The diastereoisomers were separated by preparative HPLC (Lux C4 column, 20 m, 50 mm×250 mm, 100% MeOH at 120 mL/min) to give:

First eluted isomer example 10(a) 2-[3-(3-fluoroazetidin-1-yl)-5-methoxy-phenyl]-2-methoxy-N-[5-[[(3R)-1-pyridazin-3-ylpyrrolidin-3-yl]amino]-1,3,4-thiadiazol-2-yl]acetamide (45 mg, 17%). $^1$H NMR (400 MHz, DMSO, 22° C.) 2.07 (1H, dq), 2.28 (1H, dt), 3.28 (3H, s), 3.49 (1H, dd), 3.52-3.59 (2H, m), 3.71 (3H, s), 3.74 (1H, dd), 3.80-3.86 (1H, m), 3.86-3.92 (1H, m), 4.06-4.20 (2H, m), 4.37 (1H, dt), 4.82 (1H, s), 5.47 (1H, dtd), 5.98 (1H, t), 6.13-6.21 (1H, m), 6.39-6.45 (1H, m), 6.86 (1H, dd), 7.33 (1H, dd), 7.67 (1H, d), 8.48 (1H, dd), 12.13 (1H, s). m/z: ES$^+$ [M+H]$^+$ 515.

Second eluted isomer example 10(b) 2-[3-(3-fluoroazetidin-1-yl)-5-methoxy-phenyl]-2-methoxy-N-[5-[[(3R)-1-pyridazin-3-ylpyrrolidin-3-yl]amino]-1,3,4-thiadiazol-2-yl]acetamide (46 mg, 17%). $^1$H NMR (400 MHz, DMSO, 22° C.) 2.06 (1H, dq), 2.27 (1H, dt), 3.28 (3H, s), 3.49 (1H, dd), 3.53-3.59 (2H, m), 3.71 (3H, s), 3.75 (1H, dd), 3.80-3.86 (1H, m), 3.87-3.92 (1H, m), 4.13 (2H, dt), 4.37 (1H, dt), 4.81 (1H, s), 5.47 (1H, dtt), 5.97 (1H, t), 6.13-6.23 (1H, m), 6.38-6.45 (1H, m), 6.87 (1H, dd), 7.33 (1H, dd), 7.64 (1H, d), 8.48 (1H, dd), 12.15 (1H, s). m/z: ES$^+$ [M+H]$^+$ 515.

Example 11(a) and 11(b)

(2S)-2-Methoxy-2-[3-methoxy-5-(trifluoromethoxy)phenyl]-N-[5-[[(3R)-1-pyridazin-3-ylpyrrolidin-3-yl]amino]-1,3,4-thiadiazol-2-yl]acetamide and (2R)-2-methoxy-2-[3-methoxy-5-(trifluoromethoxy)phenyl]-N-[5-[[(3R)-1-pyridazin-3-ylpyrrolidin-3-yl]amino]-1,3,4-thiadiazol-2-yl]acetamide

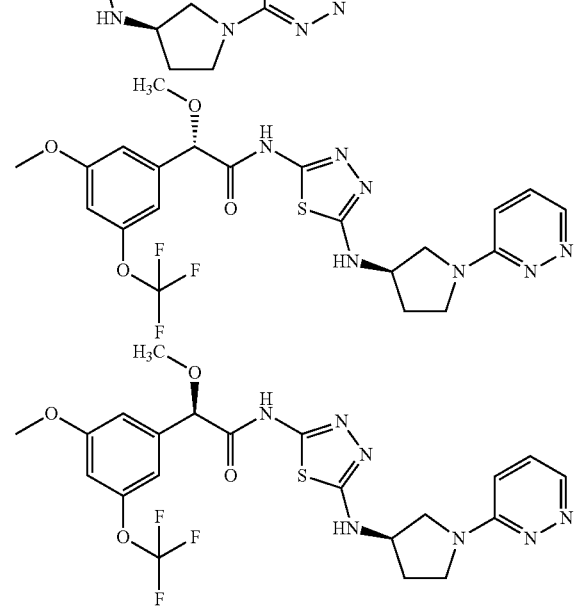

N2-[(3R)-1-Pyridazin-3-ylpyrrolidin-3-yl]-1,3,4-thiadiazole-2, 5-diamine (Intermediate 1, 100 mg, 0.38 mmol) and 2-methoxy-2-[3-methoxy-5-(trifluoromethoxy)phenyl]acetic acid (Intermediate 44, 191 mg, 0.68 mmol) were dissolved in DMF (3.5 mL) at r.t under $N_2$. The mixture was stirred for 5 minutes before addition of DIPEA (0.1 mL, 0.57 mmol) and HATU (173 mg, 0.46 mmol) then stirred at r.t. overnight. The crude mixture was diluted with water (50 mL) and extracted into DCM (50 mL×2). The organic layer was dried (MgSO$_4$), filtered and evaporated to afford an orange gum which was purified by preparative HPLC (SunFire C18 column, 5 μm, 50 mm×19 mm, flow rate 25 mL/min). Decreasingly polar ratios of water and MeCN containing 0.1% formic acid were used as a mobile phase. Fractions containing the desired mass were combined, evaporated and passed through a 5 g SCX column washed with MeOH then eluted with 2M $NH_3$ in MeOH. The basic fraction was evaporated to give a yellow solid. The mixture of diastereoisomers was separated by preparative HPLC (Phenomenex Lux C2 column, 20 m, 50 mm×250 mm, using a 50/50 mixture of EtOH/MeOH as eluents at 120 mL/min) to give:

First eluted isomer example 11(a) 2-methoxy-2-[3-methoxy-5-(trifluoromethoxy)phenyl]-N-[5-[[(3R)-1-pyridazin-3-ylpyrrolidin-3-yl]amino]-1,3,4-thiadiazol-2-yl]acetamide (9.1 mg, 4.5%). $^1$H NMR (400 MHz, CDCl$_3$, 30° C.) δ2.28 (1H, dd), 2.35-2.47 (1H, m), 3.48 (3H, s), 3.56-

3.71 (2H, m), 3.73-3.83 (4H, m), 3.87 (1H, dd), 4.52 (1H, s), 4.84 (1H, s), 6.25 (1H, s), 6.56 (1H, dd), 6.71-6.76 (1H, m), 6.89-6.95 (2H, m), 7.11 (1H, dd), 8.48 (1H, dd). m/z: ES⁺ [M+H]⁺ 526.

Second eluted isomer example 11(b) 2-methoxy-2-[3-methoxy-5-(trifluoromethoxy)phenyl]-N-[5-[[(3R)-1-pyridazin-3-ylpyrrolidin-3-yl]amino]-1,3,4-thiadiazol-2-yl]acetamide (10.2 mg 5.1%). ¹H NMR (400 MHz, CDCl₃, 30° C.) δ2.20-2.31 (1H, m), 2.35-2.47 (1H, m), 3.47 (3H, s), 3.56-3.78 (3H, m), 3.80 (3H, s), 3.84-3.93 (1H, m), 4.50 (1H, s), 4.84 (1H, s), 6.14 (1H, s), 6.57 (1H, d), 6.73 (1H, s), 6.92 (2H, d), 7.12 (1H, dd), 8.49 (1H, s). m/z: ES⁺ [M+H]⁺ 526.

Example 12(a) and 12(b)

(2S)-2-Methoxy-2-[3-(3-methoxyazetidin-1-yl)phenyl]-N-[5-[[(3R)-1-(6-methylpyridazin-3-yl)pyrrolidin-3-yl]amino]-1,3,4-thiadiazol-2-yl]acetamide and (2R)-2-Methoxy-2-[3-(3-methoxyazetidin-1-yl)phenyl]-N-[5-[[(3R)-1-(6-methylpyridazin-3-yl)pyrrolidin-3-yl]amino]-1,3,4-thiadiazol-2-yl]acetamide

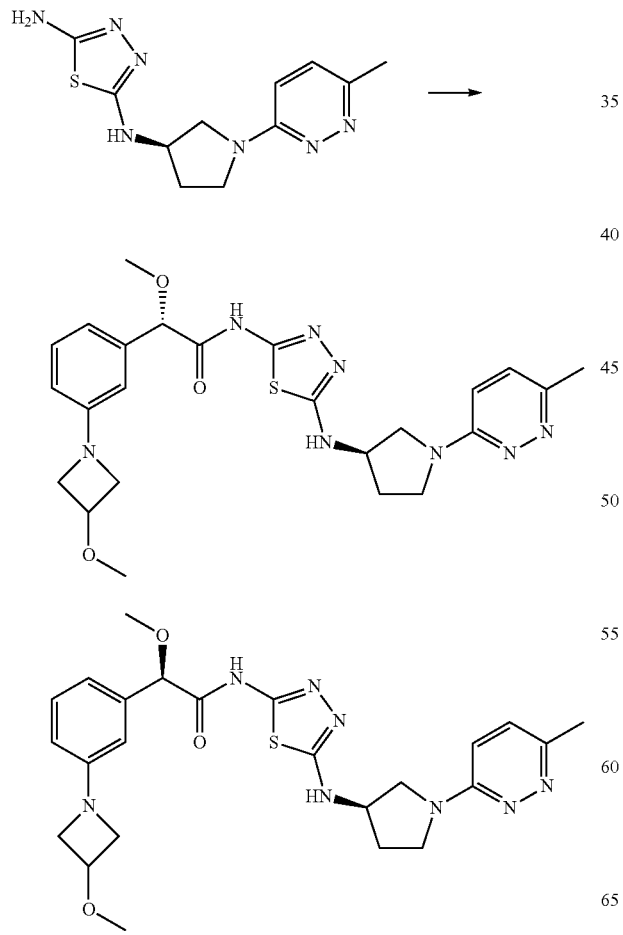

N2-[(3R)-1-(6-Methylpyridazin-3-yl)pyrrolidin-3-yl]-1,3,4-thiadiazole-2,5-diamine (Intermediate 6, 0.11 g, 0.389 mmol) and [2-methoxy-2-[3-(3-methoxyazetidin-1-yl)phenyl]acetyl]oxylithium (Intermediate 24, 0.12 g, 0.466 mmol) were dissolved in DMF (2 mL) at r.t under N₂. The mixture was stirred for 5 min before addition of DIPEA (0.34 mL, 1.943 mmol), and HATU (0.4 mL, 0.389 mmol), then at r.t. for 2 h. The crude mixture was passed through a 5 g SCX column washed with MeOH, then eluted with 2N NH₃ in MeOH. The basic fraction was evaporated and purified by preparative HPLC (SunFire C18 column, 5 m, 50 mm×19 mm at 25 mL/min). Decreasingly polar ratios of water and MeCN containing 0.1% formic acid were used as a mobile phase. Pure fractions were combined, evaporated and passed through a 1 g SCX column washed with MeOH then eluted with 2N NH₃ in MeOH to give the mixture of diastereoisomers as an off-white solid (98 mg). The diastereoisomers were separated by preparative HPLC (Lux C4 column, 20 m, 50 mm×250 mm, 100% MeOH at 120 mL/min) to give:

First eluted isomer example 12(a) 2-methoxy-2-[3-(3-methoxyazetidin-1-yl)phenyl]-N-[5-[[(3R)-1-(6-methylpyridazin-3-yl)pyrrolidin-3-yl]amino]-1,3,4-thiadiazol-2-yl]acetamide (34 mg, 18%). ¹H NMR (400 MHz, DMSO, 30° C.) 2.00-2.11 (1H, m), 2.30 (1H, dt), 2.41 (3H, s), 3.25 (3H, s), 3.45 (1H, dd), 3.49-3.62 (4H, m), 3.73 (1H, dd), 4.04 (2H, t), 4.28-4.41 (2H, m), 4.86 (1H, s), 6.40 (1H, d), 6.55 (1H, s), 6.77 (1H, d), 6.82 (1H, d), 7.15 (1H, t), 7.22 (1H, d), 7.62 (1H, d), 12.06 (1H, s); m/z: ES⁺ [M+H]⁺ 511.

Second eluted isomer example 12(b) 2-methoxy-2-[3-(3-methoxyazetidin-1-yl)phenyl]-N-[5-[[(3R)-1-(6-methylpyridazin-3-yl)pyrrolidin-3-yl]amino]-1,3,4-thiadiazol-2-yl]acetamide (38 mg, 19%). ¹H NMR (400 MHz, DMSO, 30° C.) 2.05 (1H, dt), 2.27 (1H, dt), 2.42 (3H, s), 3.25 (3H, s), 3.46 (1H, dd), 3.5-3.61 (4H, m), 3.74 (1H, dd), 4.04 (2H, t), 4.28-4.41 (2H, m), 4.85 (1H, s), 6.39 (1H, dd), 6.55 (1H, s), 6.77 (1H, d), 6.82 (1H, d), 7.15 (1H, t), 7.22 (1H, d), 7.58 (1H, d), 12.09 (1H, s). m/z: ES⁺ [M+H]⁺ 511.

Example 13(a) and 13(b)

(2S)-2-Methoxy-2-[3-(3-methoxyazetidin-1-yl)phenyl]-N-[5-[[(3R)-1-(1,2,4-triazin-3-yl)pyrrolidin-3-yl]amino]-1,3,4-thiadiazol-2-yl]acetamide and (2R)-2-Methoxy-2-[3-(3-methoxyazetidin-1-yl)phenyl]-N-[5-[[(3R)-1-(1,2,4-triazin-3-yl)pyrrolidin-3-yl]amino]-1,3,4-thiadiazol-2-yl]acetamide

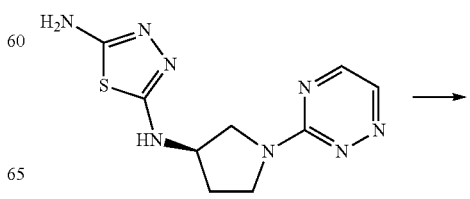

-continued

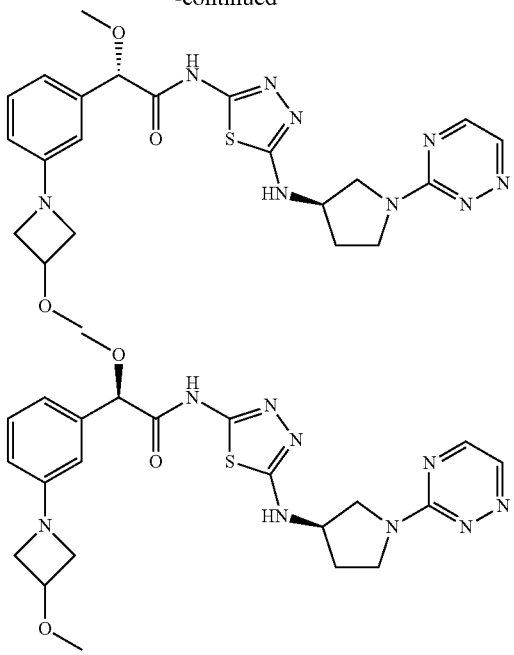

2-Methoxy-2-[3-(3-methoxyazetidin-1-yl)phenyl]acetyl] oxylithium (Intermediate 24, 0.12 g, 0.475 mmol) and N2-[(3R)-1-(1,2,4-triazin-3-yl)pyrrolidin-3-yl]-1,3,4-thiadiazole-2,5-diamine (Intermediate 12, 0.13 g, 0.475 mmol) were weighed into a round bottomed flask. DMF (3 mL) and DIPEA (0.15 g, 1.187 mmol) were added followed by HATU (0.18 g, 0.475 mmol) and the resultant solution was allowed to stir at r.t. under $N_2$ for 15 h. The reaction mixture was added to an SCX cartridge and washed with MeOH then eluted with 2M $NH_3$ in MeOH. The basic fractions were evaporated under reduced pressure and the residue purified by preparative HPLC (SunFire C18 column, 5 m, 50 mm×19 mm at 25 mL/min). Decreasingly polar ratios of water and MeCN containing 0.1% formic acid were used as a mobile phase. Fractions containing the desired mass were evaporated under reduced pressure to give the mixture of diastereoisomers as an orange gum. The diastereoisomers was separated by preparative chiral HPLC (Lux C1 column, 5 m, 21 mm×250 mm, eluent 20:80 heptane:EtOH at 21 mL/min containing 0.1% $NH_3$) to give:

First eluted isomer example 13(a) 2-methoxy-2-[3-(3-methoxyazetidin-1-yl)phenyl]-N-[5-[[(3R)-1-(1,2,4-triazin-3-yl)pyrrolidin-3-yl]amino]-1,3,4-thiadiazol-2-yl]acetamide (55.2 mg, 16.5%). $^1$H NMR (400 MHz, DMSO-d6, 30° C.) δ2.09 (1H, s), 2.30 (1H, d), 3.24 (3H, s), 3.29 (3H, s), 3.53-3.90 (6H, m), 4.03 (2H, tt), 4.27-4.42 (2H, m), 4.86 (1H, s), 6.40 (1H, ddd), 6.55 (1H, s), 6.74-6.80 (1H, m), 7.15 (1H, t), 7.70 (1H, d), 8.32 (1H, d), 8.61 (1H, d), 12.17 (1H, s). m/z: ES$^+$ [M+H]$^+$ 498.

Second eluted isomer example 13(b) 2-methoxy-2-[3-(3-methoxyazetidin-1-yl)phenyl]-N-[5-[[(3R)-1-(1,2,4-triazin-3-yl)pyrrolidin-3-yl]amino]-1,3,4-thiadiazol-2-yl]acetamide (54.2 mg, 13.7%). $^1$H NMR (400 MHz, DMSO-d6, 30° C.) δ1.98-2.08 (1H, m), 2.19-2.28 (1H, m), 3.18 (3H, s), 3.22 (3H, s), 3.47-3.84 (6H, m), 3.93-4.02 (2H, m), 4.21-4.36 (2H, m), 4.80 (1H, s), 6.34 (1H, ddd), 6.49 (1H, s), 6.67-6.74 (1H, m), 7.09 (1H, t), 7.64 (1H, d), 8.26 (1H, d), 8.55 (1H, d), 12.11 (1H, s). m/z: ES$^+$ [M+H]$^+$ 498.

Example 14(a) and 14(b)

(2S)-2-[3-(3,3-Difluoroazetidin-1-yl)phenyl]-2-methoxy-N-[5-[[(3R)-1-(1,2,4-triazin-3-yl)pyrrolidin-3-yl]amino]-1,3,4-thiadiazol-2-yl]acetamide and (2R)-2-[3-(3,3-Difluoroazetidin-1-yl)phenyl]-2-methoxy-N-[5-[[(3R)-1-(1,2,4-triazin-3-yl)pyrrolidin-3-yl]amino]-1,3,4-thiadiazol-2-yl]acetamide

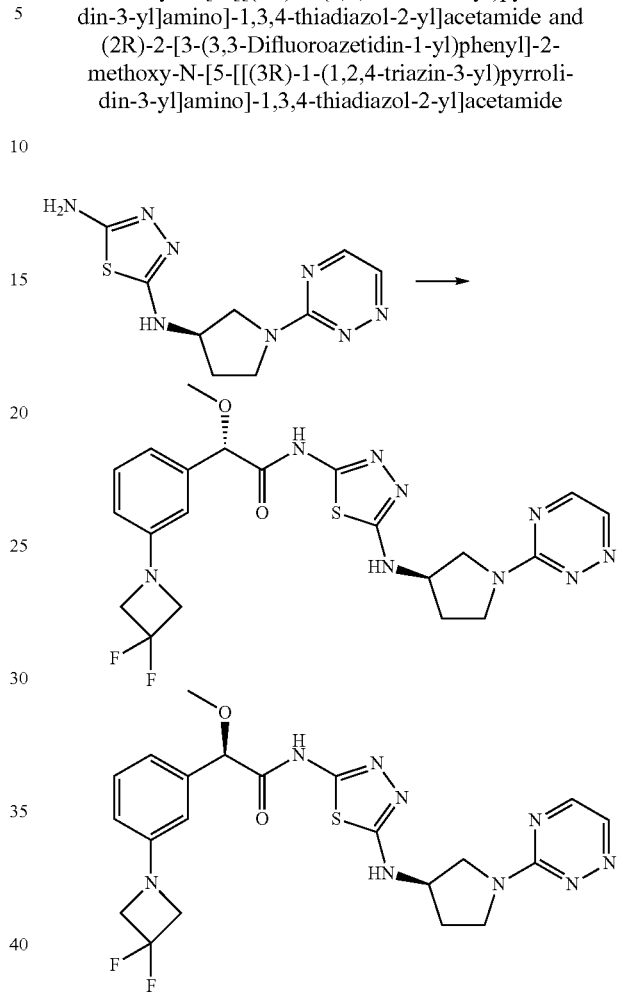

Into a round bottomed flask was weighed N2-[(3R)-1-(1,2,4-triazin-3-yl)pyrrolidin-3-yl]-1,3,4-thiadiazole-2,5-diamine (Intermediate 12, 0.06 g, 0.232 mmol), [2-[3-(3,3-difluoroazetidin-1-yl)phenyl]-2-methoxy-acetyl]oxylithium (Intermediate 21, 0.06 g, 0.232 mmol). DMF (2 mL) and DIPEA (0.1 mL, 0.579 mmol) were added followed by HATU (0.09 g, 0.232 mmol) and the resultant solution was allowed to stir at r.t. for 15 hours. The reaction mixture was added to an SCX cartridge and washed with MeOH then eluted with 2M $NH_3$ in MeOH. The basic fractions were evaporated under reduced pressure and the residue was purified by preparative HPLC (SunFire C18 column, 5 μm, 50 mm×19 mm at 25 mL/min). Decreasingly polar ratios of water and MeCN containing 0.1% formic acid were used as a mobile phase. The solvent was removed under reduced pressure to give the mixture of diastereoisomers as a cream solid. The diastereoisomers were separated by chiral preparative HPLC (Amy C column, 5 μm, 20 mm×250 mm, eluent 20:80 heptane:EtOH containing 0.1% $NH_3$ at 21 mL/min) to give:

First eluted isomer example 14(a) 2-[3-(3,3-difluoroazetidin-1-yl)phenyl]-2-methoxy-N-[5-[[(3R)-1-(1,2,4-triazin-3-yl)pyrrolidin-3-yl]amino]-1,3,4-thiadiazol-2-yl]acetamide (22.1 mg, 18.9%). $^1$H NMR (400 MHz, DMSO-d6, 30° C.)

δ2.02-2.12 (1H, m), 2.23-2.34 (1H, m), 3.29 (3H, s), 3.77 (4H, s), 4.20-4.42 (5H, m), 4.89 (1H, s), 6.49-6.57 (1H, m), 6.67 (1H, t), 6.86-6.92 (1H, m), 7.22 (1H, t), 7.67 (1H, d), 8.32 (1H, d), 8.61 (1H, d), 12.19 (1H, s). m/z: ES+ [M+H]+ 504.

Second eluted isomer example 14(b) 2-[3-(3,3-difluoroazetidin-1-yl)phenyl]-2-methoxy-N-[5-[[(3R)-1-(1,2,4-triazin-3-yl)pyrrolidin-3-yl]amino]-1,3,4-thiadiazol-2-yl]acetamide (20.8 mg, 17.8%). ¹H NMR (400 MHz, DMSO-d6, 30° C.) δ2.02-2.13 (1H, m), 2.24-2.35 (1H, m), 3.29 (3H, s), 3.77 (4H, s), 4.20-4.42 (5H, m), 4.89 (1H, s), 6.50-6.56 (1H, m), 6.65-6.69 (1H, m), 6.86-6.91 (1H, m), 7.22 (1H, t), 7.69 (1H, d), 8.31 (1H, d), 8.61 (1H, d), 12.19 (1H, s). m/z: ES+ [M+H]+ 504.

Example 15(a) and 15(b)

(2S)-2-[3-(3-Fluoroazetidin-1-yl)phenyl]-2-methoxy-N-[5-[[(3R)-1-(1,2,4-triazin-3-yl)pyrrolidin-3-yl]amino]-1,3,4-thiadiazol-2-yl]acetamide and (2R)-2-[3-(3-Fluoroazetidin-1-yl)phenyl]-2-methoxy-N-[5-[[(3R)-1-(1,2,4-triazin-3-yl)pyrrolidin-3-yl]amino]-1,3,4-thiadiazol-2-yl]acetamide

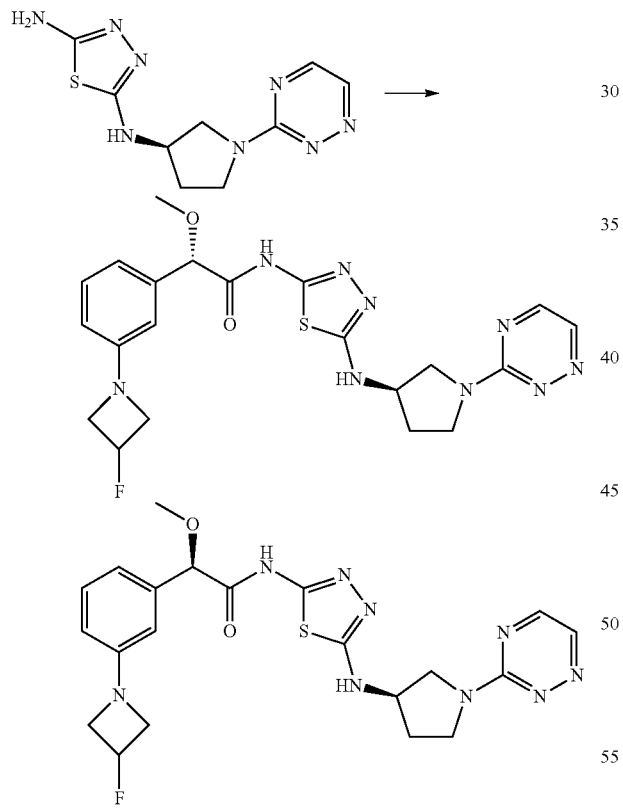

Into a round bottomed flask was weighed N2-[(3R)-1-(1,2,4-triazin-3-yl)pyrrolidin-3-yl]-1,3,4-thiadiazole-2,5-diamine (Intermediate 12, 0.05 g, 0.17 mmol), [2-[3-(3-fluoroazetidin-1-yl)phenyl]-2-methoxy-acetyl]oxylithium (Intermediate 17, 0.04 g, 0.17 mmol). DMF (2 mL) and HATU (0.06 g, 0.17 mmol) were added followed by DIPEA (0.07 mL, 0.426 mmol) and the resultant solution was allowed to stir at r.t. for 15 h. The reaction mixture was added to an SCX cartridge and washed with MeOH then eluted with 2M NH₃ in MeOH. The basic fractions were evaporated under reduced pressure and the residue was purified by preparative HPLC (SunFire C18 column, 5 m, 50 mm×19 mm at 25 mL/min). Decreasingly polar ratios of water and MeCN containing 0.1% formic acid were used as a mobile phase. The solvent was removed under reduced pressure to give the mixture of diastereoisomers as a cream solid. The diastereoisomers was separated by preparative chiral HPLC (Amy-C column, 5 m, 20 mm×250 mm, eluent 20:80 heptane:EtOH at 21 mL/min containing 0.1% NH₃) to give:

First eluted isomer example 15(a) 2-[3-(3-fluoroazetidin-1-yl)phenyl]-2-methoxy-N-[5-[[(3R)-1-(1,2,4-triazin-3-yl)pyrrolidin-3-yl]amino]-1,3,4-thiadiazol-2-yl]acetamide (17.9 mg, 21.7%). ¹H NMR (400 MHz, DMSO-d6, 30° C.) δ2.04-2.13 (1H, m), 2.23-2.35 (1H, m), 3.28 (3H, s), 3.47-3.94 (6H, m), 4.06-4.20 (2H, m), 4.35 (1H, s), 4.84 (1H, s), 5.55 (1H, tt), 6.39-6.46 (1H, m), 6.58 (1H, t), 6.80 (1H, dt), 7.16 (1H, t), 7.62 (1H, s), 8.31 (1H, d), 8.60 (1H, d), 12.18 (1H, s). m/z: ES+ [M+H]+ 486.

Second eluted isomer example 15(b) 2-[3-(3-fluoroazetidin-1-yl)phenyl]-2-methoxy-N-[5-[[(3R)-1-(1,2,4-triazin-3-yl)pyrrolidin-3-yl]amino]-1,3,4-thiadiazol-2-yl]acetamide (19 mg, 23%). ¹H NMR (400 MHz, DMSO-d6, 30° C.) δ2.03-2.13 (1H, m), 2.23-2.34 (1H, m), 3.28 (s, 3H), 3.50-3.93 (6H, m), 4.08-4.21 (2H, m), 4.36 (1H, s), 4.87 (1H, s), 5.38-5.58 (1H, m), 6.41-6.46 (1H, m), 6.58 (1H, t), 6.77-6.83 (1H, m), 7.17 (1H, t), 7.68 (1H, d), 8.32 (1H, d), 8.61 (1H, d), 12.18 (1H, s). m/z: ES+ [M+H]+ 486.

Example 16(a) and 16(b)

(2S)-2-(3,5-Dimethoxyphenyl)-2-methoxy-N-[5-[[(3R)-1-(1,2,4-triazin-3-yl)pyrrolidin-3-yl]amino]-1,3,4-thiadiazol-2-yl]acetamide and (2R)-2-(3,5-Dimethoxyphenyl)-2-methoxy-N-[5-[[(3R)-1-(1,2,4-triazin-3-yl)pyrrolidin-3-yl]amino]-1,3,4-thiadiazol-2-yl]acetamide

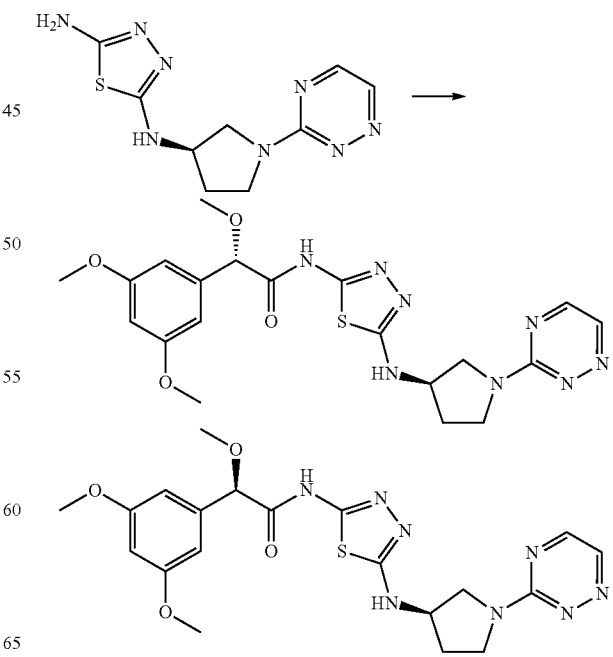

DIPEA (0.1 mL, 0.568 mmol) was added to 2-(3,5-dimethoxyphenyl)-2-methoxy-acetic acid (Intermediate 28, 0.13 g, 0.568 mmol) and N2-[(3R)-1-(1,2,4-triazin-3-yl)pyrrolidin-3-yl]-1,3,4-thiadiazole-2,5-diamine (Intermediate 12, 0.15 g, 0.568 mmol) in DMF (3 mL). HATU (0.22 g, 0.568 mmol) was added to the solution and the reaction mixture was allowed to stir at room temperature under nitrogen for 24 h. The solvent was removed under reduced pressure to provide a dark orange oil which was dissolved in DCM, absorbed onto silica and purified by FCC (SiO₂, 1-10% MeOH in DCM). The pure fractions were combined and solvent was removed under reduced pressure to provide a dark orange oil which was further purified by preparative HPLC (SunFire C18 column, 5 m, 50 mm×19 mm, flow rate 25 mL/min). Decreasingly polar ratios of water and MeCN containing 0.1% formic acid were used as a mobile phase. Pure fractions were combined, evaporated under reduced pressure and passed through a 2 g SCX column washed with MeOH then eluted with 2N NH₃ in MeOH. The basic fraction was evaporated to dryness to afford the mixture of diastereoisomers as an off-white foam (132 mg). The diastereoisomers were separated by preparative HPLC (Lux C4 column, 5 μm, 20 mm×250 mm, eluent MeOH containing diethanolamine modifier at 21 mL/min). The separate diastereoisomers were dissolved in DCM, washed with water and the organic layer evaporated to give:

First eluted isomer example 16(a) 2-(3,5-dimethoxyphenyl)-2-methoxy-N-[5-[[(3R)-1-(1,2,4-triazin-3-yl)pyrrolidin-3-yl]amino]-1,3,4-thiadiazol-2-yl]acetamide (23.2 mg, 8.6%). $^1$H NMR (400 MHz, DMSO-d6, 21° C.) δ2.09 (1H, d) 2.30 (1H, dd), 3.30 (3H, d), 3.74 (6H, s), 3.55-3.91 (4H, m), 4.38 (1H, s), 4.89 (1H, s), 6.47 (1H, t), 6.64 (2H, d), 7.71 (1H, d), 8.32 (1H, d), 8.61 (1H, d), 12.17 (1H, s). m/z: ES⁺ [M+H]⁺ 472.

Second eluted isomer example 16(b) 2-(3,5-dimethoxyphenyl)-2-methoxy-N-[5-[[(3R)-1-(1,2,4-triazin-3-yl)pyrrolidin-3-yl]amino]-1,3,4-thiadiazol-2-yl]acetamide (28.3 mg, 10.5%). $^1$H NMR (400 MHz, DMSO-d6, 21° C.) δ2.12 (1H, s), 2.31 (1H, d), 3.33 (3H, s), 3.60-3.73 (3H, m), 3.77 (6H, s), 3.80-3.89 (1H, m), 4.40 (1H, s), 4.92 (1H, s), 6.50 (1H, t), 6.67 (2H, d), 7.73 (1H, d), 8.35 (1H, d), 8.64 (1H, d), 12.19 (1H, s). m/z: ES⁺ [M+H]⁺ 472.

Example 17(a) and 17(b)

(2S)-[3-(Difluoromethoxy)phenyl]-2-ethoxy-N-[5-[[(3R)-1-pyridazin-3-ylpyrrolidin-3-yl]amino]-1,3,4-thiadiazol-2-yl]acetamide and (2R)-[3-(Difluoromethoxy)phenyl]-2-ethoxy-N-[5-[[(3R)-1-pyridazin-3-ylpyrrolidin-3-yl]amino]-1,3,4-thiadiazol-2-yl]acetamide

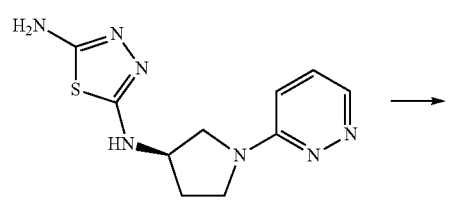

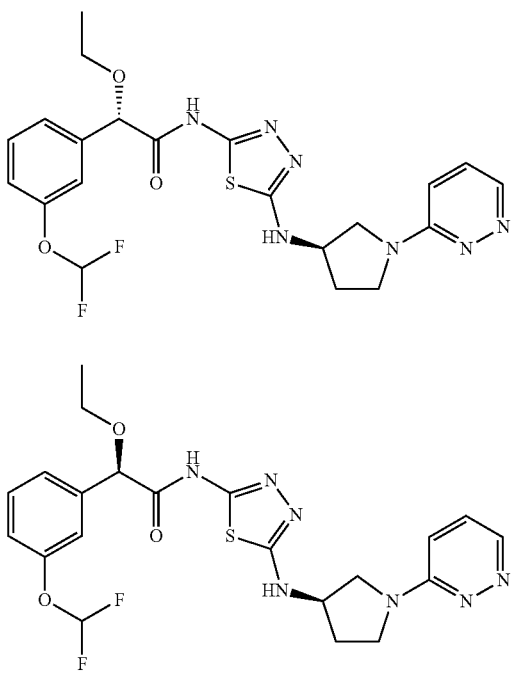

2-[3-(Difluoromethoxy)phenyl]-2-ethoxy-acetic acid (Intermediate 47, 0.14 g, 0.57 mmol) and N2-[(3R)-1-pyridazin-3-ylpyrrolidin-3-yl]-1,3,4-thiadiazole-2,5-diamine (Intermediate 1, 0.15 g, 0.57 mmol) were weighed into a round bottomed flask. DMF (3 mL) and DIPEA (0.18 g, 1.424 mmol) were added followed by HATU (0.22 g, 0.57 mmol) and the resultant solution was allowed to stir at r.t. under N₂ for 3 h. The solvent was removed under reduced pressure. The residual gum was dissolved in DCM, absorbed onto silica and purified by FCC (SiO₂, 1 to 8% MeOH in DCM). Evaporation of the pure fractions under reduced pressure gave a yellow gum that was separated by preparative chiral SFC (Amy-C column, 5 μm, 20 mm×250 mm, eluent MeOH/CO₂ containing 40% NH₃ as a modifier. The flow rate was 50 mL/min at a wavelength of 210 nm) to give:

First eluted isomer example 17(a) [3-(difluoromethoxy)phenyl]-2-ethoxy-N-[5-[[(3R)-1-pyridazin-3-ylpyrrolidin-3-yl]amino]-1,3,4-thiadiazol-2-yl]acetamide (23 mg, 8.2%). $^1$H NMR (400 MHz, DMSO-d6, 30° C.) δ1.19 (3H, t), 2.02-2.10 (1H, m), 2.21-2.36 (1H, m), 3.37-3.63 (5H, m), 3.74 (1H, dd), 4.40-4.36 (1H, m), 5.12 (1H, s), 6.87 (1H, dd), 7.16 (1H, dd), 7.25 (1H, t), 7.28-7.29 (1H, m), 7.30-7.38 (2H, m), 7.45 (1H, t), 7.72 (1H, d), 8.48 (1H, dd), 12.27 (1H, s). m/z: ES⁺ [M+H]⁺ 492.

Second eluted isomer example 17(b) [3-(difluoromethoxy)phenyl]-2-ethoxy-N-[5-[[(3R)-1-pyridazin-3-ylpyrrolidin-3-yl]amino]-1,3,4-thiadiazol-2-yl]acetamide (0.025 g, 8.9%). $^1$H NMR (400 MHz, DMSO-d₆, 30° C.) δ$^1$H NMR (400 MHz, DMSO-d6) δ 1.19 (3H, t), 2.03-2.10 (1H, m), 2.24-2.32 (1H, m), 3.38-3.62 (5H, m), 3.74 (1H, dd), 4.36-4.40 (1H, m), 5.12 (1H, s), 6.86 (1H, dd), 7.16 (1H, t), 7.24 (1H, t), 7.26-7.38 (3H, m), 7.45 (1H, t), 7.72 (1H, d), 8.48 (1H, dd), 12.27 (1H, s). m/z: ES⁺ [M+H]⁺ 492.

Example 18(a) and 18(b)

(2S)-2-Methoxy-2-[3-(oxetan-3-yl)phenyl]-N-[5-[[(3R)-1-pyridazin-3-ylpyrrolidin-3-yl]amino]-1,3,4-thiadiazol-2-yl]acetamide and (2R)-2-Methoxy-2-[3-(oxetan-3-yl)phenyl]-N-[5-[[(3R)-1-pyridazin-3-ylpyrrolidin-3-yl]amino]-1,3,4-thiadiazol-2-yl]acetamide

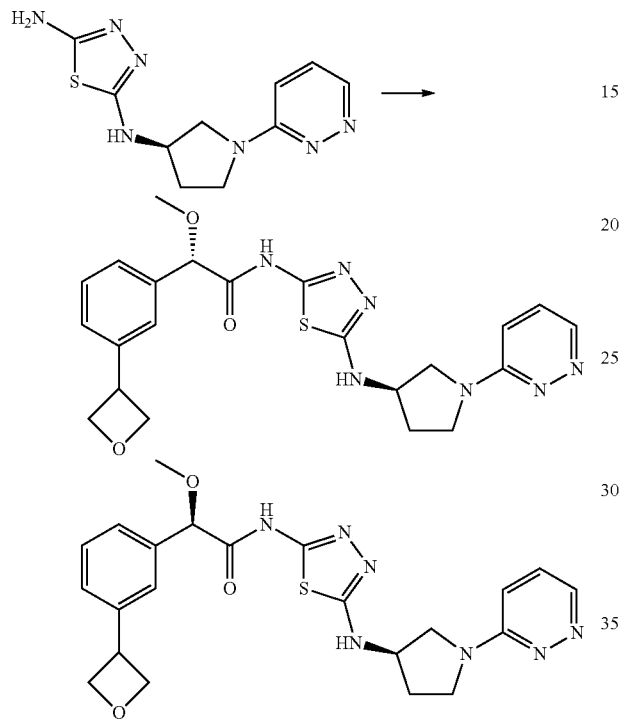

HATU (520 mg, 1.37 mmol) was added to N2-[(3R)-1-pyridazin-3-ylpyrrolidin-3-yl]-1,3,4-thiadiazole-2,5-diamine (Intermediate 1, 300 mg, 1.14 mmol), 2-methoxy-2-[3-(oxetan-3-yl)phenyl]acetic acid (Intermediate 48, 304 mg, 1.37 mmol) and DIPEA (0.198 mL, 1.14 mmol) in DMF (8 mL) at 21° C. under N$_2$. The resulting solution was stirred at 21° C. for 2 hours. The crude product was purified by ion exchange chromatography, using an SCX column. The desired product was eluted from the column using 1M NH$_3$ in MeOH and pure fractions were evaporated. The crude product was purified by FCC (SiO$_2$, 0 to 15% 1M NH$_3$ in MeOH in EtOAc). Pure fractions were evaporated to dryness to afford a solid. The crude product was purified by preparative HPLC (Waters XBridge OBD C18 column, 5 μm, 30 mm×100 mm). Decreasingly polar mixtures of water containing 1% NH$_4$OH and MeCN were used as the mobile phase. Fractions containing the desired compound were evaporated to dryness to yield the product as a mixture of diastereoisomers. The diastereoisomers were separated by preparative HPLC (Phenomenex Lux C4 column, 20 μm, 50 mm×250 mm, MeOH/IPA 50/50 at 120 mL/min) to give:

First eluted isomer example 18(a) 2-methoxy-2-[3-(oxetan-3-yl)phenyl]-N-[5-[[(3R)-1-pyridazin-3-ylpyrrolidin-3-yl]amino]-1,3,4-thiadiazol-2-yl]acetamide (45 mg, 8%). $^1$H NMR (400 MHz, DMSO, 30° C.) δ2.12 (1H, td), 2.23-2.40 (1H, m), 3.38 (3H, s), 3.46-3.69 (3H, m), 3.74-3.86 (1H, m), 4.26-4.35 (1H, m), 4.41-4.50 (1H, m), 4.65 (2H, ddd), 4.90-5.11 (3H, m), 6.91 (1H, dd), 7.27-7.49 (4H, m), 7.57 (1H, s), 7.70 (1H, d), 8.53 (1H, dd), 12.24 (1H, s). m/z: ES$^+$ [M+H]$^+$ 468.

Second eluted isomer example 18(b) 2-methoxy-2-[3-(oxetan-3-yl)phenyl]-N-[5-[[(3R)-1-pyridazin-3-ylpyrrolidin-3-yl]amino]-1,3,4-thiadiazol-2-yl]acetamide (38 mg, 7%). $^1$H NMR (400 MHz, DMSO, 30° C.) δ2.12 (1H, td), 2.23-2.40 (1H, m), 3.38 (3H, s), 3.46-3.69 (3H, m), 3.74-3.86 (1H, m), 4.26-4.35 (1H, m), 4.41-4.50 (1H, m), 4.65 (2H, ddd), 4.90-5.11 (3H, m), 6.91 (1H, dd), 7.27-7.49 (4H, m), 7.57 (1H, s), 7.70 (1H, d), 8.53 (1H, dd), 12.24 (1H, s). m/z: ES$^+$ [M+H]$^+$ 468.

Example 19(a) and 19(b)

(2S)-2-Ethoxy-N-[5-[[(3R)-1-pyridazin-3-ylpyrrolidin-3-yl]amino]-1,3,4-thiadiazol-2-yl]-2-[3-(trifluoromethoxy)phenyl]acetamide and (2R)-2-Ethoxy-N-[5-[[(3R)-1-pyridazin-3-ylpyrrolidin-3-yl]amino]-1,3,4-thiadiazol-2-yl]-2-[3-(trifluoromethoxy)phenyl]acetamide

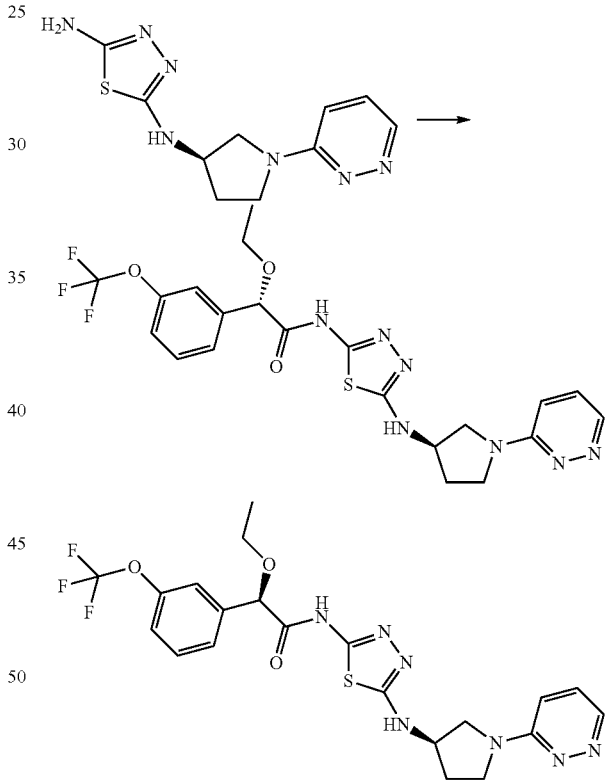

DIPEA (0.15 mL, 0.85 mmol), HATU (260 mg, 0.68 mmol) and 2-ethoxy-2-[3-(trifluoromethoxy)phenyl]acetic acid (Intermediate 51, 180 mg, 0.68 mmol) were added to a solution of N2-[(3R)-1-pyridazin-3-ylpyrrolidin-3-yl]-1,3,4-thiadiazole-2,5-diamine (Intermediate 1, 150 mg, 0.57 mmol) in DMF (4 mL). The mixture was stirred at r.t. for 18 h. This was then diluted with water (5 mL) and then extracted into DCM (10 mL), evaporated and purified by preparative HPLC (XBridge OBD C18 column, 5 m, 50 mm×19 mm, flow rate was 25 mL/min). Decreasingly polar ratios of water and MeCN containing 0.3 mL/L NH$_4$OH were used as a mobile phase. Pure fractions were evaporated and passed through an SCX cartridge washing with MeOH and then eluting with 2M NH₃ in MeOH. The basic fraction was evaporated and dried in vacuo to give the product as a mixture of diastereoisomers. The diastereoisomers were then separated by HPLC (Lux C4 column, 5 μm, 20 mm×250 mm, MeOH containing NH₃ modifier, 21 mL/min) to give:

First eluted isomer example 19(a) 2-ethoxy-N-[5-[[(3R)-1-pyridazin-3-ylpyrrolidin-3-yl]amino]-1,3,4-thiadiazol-2-yl]-2-[3-(trifluoromethoxy)phenyl]acetamide, (46 mg, 16%). ¹H NMR (400 MHz, DMSO-d6, 21° C.) δ1.19 (3H, t), 1.97-2.15 (1H, m), 2.18-2.36 (1H, m), 3.40-3.65 (5H, m), 3.65-3.81 (1H, m), 4.32-4.46 (1H, m), 5.17 (1H, s), 6.87 (1H, dd), 7.28-7.40 (2H, m), 7.40-7.59 (3H, m), 7.74 (1H, d), 8.48 (1H, dd), 12.32 (1H, s). m/z: ES⁺[M+H]⁺ 510.

Second eluted isomer example 19(b) 2-ethoxy-N-[5-[[(3R)-1-pyridazin-3-ylpyrrolidin-3-yl]amino]-1,3,4-thiadiazol-2-yl]-2-[3-(trifluoromethoxy)phenyl]acetamide (39 mg, 14%). ¹H NMR (400 MHz, DMSO-d6, 21° C.) δ1.19 (3H, t), 2.06 (1H, m), 2.20-2.35 (1H, m), 3.39-3.63 (5H, m), 3.74 (1H, m), 4.34-4.44 (1H, m), 5.17 (1H, s), 6.88 (1H, dd), 7.28-7.41 (2H, m), 7.42-7.58 (3H, m), 7.73 (1H, d), 8.48 (1H, d), 12.32 (1H, s). m/z: ES⁺[M+H]⁺ 510.

Example 20(a) and 20(b)

(2R)-2-[4-Fluoro-3-(trifluoromethoxy)phenyl]-2-methoxy-N-[5-[[(3R)-1-pyridazin-3-ylpyrrolidin-3-yl]amino]-1,3,4-thiadiazol-2-yl]acetamide and (2S)-2-[4-Fluoro-3-(trifluoromethoxy)phenyl]-2-methoxy-N-[5-[[(3R)-1-pyridazin-3-ylpyrrolidin-3-yl]amino]-1,3,4-thiadiazol-2-yl]acetamide

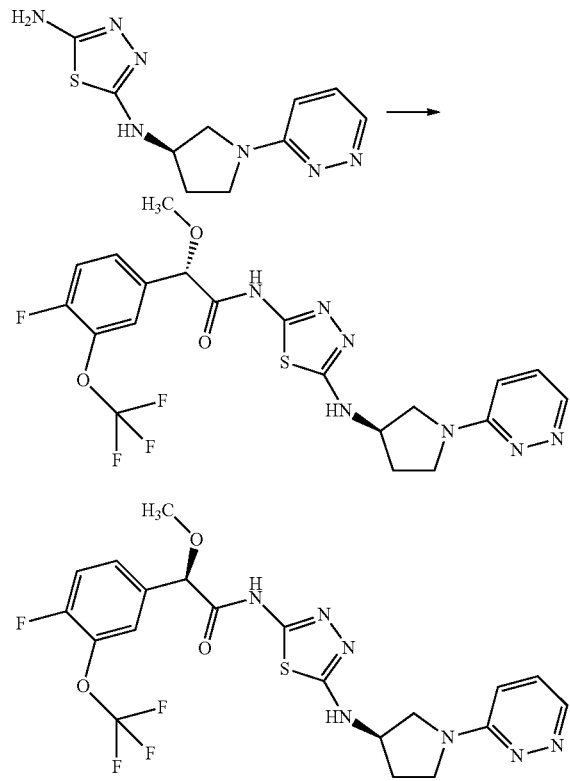

DIPEA (0.12 mL, 0.71 mmol), HATU (216 mg, 0.568 mmol) and 2-[4-fluoro-3-(trifluoromethoxy)phenyl]-2-methoxy-acetic acid (Intermediate 52, 0.13 g, 0.474 mmol) were added to a solution of N2-[(3R)-1-pyridazin-3-ylpyrrolidin-3-yl]-1,3,4-thiadiazole-2,5-diamine (Intermediate 1, 0.12 g, 0.474 mmol) in DMF (4 mL). The mixture was stirred at r.t. for 18 h. This was then diluted with water (5 mL), extracted into DCM (10 mL), evaporated and purified by preparative HPLC (SunFire C18 column, 5 m, 50 mm×19 mm at 25 mL/min). Decreasingly polar ratios of water and MeCN containing 0.1% formic acid were used as a mobile phase. Pure fractions were passed down an SCX cartridge washing with MeOH and then eluting with 2M NH₃ in MeOH. The basic fraction was evaporated. An impurity was still seen so the material was re-purified by preparative HPLC (XBridge OBD C18 column, 5 μm, 50 mm×19 mm, flow rate 25 mL/min). Decreasingly polar ratios of water and MeCN containing 0.3 mL/L NH₄OH were used as a mobile phase. Pure fractions were evaporated to dryness and the mixture of diastereoisomers was separated by preparative chiral HPLC (Phenomenex Lux C2 column, 20 μm, 50 mm×250 mm, eluent MeOH at 110 mL/min) to give:

First eluted isomer example 20(a) 2-[4-Fluoro-3-(trifluoromethoxy)phenyl]-2-methoxy-N-[5-[[(3R)-1-pyridazin-3-ylpyrrolidin-3-yl]amino]-1,3,4-thiadiazol-2-yl]acetamide (18.4 mg, 7.5%). ¹H NMR (400 MHz, DMSO-d6, 22° C.) 2.06 (1H, dq), 2.28 (1H, dt), 3.34 (3H, s), 3.45-3.60 (3H, m), 3.75 (1H, dd), 4.34-4.42 (1H, m), 5.03 (1H, s), 6.87 (1H, dd), 7.33 (1H, dd), 7.51-7.57 (2H, m), 7.60-7.69 (2H, m), 8.48 (1H, dd), 12.35 (1H, s). m/z: ES+ [M+H]+ 514.

Second eluted isomer example 20(b) 2-[4-Fluoro-3-(trifluoromethoxy)phenyl]-2-methoxy-N-[5-[[(3R)-1-pyridazin-3-ylpyrrolidin-3-yl]amino]-1,3,4-thiadiazol-2-yl]acetamide (19.2 mg, 7.9%). ¹H NMR (400 MHz, DMSO-d6, 22° C.) 2.07 (1H, dd), 2.28 (1H, dt), 3.49 (1H, d), 3.53-3.60 (2H, m), 3.74 (1H, dd), 4.33-4.43 (1H, m), 5.04 (1H, s), 6.87 (1H, d), 7.33 (1H, dd), 7.52-7.57 (2H, m), 7.63 (1H, d), 7.68 (1H, d), 8.48 (1H, d), 12.35 (1H, s). m/z: ES⁺ [M+H]⁺514.

Example 21(a) and 21(b)

(2S)-2-(3,5-Dimethoxyphenyl)-2-methoxy-N-[5-[[(3R)-1-pyridazin-3-ylpyrrolidin-3-yl]amino]-1,3,4-thiadiazol-2-yl]acetamide and (2R)-2-(3,5-Dimethoxyphenyl)-2-methoxy-N-[5-[[(3R)-1-pyridazin-3-ylpyrrolidin-3-yl]amino]-1,3,4-thiadiazol-2-yl]acetamide

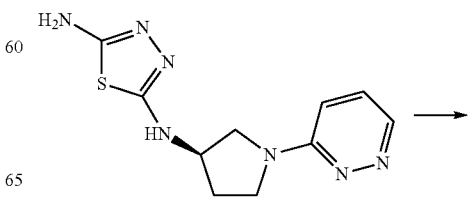

39
-continued

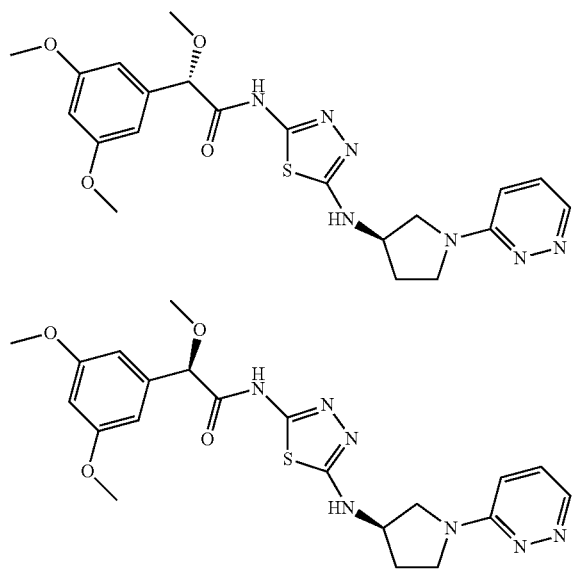

HATU (433 mg, 1.14 mmol) was added to 2-(3,5-dimethoxyphenyl)-2-methoxy-acetic acid (Intermediate 28, 215 mg, 0.95 mmol), N2-[(3R)-1-pyridazin-3-ylpyrrolidin-3-yl]-1,3,4-thiadiazole-2,5-diamine (Intermediate 1, 250 mg, 0.95 mmol) and DIPEA (0.332 mL, 1.90 mmol) in DMF (8 mL) at 21° C. under nitrogen. The resulting solution was stirred at 21° C. for 2 hours. The crude product was purified by ion exchange chromatography, using an SCX column. The desired product was eluted from the column using 1M $NH_3$/MeOH and pure fractions were evaporated to dryness to afford crude product. The crude product was purified by flash silica chromatography, (elution gradient 0 to 12% 1M $NH_3$/MeOH in DCM). Pure fractions were evaporated to dryness to afford a beige foam. LCMS showed a 9% chemical impurity. The crude product was further purified by flash silica chromatography, (elution gradient 0 to 8% MeOH in DCM). Pure fractions were evaporated to dryness to afford the product as a mixture of diastereoisomers. (180 mg)

The diastereoisomers were separated by preparative HPLC (Luc C4 column, 20 m silica, 50 mm diameter, 250 mm length, 100% MeOH at 120 ml/min). The separate diastereoisomers were dissolved in DCM, washed with water and the organic layer evaporated to give:

Example 21(a) as the first eluted isomer (solid, 74 mg, 16%). $^1$H NMR (400 MHz, DMSO, 27° C.) δ2.06 (1H, m), 2.21-2.38 (1H, m), 3.30 (9H, d), 3.41-3.62 (3H, m), 4.28-4.47 (1H, m), 4.87 (1H, s), 6.46 (1H, t), 6.63 (2H, s), 6.85 (1H, d), 7.31 (1H, dd), 7.65 (1H, d), 8.47 (1H, dd), 12.13 (1H, s). m/z: ES$^+$ [M+H]$^+$ 472.

Example 21(b) as the second eluted isomer (solid, 75 mg, 17%). $^1$H NMR (400 MHz, DMSO, 27° C.) δ2.06 (1H, m), 2.21-2.38 (1H, m), 3.30 (9H, d), 3.41-3.62 (3H, m), 4.28-4.47 (1H, m), 4.87 (1H, s), 6.46 (1H, t), 6.63 (2H, s), 6.85 (1H, d), 7.31 (1H, dd), 7.65 (1H, d), 8.47 (1H, dd), 12.13 (1H, s). m/z: ES$^+$ [M+H]$^+$ 472.

40

Example 22(a) and 22(b)

(2S)-2-ethoxy-2-[3-(3-methoxyazetidin-1-yl)phenyl]-N-[5-[[(3R)-1-pyridazin-3-ylpyrrolidin-3-yl]amino]-1,3,4-thiadiazol-2-yl]acetamide and (2R)-2-ethoxy-2-[3-(3-methoxyazetidin-1-yl)phenyl]-N-[5-[[(3R)-1-pyridazin-3-ylpyrrolidin-3-yl]amino]-1,3,4-thiadiazol-2-yl]acetamide

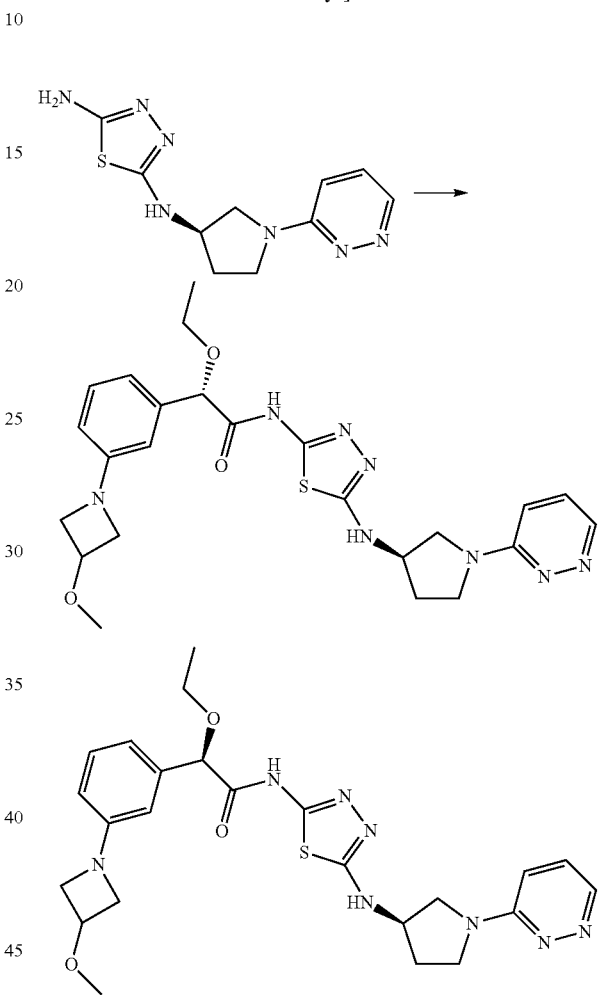

HATU (0.13 g, 0.332 mmol) and N2-[(3R)-1-pyridazin-3-ylpyrrolidin-3-yl]-1,3,4-thiadiazole-2,5-diamine (Intermediate 1, 0.07 g, 0.276 mmol) were dissolved in DMF (2 mL) at r.t under $N_2$. The mixture was stirred for 5 min before addition of DIPEA (0.07 mL, 0.414 mmol) and lithium 2-ethoxy-2-[3-(3-methoxyazetidin-1-yl)phenyl]acetate (Intermediate 56, 0.07 g, 0.276 mmol) then allowed to stir at r.t. overnight. The crude mixture was passed through a 5 g SCX column washed with MeOH then eluted with 2N $NH_3$ in MeOH. The basic fraction was evaporated to give the impure product as an orange gum which was purified by preparative HPLC (SunFire C18 column, 5 m, 50 mm×19 mm at 25 mL/min). Decreasingly polar ratios of water and MeCN containing 0.1% formic acid were used as a mobile phase. Fractions containing the desired mass were combined, evaporated and passed through a 5 g SCX column, washing with MeOH, then eluting with 2N $NH_3$ in MeOH. The solvent was removed in vacuo to give a mixture of diastereoisomers which were separated by preparative chiral HPLC. (Phenomenex Lux C4 column, 20 m silica, 50 mm diameter, 250 mm length), EtOH/MeOH 50/50 at 120 mL/min. Fractions containing the desired compounds were evaporated to dryness to give:

Example 22(a) as the first eluted isomer (solid, 21.4 mg, 15%).

Example 22(b) as the second eluted isomer (solid, 20.4 mg, 14%).

Additional Examples

The compounds of the following Examples were prepared in a similar fashion to the Examples above.

| Example no. | Name | MS data |
|---|---|---|
| 23 | 2-(3,5-dimethoxyphenyl)-2-methoxy-N-[5-[[(3R)-1-pyridazin-3-ylpyrrolidin-3-yl]amino]-1,3,4-thiadiazol-2-yl]acetamide | m/z: ES+ [M + H]+ 472 |
| 24 | 2-methoxy-2-[3-(oxetan-3-yl)phenyl]-N-[5-[[(3R)-1-(1,2,4-triazin-3-yl)pyrrolidin-3-yl]amino]-1,3,4-thiadiazol-2-yl]acetamide | m/z (ES+), [M + H]+ = 469 |
| 25 | 2-methoxy-2-[3-(oxetan-3-yl)phenyl]-N-[5-[[(3R)-1-(1,2,4-triazin-3-yl)pyrrolidin-3-yl]amino]-1,3,4-thiadiazol-2-yl]acetamide | m/z (ES+), [M + H]+ = 469 |
| 26 | 2-(3,5-dimethoxyphenyl)-N-[5-[[(3R)-1-(6-fluoropyridazin-3-yl)pyrrolidin-3-yl]amino]-1,3,4-thiadiazol-2-yl]-2-methoxy-acetamide | m/z (ES+), [M + H]+ = 490 |
| 27 | 2-[3-(3-fluoroazetidin-1-yl)phenyl]-N-[5-[[(3R)-1-(6-fluoropyridazin-3-yl)pyrrolidin-3-yl]amino]-1,3,4-thiadiazol-2-yl]-2-methoxy-acetamide | m/z: ES+ [M + H]+ 503 |
| 28 | 2-[3-(3-fluoroazetidin-1-yl)phenyl]-N-[5-[[(3R)-1-(6-fluoropyridazin-3-yl)pyrrolidin-3-yl]amino]-1,3,4-thiadiazol-2-yl]-2-methoxy-acetamide | m/z: ES+ [M + H]+ 503 |
| 29 | 2-[3-(3,3-difluoroazetidin-1-yl)phenyl]-2-ethoxy-N-[5-[[(3R)-1-pyridazin-3-ylpyrrolidin-3-yl]amino]-1,3,4-thiadiazol-2-yl]acetamide | m/z: ES+ [M + H]+ 517 |
| 30 | 2-[3-(3,3-difluoroazetidin-1-yl)phenyl]-2-ethoxy-N-[5-[[(3R)-1-pyridazin-3-ylpyrrolidin-3-yl]amino]-1,3,4-thiadiazol-2-yl]acetamide | m/z: ES+ [M + H]+ 517 |
| 31 | 2-ethoxy-2-[3-(3-fluoroazetidin-1-yl)phenyl]-N-[5-[[(3R)-1-pyridazin-3-ylpyrrolidin-3-yl]amino]-1,3,4-thiadiazol-2-yl]acetamide | m/z: ES+ [M + H]+ 499 |
| 32 | 2-ethoxy-2-[3-(3-fluoroazetidin-1-yl)phenyl]-N-[5-[[(3R)-1-pyridazin-3-ylpyrrolidin-3-yl]amino]-1,3,4-thiadiazol-2-yl]acetamide | m/z: ES+ [M + H]+ 499 |
| 33 | 2-ethoxy-2-[3-(3-methoxyazetidin-1-yl)phenyl]-N-[5-[[(3R)-1-pyridazin-3-ylpyrrolidin-3-yl]amino]-1,3,4-thiadiazol-2-yl]acetamide | m/z: ES+ [M + H]+ 511 |
| 34 | 2-ethoxy-2-[3-(3-methoxyazetidin-1-yl)phenyl]-N-[5-[[(3R)-1-pyridazin-3-ylpyrrolidin-3-yl]amino]-1,3,4-thiadiazol-2-yl]acetamide | m/z: ES+ [M + H]+ 511 |
| 35 | 2-[3-(3-fluoroazetidin-1-yl)phenyl]-2-methoxy-N-[5-[[(3R)-1-(6-methylpyridazin-3-yl)pyrrolidin-3-yl]amino]-1,3,4-thiadiazol-2-yl]acetamide | m/z: ES+ [M + H]+ 499 |
| 36 | 2-[3-(3-fluoroazetidin-1-yl)phenyl]-2-methoxy-N-[5-[[(3R)-1-(6-methylpyridazin-3-yl)pyrrolidin-3-yl]amino]-1,3,4-thiadiazol-2-yl]acetamide | m/z: ES+ [M + H]+ 499 |
| 37 | 2-[3-(3,3-difluoroazetidin-1-yl)-4-fluoro-phenyl]-2-methoxy-N-[5-[[(3R)-1-pyridazin-3-ylpyrrolidin-3-yl]amino]-1,3,4-thiadiazol-2-yl]acetamide | m/z: ES+ [M + H]+ 521 |
| 38 | 2-[3-(3,3-difluoroazetidin-1-yl)-4-fluoro-phenyl]-2-methoxy-N-[5-[[(3R)-1-pyridazin-3-ylpyrrolidin-3-yl]amino]-1,3,4-thiadiazol-2-yl]acetamide | m/z: ES+ [M + H]+ 521 |
| 39 | 2-[3-(3,3-difluoroazetidin-1-yl)phenyl]-2-methoxy-N-[5-[[(3R)-1-(6-methylpyridazin-3-yl)pyrrolidin-3-yl]amino]-1,3,4-thiadiazol-2-yl]acetamide | m/z: ES+ [M + H]+ 517 |
| 40 | 2-[3-(3,3-difluoroazetidin-1-yl)phenyl]-2-methoxy-N-[5-[[(3R)-1-(6-methylpyridazin-3-yl)pyrrolidin-3-yl]amino]-1,3,4-thiadiazol-2-yl]acetamide | m/z: ES+ [M + H]+ 517 |
| 41 | 2-[3-(3,3-difluoroazetidin-1-yl)phenyl]-N-[5-[[(3R)-1-(6-fluoropyridazin-3-yl)pyrrolidin-3-yl]amino]-1,3,4-thiadiazol-2-yl]-2-methoxy-acetamide | m/z: ES+ [M + H]+ 521 |
| 42 | 2-[3-(3,3-difluoroazetidin-1-yl)phenyl]-N-[5-[[(3R)-1-(6-fluoropyridazin-3-yl)pyrrolidin-3-yl]amino]-1,3,4-thiadiazol-2-yl]-2-methoxy-acetamide | m/z: ES+ [M + H]+ 521 |
| 43 | 2-(3,5-dimethoxyphenyl)-2-methoxy-N-[5-[[(3R)-1-pyridazin-3-ylpyrrolidin-3-yl]amino]-1,3,4-thiadiazol-2-yl]acetamide | m/z: ES+ [M + H]+ 472 |
| 44 | 2-(3,5-dimethoxyphenyl)-2-methoxy-N-[5-[[(3R)-1-pyridazin-3-ylpyrrolidin-3-yl]amino]-1,3,4-thiadiazol-2-yl]acetamide | m/z: ES+ [M + H]+ 472 |

Example 45(a) and 45(b)

(2S)-3-Methoxy-N-[5-[[(3R)-1-(6-methylpyridazin-3-yl)pyrrolidin-3-yl]amino]-1,3,4-thiadiazol-2-yl]-2-phenyl-propanamide and (2R)-3-Methoxy-N-[5-[[(3R)-1-(6-methylpyridazin-3-yl)pyrrolidin-3-yl]amino]-1,3,4-thiadiazol-2-yl]-2-phenyl-propanamide

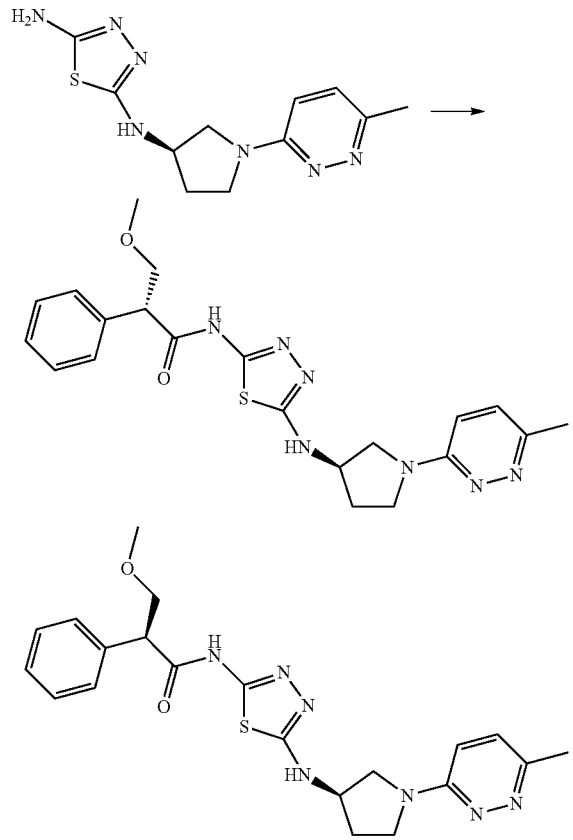

N2-[(3R)-1-(6-methylpyridazin-3-yl)pyrrolidin-3-yl]-1,3,4-thiadiazole-2,5-diamine (Intermediate 6, 0.11 g, 0.389 mmol) and 3-methoxy-2-phenyl-propanoic acid (0.08 g, 0.433 mmol) were dissolved in DMF (2 mL) at r.t under $N_2$. The mixture was stirred for 5 mins before addition of DIPEA (0.34 mL, 1.943 mmol), and N-[(Dimethylamino)(3H-[1,2,3]triazolo[4,5-b]pyridin-3-yloxy)methylidene]-N-methylmethylaminium hexafluorophosphate, HATU (0.4 mL, 0.361 mmol), then left to sit overnight at room temperature. The crude mixture was passed through a 5 g SCX-2 column, washed with MeOH then eluted with 2 M $NH_3$ in MeOH. The pure fractions were combined and solvent was removed under reduced pressure and the residue was further purified by preparative HPLC (SunFire C18 column, 5 μm, 50 mm×19 mm, flow rate 25 mL/min). Decreasingly polar ratios of water and MeCN containing 0.1% formic acid were used as a mobile phase. Pure fractions were combined, evaporated under reduced pressure and passed through an SCX-2 column washed with MeOH then eluted with 2 M $NH_3$ in MeOH. The basic fraction was evaporated to dryness to afford the mixture of diastereoisomers as a pale yellow solid. The diastereoisomers were separated by preparative HPLC (Phenomonex Lux C1 column, 20 m silica, 50 mm diameter, 250 mm length), using a 95/5 mixture of MeCN/MeOH as eluents at 120 mL/min. Fractions containing the desired compounds were evaporated to dryness to afford:

First eluted isomer example 45(a) 3-Methoxy-N-[5-[[(3R)-1-(6-methylpyridazin-3-yl)pyrrolidin-3-yl]amino]-1,3,4-thiadiazol-2-yl]-2-phenyl-propanamide (31.7 mg, 20%). $^1$H NMR (400 MHz, DMSO, 30° C.) 1.95-2.12 (1H, m), 2.21-2.35 (1H, m), 2.42 (3H, s), 3.26 (3H, s), 3.4-3.63 (4H, m), 3.74 (1H, dd), 3.98 (1H, t), 4.12 (1H, dd), 4.31-4.43 (1H, m), 6.82 (1H, d), 7.15-7.46 (6H, m), 7.62 (1H, d), 12.18 (1H, s). m/z: ES$^+$ [M+H]$^+$ 440.

Second eluted isomer example 45(b) 3-Methoxy-N-[5-[[(3R)-1-(6-methylpyridazin-3-yl)pyrrolidin-3-yl]amino]-1,3,4-thiadiazol-2-yl]-2-phenyl-propanamide (28.3 mg, 18%). $^1$H NMR (400 MHz, DMSO, 30° C.) 1.99-2.12 (1H, m), 2.2-2.36 (1H, m), 2.41 (3H, s), 3.26 (3H, s), 3.39-3.62 (4H, m), 3.73 (1H, dd), 3.98 (1H, t), 4.12 (1H, dd), 4.31-4.42 (1H, m), 6.82 (1H, d), 7.17-7.46 (5H, m), 7.62 (1H, d), 12.19 (1H, s). m/z: ES$^+$ [M+H]$^+$ 440.

Additional Examples

The compounds of the following Examples were prepared in a similar fashion to the Examples above.

| Example no. | Name | MS data m/z: ES$^+$ [M + H]$^+$ |
|---|---|---|
| 46(a) and 46(b) | (2R)-2-ethoxy-2-phenyl-N-(5-{[(3R)-1-(1,2,4-triazin-3-yl)-3-pyrrolidinyl]amino}-1,3,4-thiadiazol-2-yl)acetamide and (2S)-2-ethoxy-2-phenyl-N-(5-{[(3R)-1-(1,2,4-triazin-3-yl)-3-pyrrolidinyl]amino}-1,3,4-thiadiazol-2-yl)acetamide | 427 and 427 |
| 47(a) and 47(b) | (2S)-2-(4-fluorophenyl)-3-methoxy-N-(5-{[(3R)-1-(3-pyridazinyl)-3-pyrrolidinyl]amino}-1,3,4-thiadiazol-2-yl)propanamide and (2R)-2-(4-fluorophenyl)-3-methoxy-N-(5-{[(3R)-1-(3-pyridazinyl)-3-pyrrolidinyl]amino}-1,3,4-thiadiazol-2-yl)propanamide | 444 and 444 |
| 48(a) and 48(b) | (2R)-3-methoxy-2-phenyl-N-(5-{[(3R)-1-(3-pyridazinyl)-3-pyrrolidinyl]amino}-1,3,4-thiadiazol-2-yl)propanamide and (2R)-3-methoxy-2-phenyl-N-(5-{[(3R)-1-(3-pyridazinyl)-3-pyrrolidinyl]amino}-1,3,4-thiadiazol-2-yl)propanamide | 426 and 426 |
| 49(a) and 49(b) | (2R)-3-methoxy-2-phenyl-N-(5-{[(3R)-1-(1,2,4-triazin-3-yl)-3-pyrrolidinyl]amino}-1,3,4-thiadiazol-2-yl)propanamide and (2S)-3-methoxy-2-phenyl-N-(5-{[(3R)-1-(1,2,4-triazin-3-yl)-3-pyrrolidinyl]amino}-1,3,4-thiadiazol-2-yl)propanamide | 427 and 427 |

-continued

| Example no. | Name | MS data m/z: ES+ [M + H]+ |
|---|---|---|
| 50(a) and 50(b) | (2R)-2-ethoxy-2-(4-fluorophenyl)-N-(5-{[(3R)-1-(3-pyridazinyl)-3-pyrrolidinyl]amino}-1,3,4-thiadiazol-2-yl)acetamide and (2S)-2-ethoxy-2-(4-fluorophenyl)-N-(5-{[(3R)-1-(3-pyridazinyl)-3-pyrrolidinyl]amino}-1,3,4-thiadiazol-2-yl)acetamide | 444 and 444 |
| 51(a) and 51(b) | (2S)-2-ethoxy-2-(4-fluorophenyl)-N-(5-{[(3R)-1-(1,2,4-triazin-3-yl)-3-pyrrolidinyl]amino}-1,3,4-thiadiazol-2-yl)acetamide and (2R)-2-ethoxy-2-(4-fluorophenyl)-N-(5-{[(3R)-1-(1,2,4-triazin-3-yl)-3-pyrrolidinyl]amino}-1,3,4-thiadiazol-2-yl)acetamide | 445 and 445 |
| 52(a) and 52(b) | (2S)-2-ethoxy-2-(4-fluoro-3-methoxyphenyl)-N-(5-{[(3R)-1-(1,2,4-triazin-3-yl)-3-pyrrolidinyl]amino}-1,3,4-thiadiazol-2-yl)acetamide and (2R)-2-ethoxy-2-(4-fluoro-3-methoxyphenyl)-N-(5-{[(3R)-1-(1,2,4-triazin-3-yl)-3-pyrrolidinyl]amino}-1,3,4-thiadiazol-2-yl)acetamide | 475 and 475 |
| 53(a) and 53(b) | (2R)—N-[5-[[(3R)-1-(6-fluoropyridazin-3-yl)pyrrolidin-3-yl]amino]-1,3,4-thiadiazol-2-yl]-3-methoxy-2-phenyl-propanamide and (2S)—N-[5-[[(3R)-1-(6-fluoropyridazin-3-yl)pyrrolidin-3-yl]amino]-1,3,4-thiadiazol-2-yl]-3-methoxy-2-phenyl-propanamide | 444 and 444 |
| 54(a) and 54(b) | (2R)-3-methoxy-N-[5-[[(3R)-1-(6-methylpyridazin-3-yl)pyrrolidin-3-yl]amino]-1,3,4-thiadiazol-2-yl]-2-phenyl-propanamide and (2R)-3-methoxy-N-[5-[[(3R)-1-(6-methylpyridazin-3-yl)pyrrolidin-3-yl]amino]-1,3,4-thiadiazol-2-yl]-2-phenyl-propanamide | 440 and 440 |

Intermediate 1

N'-[(3R)-1-Pyridazin-3-ylpyrrolidin-3-yl]-1,3,4-thiadiazole-2,5-diamine

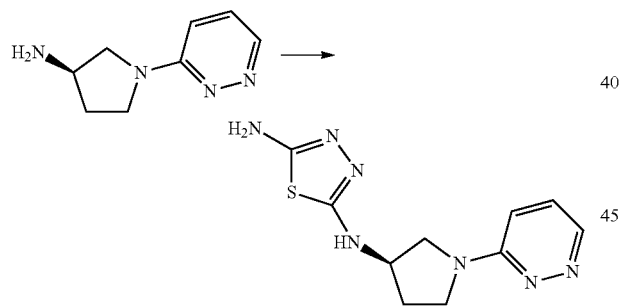

Into a 1 L round-bottom flask was placed a solution of (3R)-1-pyridazin-3-ylpyrrolidin-3-amine dihydrochloride (Intermediate 2, 10.5 g, 44.29 mmol) in DMF (400 mL), 5-bromo-1,3,4-thiadiazol-2-amine (7.94 g, 44.10 mmol) and DIPEA (17.07 g, 132.08 mmol). The solution was stirred for 4 h at 80° C. The resulting mixture was concentrated under vacuum. The crude product was purified by re-crystallization from ethanol/EtOAc to give N-[(3R)-1-pyridazin-3-ylpyrrolidin-3-yl]-1,3,4-thiadiazole-2,5-diamine as a light yellow solid (11 g, 94%). 1H NMR (500 MHz, DMSO-d6, 30° C.) δ2.04 (1H, td), 2.22-2.31 (1H, m), 3.43-3.62 (3H, m), 3.72 (1H, dd), 4.28 (1H, dq), 6.27 (2H, s), 6.86 (1H, dd), 7.07 (1H, d), 7.33 (1H, dd), 8.48 (1H, dd). m/z: ES+ [M+H]+ 264.28.

Intermediate 1 was also prepared on a large scale according to the following alternative procedure:

(R)-1-(Pyridazin-3-yl)pyrrolidin-3-amine (Intermediate 3, free base form, 25.5 g, 150.63 mmol) and 5-bromo-1,3,4-thiadiazol-2-amine (29.8 g, 165.70 mmol) with DIPEA (39.4 mL, 225.95 mmol) was agitated as a slurry in MeOH (200 mL) at 45° C. The slurry was cooled to 20° C. and the solid isolated by vacuum filtration. 50 ml MeOH was used as a displacement wash of the filter cake and it was then dried overnight in the vacuum oven at 40° C. Intermediate 1 (32.9 g, 83%) was obtained as a free flowing beige powder.

Intermediate 2

(3R)-1-Pyridazin-3-ylpyrrolidin-3-amine Dihydrochloride

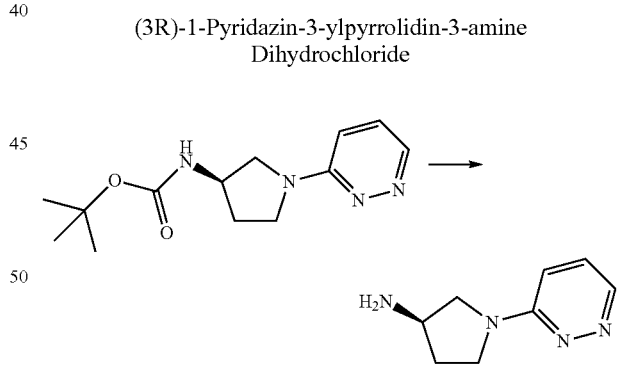

Into a 1 L round-bottom flask was placed a solution of tert-butyl N-[(3R)-1-pyridazin-3-ylpyrrolidin-3-yl]carbamate (Intermediate 4, 20 g, 75.66 mmol) in dioxane (200 mL) and concentrated HCl (100 mL). The solution was stirred for 30 mins at r.t. The resulting mixture was concentrated under vacuum. The crude product was re-crystallized from MeOH/EtOAc in the ratio of 1:2. This resulted in (3R)-1-pyridazin-3-ylpyrrolidin-3-amine dihydrochloride as an off-white solid (13.4 g, 75%). 1H NMR (300 MHz, DMSO-d6, 26° C.) δ2.25-2.43 (2H, m), 3.66-3.74 (1H, m), 3.78-3.90 (3H, m), 4.02-4.10 (1H, m), 7.75 (1H, d), 7.94 (1H, dd), 8.66 (1H, d), 8.77-8.98 (3H, brm). m/z: ES+ [M+H]+ 165.

Intermediate 3 (free base form) was prepared according to the following procedure: tert-butyl N-[(3R)-1-(6-Chloropyridazin-3-yl)pyrrolidin-3-yl]carbamate (Intermediate 5, 20 g, 107.38 mmol) in pyridine (400 mL) was mixed with palladium hydroxide on carbon (Pearlman's Catalyst, 27.5 g, 25.84 mmol) and 1-methyl-1,4-cyclohexadiene (31.0 ml, 276.13 mmol) in MeOH (1375 mL). The reaction mixture was then heated to 65° C. for 90 minutes. With complete conversion observed, the reaction was cooled back to ambient temperature and the catalyst removed by filtration. 3M HCl in MeOH (184 mL, 552.27 mmol) was then charged to the reaction mixture, and the solution heated to 65° C. for 1 h. With complete conversion observed, the reaction solution was cooled back to ambient and passed through 10×50 g SCX columns which had been pre-eluted with MeOH. The compound was released from the SCX using 1M NH$_3$ in MeOH. The resulting solution was diluted with toluene (1 L) and concentrated to dryness via rotary evaporation to give a free flowing solid. (3R)-1-pyridazin-3-ylpyrrolidin-3-amine was isolated at a strength of 97% w/w as the free base.

Intermediate 4 tert-Butyl N-[(3R)-1-pyridazin-3-ylpyrrolidin-3-yl]carbamate

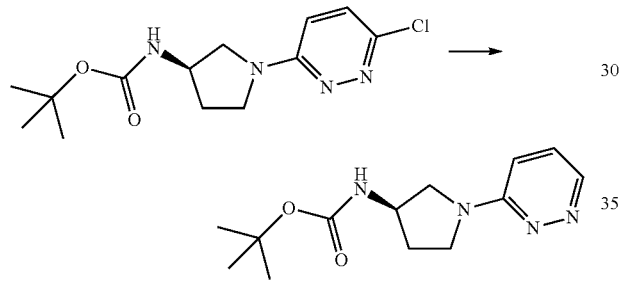

Into a 2 L round-bottom flask was placed a solution of tert-butyl N-[(3R)-1-(6-chloropyridazin-3-yl)pyrrolidin-3-yl]carbamate (Intermediate 5, 23 g, 76.98 mmol) in MeOH (800 mL) and Palladium on carbon (2 g). The system was purged and maintained with Hydrogen gas. The resulting solution was stirred for 4 h at r.t. The solids were filtered out. The resulting mixture was concentrated under vacuum to give tert-butyl N-[(3R)-1-pyridazin-3-ylpyrrolidin-3-yl]carbamate (20 g, 84%) as a yellow solid. $^1$H NMR (300 MHz, CDCl$_3$, 24° C.) δ1.44 (9H, s), 2.25-2.35 (2H, m), 3.48-3.56 (1H, m), 3.70-4.10 (3H, m), 4.35-4.42 (1H, m), 7.26-7.32 (1H, m), 7.70-7.75 (1H, m), 8.53-8.55 (1H, m). m/z: ES$^+$ [M+H]$^+$ 265.

Intermediate 5

Tert-Butyl N-[(3R)-1-(6-chloropyridazin-3-yl)pyrrolidin-3-yl]carbamate

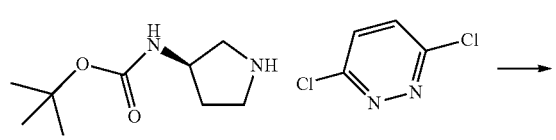

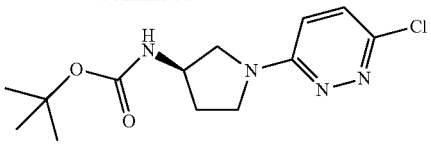

Into a 1 L round-bottom flask was placed a solution of tert-butyl N-[(3R)-pyrrolidin-3-yl]carbamate (20 g, 107.38 mmol) in pyridine (400 mL) and 3,6-dichloropyridazine (16 g, 107.40 mmol). The resulting solution was heated to reflux for overnight. The resulting mixture was concentrated under vacuum. The crude product was purified by re-crystallization from ethanol/Et$_2$O in the ratio of 1:3 to give tert-butyl N-[(3R)-1-(6-chloropyridazin-3-yl)pyrrolidin-3-yl]carbamate (23 g, 72%) as a yellow solid.
$^1$H NMR (400 MHz, CDCl$_3$, 30° C.) δ1.45 (9H, s), 2.02 (1H, dq), 2.31 (1H, td), 3.41 (1H, dd), 3.54-3.70 (2H, m), 3.78 (1H, dd), 4.37 (1H, s), 4.76 (1H, s), 6.61 (1H, d), 7.17 (1H, d). m/z: ES$^+$ [M+H]$^+$ 299.

Intermediate 6

N2-[(3R)-1-(6-Methylpyridazin-3-yl)pyrrolidin-3-yl]-1,3,4-thiadiazole-2,5-diamine

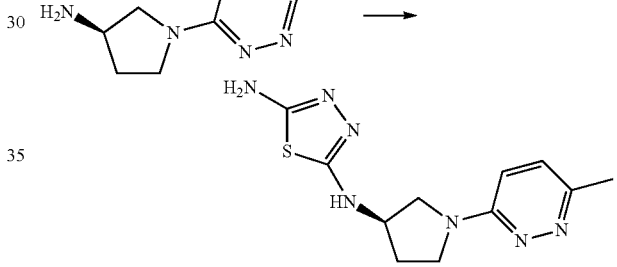

5-Bromo-1,3,4-thiadiazol-2-amine (912 mg, 5.07 mmol), (3R)-1-(6-methylpyridazin-3-yl)pyrrolidin-3-amine (Intermediate 7, 860 mg, 4.83 mmol) and DIPEA (0.924 mL, 5.31 mmol) were dissolved in DMF (10 mL). The reaction was heated to 100° C. for 1 h then left at r.t. overnight. The crude product was purified by ion exchange chromatography, using an SCX column. The desired product was eluted from the column using 1M NH$_3$ in MeOH and pure fractions were evaporated to dryness to afford crude product. This was dissolved in DCM/MeOH, adsorbed onto silica and purified by FCC (SiO$_2$, 0 to 20% MeOH in DCM). Pure fractions were evaporated to dryness to afford N2-[(3R)-1-(6-methylpyridazin-3-yl)pyrrolidin-3-yl]-1,3,4-thiadiazole-2,5-diamine (350 mg, 26%) as a brown gum. m/z: ES$^+$ [M+H]$^+$ 278.

Intermediate 7

(3R)-1-(6-Methylpyridazin-3-yl)pyrrolidin-3-amine

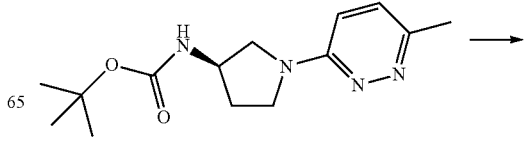

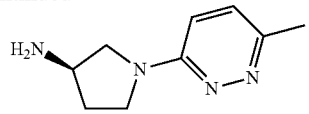

Trifluoroacetic acid (12 mL) was added to tert-butyl N-[(3R)-1-(6-methylpyridazin-3-yl)pyrrolidin-3-yl]carbamate (Intermediate 8, 2.1 g, 7.54 mmol), in DCM (60 mL) at 21° C. under nitrogen. The resulting solution was stirred at 21° C. for 2 h. The crude product was purified by ion exchange chromatography, using an SCX column. The desired product was eluted from the column using 7M $NH_3$ in MeOH and pure fractions were evaporated to dryness to afford (3R)-1-(6-methylpyridazin-3-yl)pyrrolidin-3-amine (1.6 g, 119%) as a yellow oil which solidified on standing. $^1$H NMR (400 MHz, DMSO-d6, 27° C.) δ1.56-1.8 (1H, m), 2.04 (1H, m), 2.39 (3H, s), 3.07 (1H, m), 3.37-3.43 (1H, m), 3.47-3.66 (3H, m), 4.08 (1H, s), 6.73 (1H, d), 7.19 (1H, d). m/z: $ES^+$ $[M+H]^+$ 179.

Intermediate 8

Tert-Butyl N-[(3R)-1-(6-methylpyridazin-3-yl)pyrrolidin-3-yl]carbamate

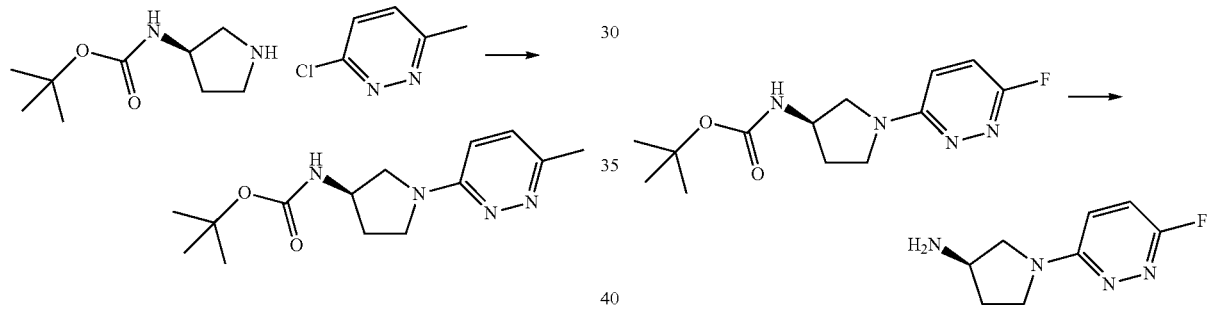

A mixture of DIPEA (8.49 mL, 48.62 mmol), tert-butyl N-[(3R)-pyrrolidin-3-yl]carbamate (3.62 g, 19.45 mmol), 3-chloro-6-methylpyridazine (2.5 g, 19.45 mmol) and n-butanol (30 mL) was stirred at 130° C. for 12 h then left to cool over the weekend. The reaction mixture was evaporated and the crude product was purified by FCC ($SiO_2$, 0 to 10% 1M $NH_3$ in MeOH in EtOAc). Pure fractions were evaporated to dryness to afford tert-butyl N-[(3R)-1-(6-methylpyridazin-3-yl)pyrrolidin-3-yl]carbamate (2.1 g, 38.8%) as a yellow solid. $^1$H NMR (400 MHz, DMSO-d6, 27° C.) δ1.39 (9H, s), 1.88 (1H, m), 2.14 (1H, m), 2.40 (3H, s), 3.23 (1H, m), 3.37-3.45 (1H, m), 3.47-3.58 (1H, m), 3.61 (1H, m), 3.99-4.2 (1H, m), 6.77 (1H, d), 7.20 (2H, m). m/z: $ES^+$ $[M+H]^+$ 279.

Intermediate 9

N2-[(3R)-1-(6-Fluoropyridazin-3-yl)pyrrolidin-3-yl]-1,3,4-thiadiazole-2,5-diamine

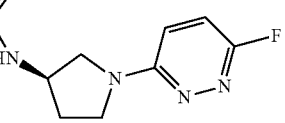

DIPEA (3.48 mL, 19.96 mmol) was added to 5-bromo-1,3,4-thiadiazol-2-amine (1.797 g, 9.98 mmol) and (3R)-1-(6-fluoropyridazin-3-yl)pyrrolidin-3-amine (Intermediate 10, 2 g, 10.98 mmol) in anhydrous DMF (40 mL) at r.t. The resulting solution was stirred at 80° C. for 4 h. The crude product was purified by ion exchange chromatography, using an SCX column. The desired product was eluted from the column using 1M $NH_3$ in MeOH and pure fractions were evaporated to dryness to afford N2-[(3R)-1-(6-fluoropyridazin-3-yl)pyrrolidin-3-yl]-1,3,4-thiadiazole-2,5-diamine (2.9 g, 103%) as a brown solid. $^1$H NMR (400 MHz, DMSO-d6, 30° C.) δ 1.90-2.12 (1H, m), 2.23 (1H, dtd), 3.42 (1H, dd), 3.47-3.61 (2H, m), 3.69 (1H, dd), 4.25 (1H, dq), 6.25 (2H, s), 7.04 (1H, d), 7.14 (1H, dd), 7.33 (1H, dd). m/z: $ES^+$ $[M+H]^+$ 282.

Intermediate 10

(3R)-1-(6-Fluoropyridazin-3-yl)pyrrolidin-3-amine tert-Butyl N-[(3R)-1-(6-fluoropyridazin-3-yl)pyrrolidin-3-yl]carbamate (Intermediate 11, 6 g, 21.25 mmol) was added to DCM (70 mL) and TFA (14.00 mL) at 25° C. The resulting solution was stirred at 25° C. for 4 h. The crude product was purified by ion exchange chromatography, using an SCX column. The desired product was eluted from the column using 1M $NH_3$ in MeOH and pure fractions were evaporated to dryness to afford (3R)-1-(6-fluoropyridazin-3-yl)pyrrolidin-3-amine (2.0 g, 52%) as a pale yellow gummy solid. $^1$H NMR (400 MHz, DMSO-d6, 30° C.) δ1.55-1.83 (1H, m), 1.98-2.13 (1H, m), 2.89-3.14 (1H, m), 3.29-3.43 (1H, m), 3.54 (3H, ddt), 7.06 (1H, dd), 7.30 (1H, dd). m/z: $ES^+$ $[M+H]^+$ 183.

Intermediate 11

Tert-butyl N-[(3R)-1-(6-Fluoropyridazin-3-yl)pyrrolidin-3-yl]carbamate

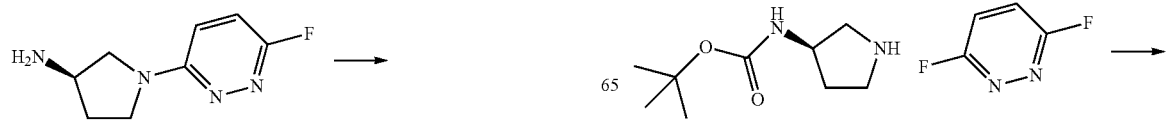

-continued

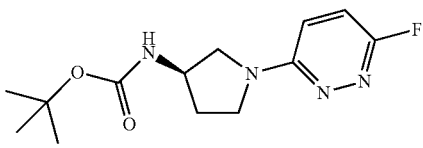

A mixture of 3,6-difluoropyridazine (6.06 g, 52.21 mmol) tert-butyl N-[(3R)-pyrrolidin-3-yl]carbamate (9.72 g, 52.21 mmol), DIPEA (22.80 mL, 130.53 mmol) and n-butanol (140 mL) was stirred at 130° C. for 10 h. The reaction mixture was diluted with EtOAc (750 mL), and washed twice with water (150 mL). The organic layer was dried over $Na_2SO_4$, filtered and evaporated to afford crude product. This was then dissolved in DCM and the crude product was purified by FCC ($SiO_2$, 30-65% EtOAc in heptanes). Pure fractions were evaporated to dryness to afford tert-butyl N-[(3R)-1-(6-fluoropyridazin-3-yl)pyrrolidin-3-yl]carbamate (15 g, 102%) as a cream solid. $^1$H NMR (400 MHz, $CDCl_3$, 30° C.) δ1.46 (9H, s), 1.91-2.13 (1H, m), 2.32 (1H, dq), 3.40 (1H, dd), 3.56-3.72 (2H, m), 3.78 (1H, dd), 4.37 (1H, s), 4.70 (1H, s), 6.78 (1H, dd), 6.98 (1H, dd). m/z: ES$^+$ [M+H]$^+$ 283.

Intermediate 12

N2-[(3R)-1-(1,2,4-Triazin-3-yl)pyrrolidin-3-yl]-1,3,4-thiadiazole-2,5-diamine

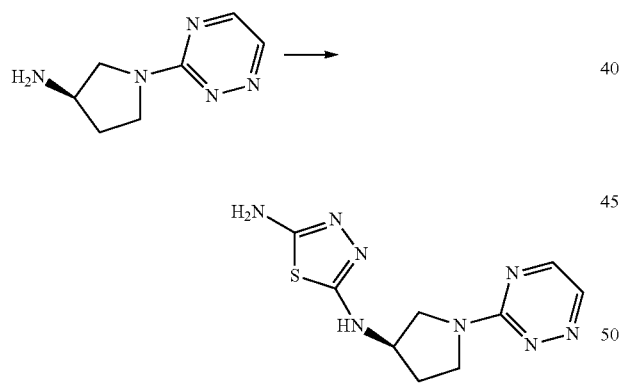

5-bromo-1,3,4-thiadiazol-2-amine (1.31 g, 7.264 mmol) and (3R)-1-(1,2,4-triazin-3-yl)pyrrolidin-3-amine (Intermediate 13, 1.2 g, 7.264 mmol) were combined in DMF (15 mL) at r.t. under $N_2$. The mixture was stirred at r.t. overnight. It was then evaporated to dryness and purified by FCC ($SiO_2$, 5-10% 2N $NH_3$ in MeOH in DCM) to give N2-[(3R)-1-(1,2,4-triazin-3-yl)pyrrolidin-3-yl]-1,3,4-thiadiazole-2,5-diamine as a beige foam (1.7 g, 88%). $^1$H NMR (400 MHz, DMSO, 30° C.) δ1.80-1.85 (1H, m), 1.98-2.05 (1H, m), 3.40 (4H, brs), 4.03 (1H, brs), 6.09 (2H, s), 6.88 (1H, d), 8.10 (1H, d), 8.38 (1H, d).

Intermediate 13

(3R)-1-(1,2,4-Triazin-3-yl)pyrrolidin-3-amine

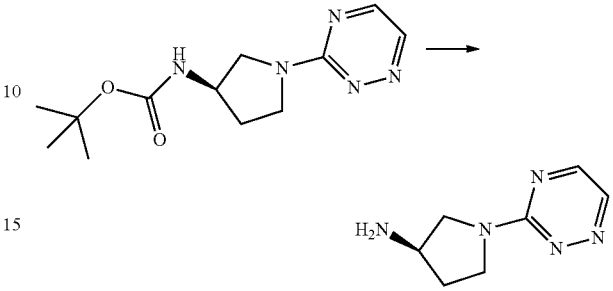

tert-Butyl N-[(3R)-1-(1,2,4-triazin-3-yl)pyrrolidin-3-yl]carbamate (Intermediate 14, 2.39 g, 9.01 mmol) was dissolved in a mixture of DCM (20 mL) and trifluoroacetic acid (5 mL) and the solution allowed to stand for 1 h at r.t. before being evaporated under reduced pressure. The residue was dissolved in MeOH and passed through a 20 g SCX cartridge flushing with MeOH followed by 3N $NH_3$ in MeOH to bring off the product. The solvent was evaporated under reduced pressure to yield (3R)-1-(1,2,4-triazin-3-yl)pyrrolidin-3-amine (1.460 g, 98%) as a yellow solid. $^1$H NMR (400 MHz, $CDCl_3$, 27° C.) δ1.80-1.92 (1H, m), 2.18-2.29 (1H, m), 3.45 (1H, s), 3.6-4.01 (4H, m), 8.13 (1H, d), 8.50 (1H, d). m/z: ES$^+$ [M+H]$^+$ 166.

Intermediate 14

Tert-Butyl N-[(3R)-1-(1,2,4-Triazin-3-yl)pyrrolidin-3-yl]carbamate

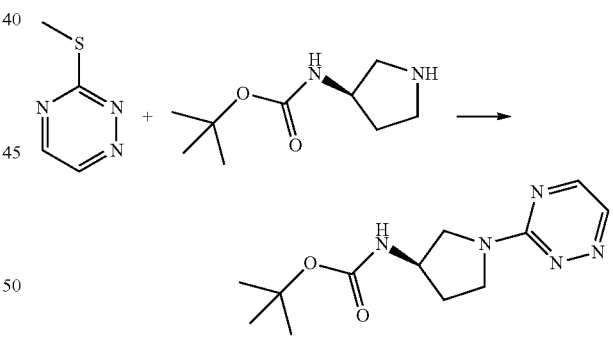

3-Methylsulfanyl-1,2,4-triazine (Intermediate 15, 1.5 g, 11.80 mmol), and tert-butyl N-[(3R)-pyrrolidin-3-yl]carbamate (2.64 g, 14.15 mmol) were dissolved in ethanol (12 mL) and sealed into a microwave tube. The reaction was heated to 100° C. for 24 h in the microwave reactor and cooled to r.t. LC/MS showed 61% product and 34% unreacted triazine. Further tert-butyl N-[(3R)-pyrrolidin-3-yl]carbamate (0.52 g) was added and heating at 100° C. in the microwave continued for 15 h. LC/MS showed 76% product and 18% unreacted triazine. The solvent was removed under reduced pressure and the residue partitioned between EtOAc and aqueous sodium bicarbonate. The aqueous layer was re-extracted with fresh EtOAc and the combined organics were dried ($MgSO_4$) filtered and evaporated under reduced pressure. The crude product was purified by FCC (SiO₂, 0 to 80% EtOAc in heptanes). Relevant fractions were evaporated to give tert-butyl N-[(3R)-1-(1,2,4-triazin-3-yl)pyrrolidin-3-yl]carbamate (2.390 g, 76%) as a yellow solid. ¹H NMR (400 MHz, CDCl₃, 27° C.) δ1.46 (9H, s), 1.96-2.07 (1H, m), 2.26-2.37 (1H, m), 3.55 (1H, s), 3.75 (2H, s), 3.90 (1H, s), 4.39 (1H, s), 4.69 (1H, s), 8.14 (1H, d), 8.53 (1H, d). m/z: ES⁻ [M−H]⁻ 264.

Intermediate 15

3-Methylsulfanyl-1,2,4-triazine

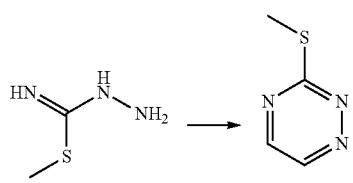

A solution of methyl hydrazinecarbimidothioate hydroiodide (Intermediate 16, 7.5 g, 32.18 mmol) in ice/water (400 mL) was added to a stirred solution of 40% oxalaldehyde (14.70 mL, 128.71 mmol), and sodium bicarbonate (6.76 g, 80.45 mmol) in ice/water (400 mL) cooled to 0° C. The resulting solution was stirred at 0° C. for 5 h, then extracted with DCM (2×150 mL). The extracts were combined washed with 1M citric acid (50 mL), dried (MgSO₄) and evaporated to give 3-methylsulfanyl-1,2,4-triazine (3.60 g, 88%) as a yellow solid. ¹H NMR (400 MHz, CDCl₃, 27° C.) δ2.68 (3H, s), 8.38 (1H, d), 8.94 (1H, d).

Intermediate 16

Hydrazinecarbimidothioate Hydroiodide

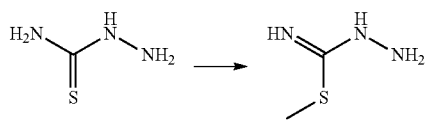

Iodomethane (0.623 mL, 10.00 mmol) was added to hydrazinecarbothioamide (0.911 g, 10 mmol), in ethanol (10 mL). The resulting mixture was stirred at 70° C. for 30 minutes. The reaction was allowed to cool to r.t. The reaction mixture was then filtered through a Nylon filtercup. The resultant solid was then washed with Et₂O and dried under vacuum overnight to give methyl hydrazinecarbimidothioate hydroiodide (1.810 g, 78%) as a white solid that was used without further purification.

Intermediate 17

[2-[3-(3-Fluoroazetidin-1-yl)phenyl]-2-methoxy-acetyl]oxylithium

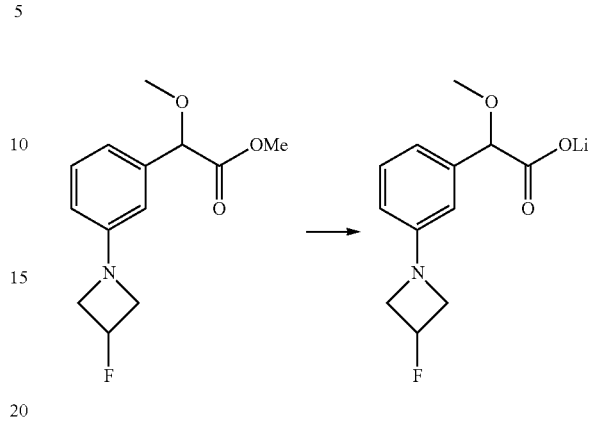

Methyl 2-[3-(3-fluoroazetidin-1-yl)phenyl]-2-methoxy-acetate (Intermediate 18, 0.26 g, 1.034 mmol) and lithium hydroxide monohydrate (0.07 g, 1.552 mmol) were dissolved in a mixture of MeOH (5 mL) and water (2 mL). The reaction was stirred for 2 h at r.t. It was then evaporated and dried in vacuo over the weekend to give [2-[3-(3-fluoroazetidin-1-yl)phenyl]-2-methoxy-acetyl]oxylithium as a white solid (270 mg, 100%). ¹H NMR (400 MHz, DMSO-d6, 27° C.) δ3.35 (3H, s), 4.08-3.91 (2H, m), 4.29 (2H, ddd), 4.42 (1H, s), 5.78-5.56 (1H, m), 6.50 (1H, ddd), 6.68 (1H, t), 6.93 (1H, dt), 7.25 (1H, t). m/z: ES⁺ [M+H]⁺ 240.

Intermediate 18

Methyl 2-[3-(3-fluoroazetidin-1-yl)phenyl]-2-methoxy-acetate

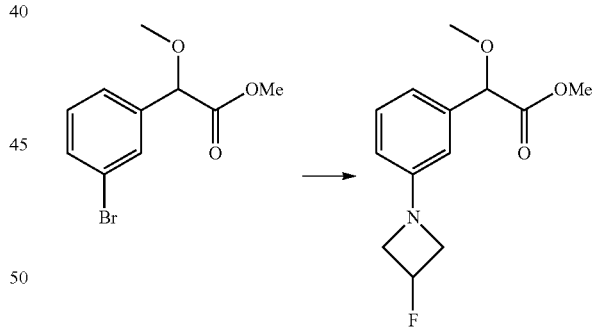

To a mixture of methyl 2-(3-bromophenyl)-2-methoxyacetate (Intermediate 19, 500 mg, 1.93 mmol) and 3-fluoroazetidine hydrochloride (215 mg, 1.93 mmol) in toluene (20 mL) was added Ruphos palladium(II) phenethylamine chloride (58.3 mg, 0.07 mmol), dicyclohexyl(2',6'-diisopropoxy-[1,1'-biphenyl]-2-yl)phosphine (29.7 mg, 0.06 mmol) and caesium carbonate (2.20 mg, 6.75 mmol). The reaction was sparged with nitrogen for ~5 minutes and then heated to 90° C., stirring under nitrogen overnight. The reaction was cooled to r.t. before being diluted with EtOAc and water. The organic layer was dried (MgSO₄), filtered and the solvent evaporated under reduced pressure. Purification was by FCC (SiO₂, 0-25% EtOAc in heptanes). Fractions containing product were evaporated under reduced pressure to yield methyl 2-[3-(3-fluoroazetidin-1-yl)phenyl]-2-methoxy-acetate (330 mg, 67%) as an oil. $^1$H NMR (400 MHz, CDCl$_3$, 30° C.) δ3.40 (3H, s), 3.72 (3H, s), 3.90-4.02 (2H, m), 4.19 (2H, ddd), 4.71 (1H, s), 5.30-5.51 (1H, m), 6.44 (1H, ddd), 6.54-6.56 (1H, m), 6.83 (1H, d), 7.21 (1H, t). m/z: ES$^+$ [M+H]$^+$ 254.

Intermediate 19

Methyl 2-(3-bromophenyl)-2-methoxyacetate

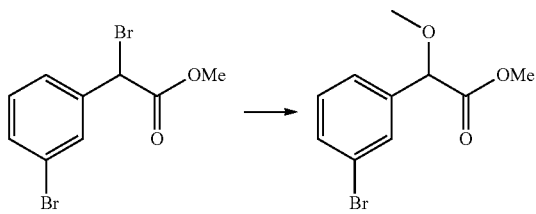

Sodium (0.345 g, 15.00 mmol) was dissolved in dry MeOH (50 mL) under N2 and to this solution was added a solution of methyl 2-bromo-2-(3-bromophenyl)acetate (Intermediate 20, 4.2 g, 13.64 mmol) in dry MeOH (10 mL). The reaction mixture was heated at 40° C. for 2 hours and then evaporated under reduced pressure. The residue was treated with aqueous ammonium chloride solution, and the mixture was extracted with EtOAc (50 mL×2). The combined organics were dried (MgSO$_4$), filtered and evaporated under reduced pressure to yield crude product which was purified by FCC (SiO$_2$, 0-12% EtOAc in heptanes). Fractions containing product were evaporated to dryness to afford methyl 2-(3-bromophenyl)-2-methoxyacetate (2.95 g, 83%) as an oil. $^1$H NMR (400 MHz, CDCl$_3$, 30° C.) δ3.42 (3H, s), 3.74 (3H, s), 4.73 (1H, s), 7.24 (1H, t), 7.36-7.39 (1H, m), 7.47 (1H, ddd), 7.61 (1H, t). m/z: TOF MS EI$^+$ 257.9880.

Intermediate 20

Methyl 2-bromo-2-(3-bromophenyl)acetate

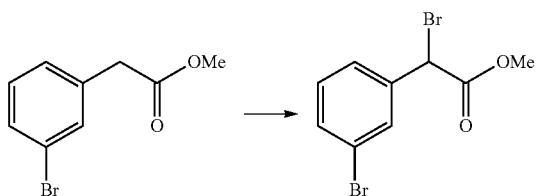 [SMILES: COC(=O)Cc1cccc(Br)c1 ; COC(=O)C(Br)c1cccc(Br)c1]

A mixture of methyl 2-(3-bromophenyl)acetate (4 g, 17.46 mmol) and NBS (3.26 g, 18.33 mmol) and (E)-2,2'-(diazene-1,2-diyl)bis(2-methylpropanenitrile) (0.143 g, 0.87 mmol) in carbon tetrachloride (50 mL) was heated to reflux for 4 hours and then cooled to r.t. The solid was filtered off and discarded, the filtrate evaporated under reduced pressure. Purification was by FCC (SiO$_2$, 0-5% EtOAc in heptane). Fractions containing product were evaporated under reduced pressure to yield methyl 2-bromo-2-(3-bromophenyl)acetate (4.2 g, 78%) as an oil. $^1$H NMR (400 MHz, CDCl$_3$, 30° C.) δ3.80 (3H, s), 5.28 (1H, s), 7.21-7.26 (1H, m), 7.45-7.48 (1H, m), 7.48-7.5 (1H, m), 7.70 (1H, t). m/z: TOF MS EI$^+$ 305.8891.

Intermediate 21

[2-[3-(3,3-difluoroazetidin-1-yl)phenyl]-2-methoxy-acetyl]oxylithium

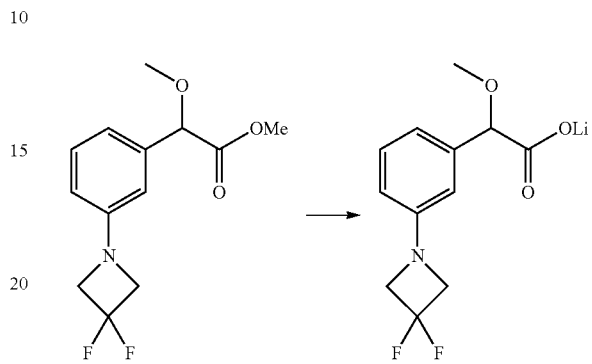

Methyl 2-[3-(3,3-difluoroazetidin-1-yl)phenyl]-2-methoxy-acetate (Intermediate 23, 0.08 g, 0.295 mmol) and lithium hydroxide monohydrate (0.01 g, 0.354 mmol) were dissolved in a mixture of methanol (3 mL) and water (2 mL). The reaction mixture was stirred for 2 h at room temperature. The reaction mixture was evaporated under reduced pressure and dried in the vacuum oven over the weekend to give [2-[3-(3,3-difluoroazetidin-1-yl)phenyl]-2-methoxy-acetyl]oxy-lithium. $^1$H NMR (400 MHz, DMSO-d6) δ 3.19 (3H, s), 4.24-4.17 (4H, m), 6.42-6.35 (1H, m), 6.57 (1H, s), 6.82 (1H, d), 7.09 (1H, t).

Intermediate 22

2-[3-(3,3-Difluoroazetidin-1-yl)phenyl]-2-methoxy-acetic Acid

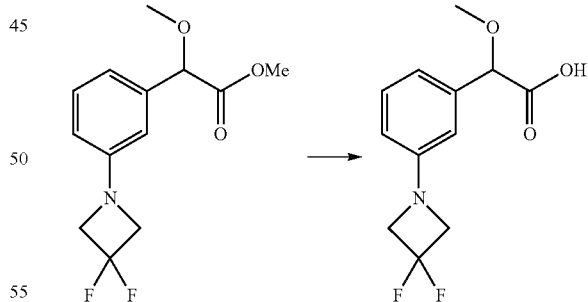

A solution of 2-[3-(3,3-difluoroazetidin-1-yl)phenyl]-2-methoxy-acetate (Intermediate 23, 270 mg, 1.00 mmol) in MeOH (4 mL) was treated with a solution of lithium hydroxide monohydrate (84 mg, 1.99 mmol) in water (2 mL) and the mixture stirred at r.t. for 2 hours. The MeOH was evaporated under reduced pressure and the aqueous layer was diluted with aqueous brine (2 ml), neutralised with acetic acid and extracted with 2-methyltetrahydrofuran (4×5 mL). The combined organics were dried (MgSO$_4$), filtered and evaporated under reduced pressure to yield 2-[3-(3,3- difluoroazetidin-1-yl)phenyl]-2-methoxy-acetic acid (130 mg, 50.8%) as a gum. m/z: ES+ [M+H]+ 258.

Intermediate 23

Methyl 2-[3-(3,3-difluoroazetidin-1-yl)phenyl]-2-methoxy-acetate

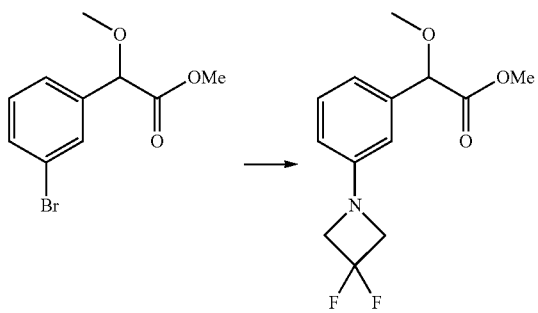 [SMILES: COC(=O)C(OC)c1cccc(Br)c1 ; COC(=O)C(OC)c1cccc(N2CC(F)(F)C2)c1]

To a mixture of methyl 2-(3-bromophenyl)-2-methoxyacetate (Intermediate 19, 473 mg, 1.83 mmol) and 3,3-difluoroazetidine hydrochloride (236 mg, 1.83 mmol) in toluene (20 mL) was added Ruphos palladium (II) phenethylamine chloride (55.2 mg, 0.07 mmol), dicyclohexyl(2',6'-diisopropoxy-[1,1'-biphenyl]-2-yl)phosphine (28.1 mg, 0.06 mmol) and caesium carbonate (2.08 g, 6.39 mmol). The reaction was sparged with $N_2$ for ~5 minutes and then heated to 90° C., with stirring under $N_2$ overnight. The reaction was cooled to r.t. before being diluted with EtOAc (20 mL) and water (20 mL). The organic layer was dried ($MgSO_4$), filtered and the solvent evaporated under reduced pressure. Purification was by FCC, ($SiO_2$, 0-20% EtOAc in heptanes). Fractions containing product were evaporated under reduced pressure to yield methyl 2-[3-(3,3-difluoroazetidin-1-yl)phenyl]-2-methoxy-acetate (280 mg, 57%) as an oil. $^1$H NMR (400 MHz, DMSO-d6, 30° C.) δ3.62 (3H, s), 4.25 (4H, t), 4.82 (1H, s), 6.51-6.56 (2H, m), 6.79 (1H, d), 7.19-7.25 (1H, m). m/z: ES+ [M+H]+ 272.

Intermediate 24

[2-Methoxy-2-[3-(3-methoxyazetidin-1-yl)phenyl]acetyl]oxylithium

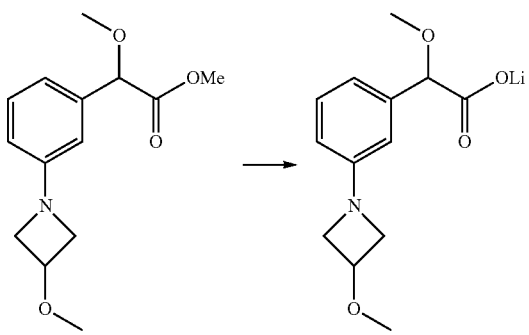

Methyl 2-methoxy-2-[3-(3-methoxyazetidin-1-yl)phenyl]acetate (Intermediate 26, 0.24 g, 0.886 mmol) and lithium hydroxide monohydrate (0.06 g, 1.329 mmol) were dissolved in a mixture of methanol (5 mL) and water (2 mL). The reaction was stirred for 2 h at r.t, then evaporated under reduced pressure and dried in vacuo over the weekend. $^1$H NMR (400 MHz, DMSO-d6) δ 2.96 (3H, s), 3.03 (3H, s), 3.37-3.26 (2H, m), 3.80 (2H, dd), 4.01 (1H, s), 4.09 (1H, tt), 6.06 (1H, dd), 6.25 (1H, t), 6.49 (1H, dt), 6.83 (1H, t).

Intermediate 25

2-Methoxy-2-[3-(3-methoxyazetidin-1-yl)phenyl]acetic Acid

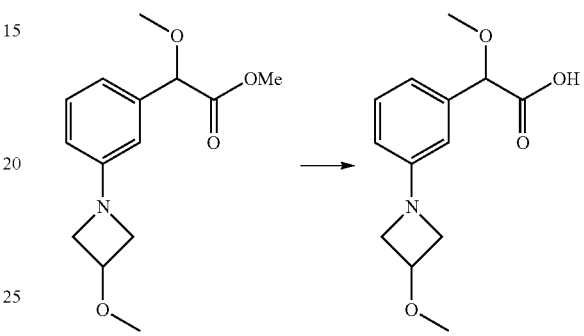

A solution of methyl 2-methoxy-2-[3-(3-methoxyazetidin-1-yl)phenyl]acetate (Intermediate 26, 450 mg, 1.61 mmol) in MeOH (7 mL) was treated with a solution of lithium hydroxide monohydrate (135 mg, 3.22 mmol) in water (3 mL) and the mixture stirred overnight at r.t. The MeOH was evaporated under reduced pressure and the aqueous residue extracted with ether. The aqueous layer was acidified with acetic acid, treated with solid sodium chloride to give a saturated solution and extracted with EtOAc (3×10 mL). The organic layer was dried ($MgSO_4$), filtered and evaporated under reduced pressure to yield 2-methoxy-2-[3-(3-methoxyazetidin-1-yl)phenyl]acetic acid (236 mg, 58.3%) as a gum. $^1$H NMR (400 MHz, DMSO-d6, 30° C.) δ3.23 (3H, s), 3.26 (3H, s), 3.51-3.59 (2H, m), 3.97-4.06 (2H, m), 4.26-4.34 (1H, m), 4.59 (1H, s), 6.38 (1H, dd), 6.43 (1H, s), 6.69 (1H, d), 7.13 (1H, t). m/z: ES+ [M+H]+ 252.

Intermediate 26

Methyl 2-methoxy-2-[3-(3-methoxyazetidin-1-yl)phenyl]acetate

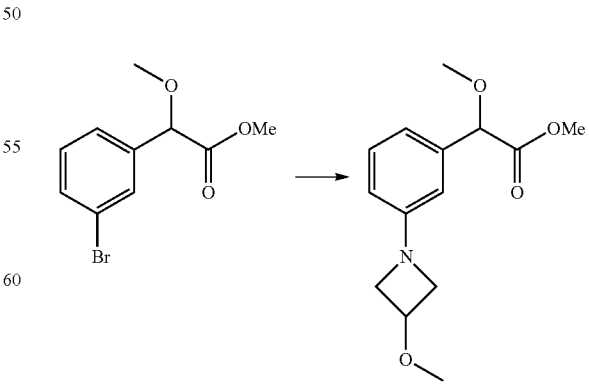

To a mixture of methyl 2-(3-bromophenyl)-2-methoxyacetate (Intermediate 19, 524 mg, 2.02 mmol) and 3-methoxyazetidine hydrochloride (250 mg, 2.02 mmol) in toluene (20 mL) was added Ruphos palladium(II) phenethylamine chloride (61.1 mg, 0.07 mmol), dicyclohexyl(2',6'-diisopropoxy-[1,1'-biphenyl]-2-yl)phosphine (31.2 mg, 0.07 mmol) and caesium carbonate (2307 mg, 7.08 mmol). The reaction was sparged with nitrogen for ~5 minutes and then heated to 90° C., stirring under nitrogen overnight. The reaction was cooled to r.t. before being diluted with EtOAc and water. The organic layer was dried (MgSO$_4$), filtered and the solvent evaporated under reduced pressure. Purification by FCC (SiO$_2$, 0-25% EtOAc in heptanes) gave methyl 2-methoxy-2-[3-(3-methoxyazetidin-1-yl)phenyl]acetate (450 mg, 84%) as an oil. $^1$H NMR (400 MHz, CDCl$_3$, 30° C.) δ3.33 (3H, s), 3.39 (3H, s), 3.68-3.74 (5H, m), 4.07-4.13 (2H, m), 4.29-4.36 (1H, m), 4.70 (1H, s), 6.43 (1H, ddd), 6.51-6.54 (1H, m), 6.79 (1H, d), 7.19 (1H, t). m/z: ES$^+$ [M+H]$^+$ 266.

Intermediate 27

2-Ethoxy-2-(3-methoxyphenyl)acetic Acid

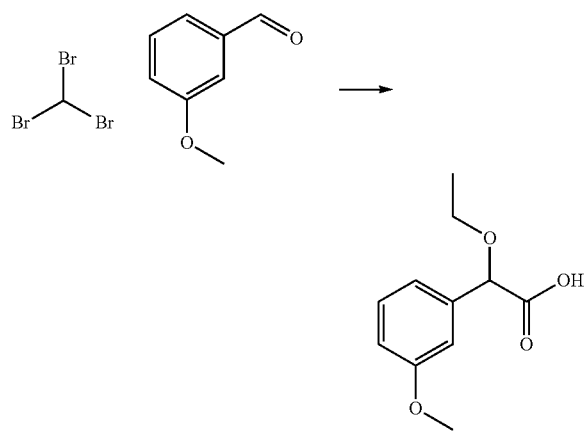

To a stirred mixture of 3-methoxybenzaldehyde (5.0 g, 36.72 mmol) and bromoform (3.85 mL, 44.06 mmol) in ethanol (40 mL) at 0° C. was added dropwise over a 1 hour period a solution of potassium hydroxide (11.33 g, 201.98 mmol) in ethanol (60 mL). After the addition was complete the mixture was left to stir at r.t. overnight. A precipitate had formed which was removed by filtration, and the filtrate was evaporated to give a paste which was taken up in water (100 mL) and extracted with EtOAc (2×100 mL). The aqueous phase was then acidified to pH=2 with 2M HCl and extracted with EtOAc (2×100 mL). The combined organics were dried (MgSO$_4$), filtered and evaporated to give a pale brown oil. This was absorbed onto silica and was purified by FCC (SiO$_2$, 5% MeOH in DCM) to give 2-ethoxy-2-(3-methoxyphenyl)acetic acid (3.1 g, 40%) as a pale brown oil. $^1$H NMR (400 MHz, CDCl$_3$, 21° C.) δ1.28 (3H, t), 2.09 (1H, s), 3.64-3.52 (2H, m), 3.81 (3H, s) 4.86 (1H, s), 6.89 (1H, ddd), 6.99 (1H, m), 7.03 (1H, m), 7.29 (1H, t). m/z: ES$^-$ [M–H]$^-$ 209.

Intermediate 28

2-(3,5-Dimethoxyphenyl)-2-methoxy-acetic Acid

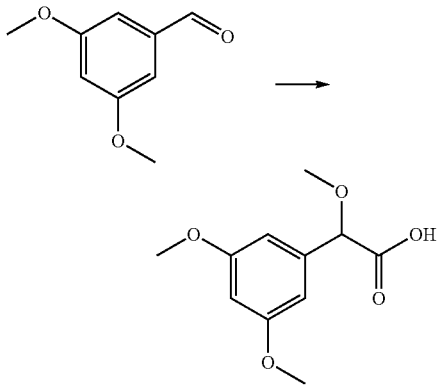

A solution of potassium hydroxide (9.79 g, 174.43 mmol) in MeOH (80 mL) was added over 2 h in small portions to a stirred mixture of 3,5-dimethoxybenzaldehyde (5.27 g, 31.71 mmol) and bromoform (3.33 mL, 38.06 mmol) in MeOH (40 mL) at 0° C. The mixture was then allowed to warm to r.t. and left to stir overnight. Solids were filtered under reduced pressure, and rinsed with MeOH (40 mL). The filtrate was evaporated to a thick white paste and then re-dissolved in water (150 mL). This was washed with Et$_2$O (200 mL) and the aqueous portion acidified to pH=2 with 2M HCl. The aqueous phase was extracted with EtOAc (500 mL). The combined organics were dried (MgSO$_4$), filtered and evaporated under reduced pressure to give 2-(3,5-dimethoxyphenyl)-2-methoxy-acetic acid as a yellow gum (5.00 g, 70%). $^1$H NMR (400 MHz, DMSO-d6, 27° C.) δ3.72 (9H, s), 4.68 (1H, s), 6.45 (1H, s), 6.52 (2H, s).

Intermediate 29

3-Methoxy-2-(3-methoxyphenyl)propanoic Acid

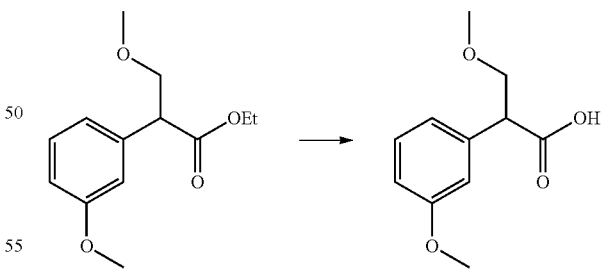

Ethyl 3-methoxy-2-(3-methoxyphenyl)propanoate (Intermediate 30, 0.3 g, 1.259 mmol) was suspended in water (5 mL) and treated with lithium hydroxide (0.3 g, 12.59 mmol) then heated at 60° C. for 3 hours. The reaction mixture was allowed to cool to r.t. The aqueous was extracted with EtOAc (20 mL) and the organics were discarded. The aqueous was acidified with 1 M HCl to pH=1 and extracted with EtOAc (2×20 mL). The organics were dried (MgSO$_4$), filtered and evaporated under reduced pressure to give a colourless gum which was purified by FCC (SiO$_2$, 0-100%

EtOAc in cyclohexane). Fractions containing the desired compound were combined and evaporated to give 3-methoxy-2-(3-methoxyphenyl)propanoic acid (88 mg, 33%). ¹H NMR (400 MHz, DMSO-d6, 30° C.) δ3.25 (s, 3H), 3.49 (1H, dd), 3.74 (3H, s), 3.88-3.76 (2H, m), 6.93-6.80 (3H, m), 7.32-7.17 (1H, m), 12.51 (1H, s). m/z: ES⁺ [M+H]⁺ 211.

Intermediate 30

Ethyl 3-methoxy-2-(3-methoxyphenyl)propanoate

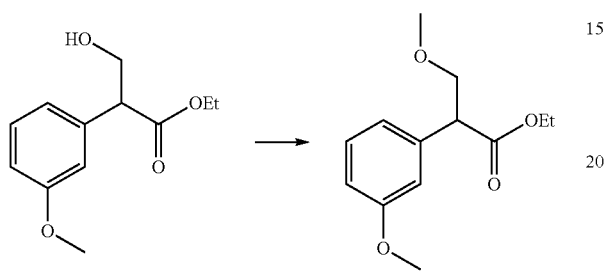

To a solution of ethyl 3-hydroxy-2-(3-methoxyphenyl) propanoate (Intermediate 31, 0.38 g, 1.695 mmol) in MeCN (2 mL) in a round bottomed flask was added silver oxide (0.5 g, 2.14 mmol). The solution was cooled to 0° C. and treated with iodomethane (0.17 mL, 2.676 mmol). The reaction mixture was allowed to stir at room temperature in the dark for 2.5 days. LCMS analysis showed some product but mainly starting material. A further 0.53 mL of iodomethane and 0.15 g of silver oxide were added and stirring was continued for 24 hours. The reaction had progressed further so it was left to stir for another 7 days. LCMS analysis showed complete conversion. The mixture was filtered through celite and the solvent was removed under reduced pressure. The residue was adsorbed onto silica and purified by FCC (SiO₂, 0-40% EtOAc in cyclohexane). The appropriate fractions were evaporated under reduced pressure to isolate ethyl 3-methoxy-2-(3-methoxyphenyl)propanoate as a colourless oil (0.3 g, 74%). ¹H NMR (400 MHz, CDCl₃, 21° C.) δ1.23 (3H, t), 3.37 (3H, s), 3.58 (1H, dd), 3.80 (3H, s), 3.84 (1H, dd), 3.97 (1H, t), 4.24-4.08 (2H, m), 6.82 (1H, ddd), 6.95-6.85 (2H, m), 7.23 (1H, d). m/z: ES⁺ [M+H]⁺ 239.

Intermediate 31

Ethyl 3-hydroxy-2-(3-methoxyphenyl)propanoate

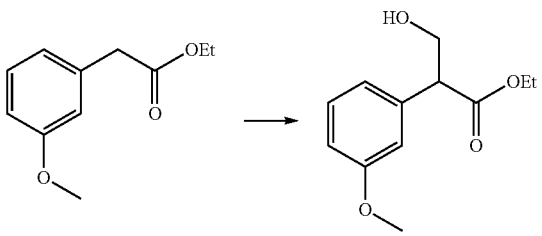 [SMILES: CCOC(=O)Cc1cccc(OC)c1 ; CCOC(=O)C(CO)c1cccc(OC)c1]

Ethyl 2-(3-methoxyphenyl)acetate (1.0 g, 5.149 mmol) was weighed into a round bottom flask with sodium hydrogen carbonate (0.02 g, 0.257 mmol). DMSO (8 mL) was added followed by paraformaldehyde (0.39 mL, 5.149 mmol). The resultant suspension was allowed to stir at room temperature for 24 hours then the reaction was heated at 60° C. for 3 hours to give a colourless solution. The reaction mixture was cooled, diluted with water (100 mL) and neutralised with 0.5 M HCl. The aqueous was extracted with EtOAc (3×50 mL), dried (MgSO₄) and evaporated under reduced pressure to give a colourless oil which was purified by FCC (SiO₂, 0-50% EtOAc in cyclohexane). The solvent was removed under reduced pressure to provide ethyl 3-hydroxy-2-(3-methoxyphenyl)propanoate as a colourless oil (0.38 g, 33%). ¹H NMR (400 MHz, CDCl₃, 21° C.) δ1.23 (3H, t), 2.26 (1H, s), 3.86-3.76 (5H, m), 4.28-4.06 (3H, m), 6.89-6.79 (3H, m), 7.30-7.22 (1H, m). m/z: ES⁺ [M+H]⁺ 225.

Intermediate 32

2-Methoxy-2-[3-(trifluoromethoxy)phenyl]acetic Acid

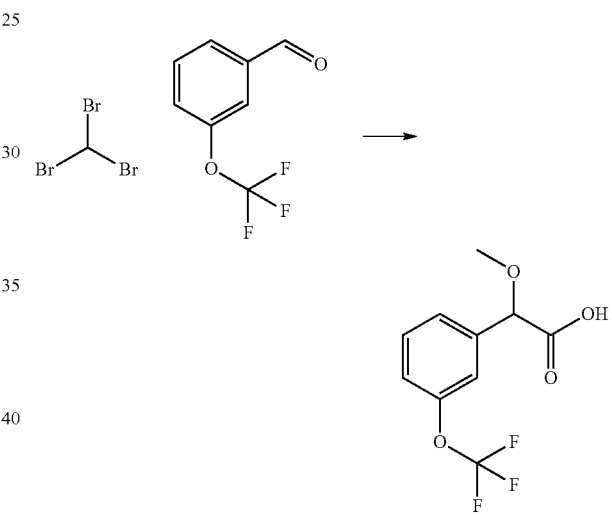

A solution of potassium hydroxide (1.851 g, 33.00 mmol) in MeOH (10 mL) was added over 2 h in small portions to a stirred mixture of 3-(trifluoromethoxy)benzaldehyde (1.141 g, 6 mmol) and bromoform (0.630 mL, 7.20 mmol) in MeOH (5.00 mL) at 0° C. The mixture was then allowed to warm to r.t. and left to stir overnight. A white precipitate formed in the reaction mixture. The solids were filtered off under reduced pressure rinsing the filter cake with MeOH (15 mL). The filtrate was evaporated to a thick white paste then re-dissolved in water (50 mL). This was then washed with Et₂O (50 mL). The aqueous phase was acidified to pH=2 (~5 mL 2M HCl solution) and then extracted into EtOAc (3×50 mL). The combined organics were dried (MgSO₄), filtered and evaporated under reduced pressure to give a clear oil. The crude product was purified by FCC (SiO₂, 10-50% EtOAc in heptanes). Pure fractions were evaporated to dryness to afford 2-methoxy-2-[3-(trifluoromethoxy)phenyl]acetic acid (0.832 g, 55%) as a colourless oil. ¹H NMR (400 MHz, CDCl₃, 30° C.) δ3.47 (3H, s), 4.81 (1H, s), 7.20-7.24 (1H, m), 7.33 (1H, s), 7.37-7.46 (2H, m). m/z: ES⁻ [M−H]⁻ 249.4.

Intermediate 33

2-(3,5-Dimethoxyphenyl)-2-ethoxy-acetic Acid

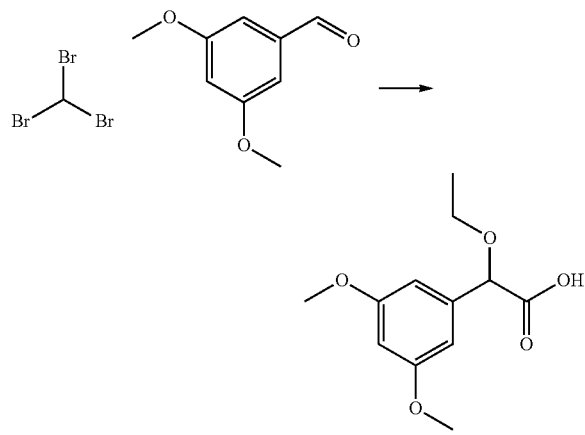

To a stirred mixture of 3,5-dimethoxybenzaldehyde (2.16 mL, 15.04 mmol) and bromoform (1.58 mL, 18.054 mmol) in ethanol (15 mL) at 0° C. was added, dropwise over 30 mins, a solution of potassium hydroxide (4.64 g, 82.747 mmol) in ethanol (30 mL). After completion of addition the mixture was left to stir and warmed to room temperature overnight. Next morning, the precipitate was removed by filtration. The filtrate was evaporated to give a paste which was taken up in water (75 mL) and extracted with EtOAc (2×75 mL). The aqueous phase was then acidified to pH=2 with 2N HCl. It was extracted with EtOAc (2×100 mL). The combined organics were dried (MgSO$_4$) and evaporated to give the crude product. Purification was by FCC (SiO$_2$, 0-5% MeOH in DCM). Pure fractions were combined and evaporated under reduced pressure to give 2-(3,5-dimethoxyphenyl)-2-ethoxy-acetic acid as an orange gum (2.46 g, 68%). $^1$H NMR (400 MHz, DMSO-d6, 25° C.) δ1.15 (3H, t), 3.37-3.42 (1H, m), 3.48-3.55 (1H, m), 3.73 (6H, s), 4.78 (1H, s), 6.29 (1H, s), 6.53 (1H, s), 6.54 (1H, s), 12.76 (1H, s). m/z: ES$^-$ [M−H]$^-$ 239.

Intermediate 34

2-[4-Fluoro-3-(3-methoxyazetidin-1-yl)phenyl]-2-methoxy-acetic Acid

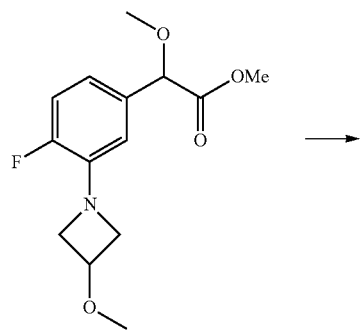

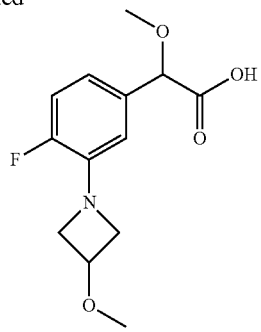

Methyl 2-[4-fluoro-3-(3-methoxyazetidin-1-yl)phenyl]-2-methoxy-acetate (Intermediate 35, 250 mg, 0.88 mmol) was suspended in water (1.5 mL), treated with lithium hydroxide (42 mg, 1.77 mmol) and heated at 40° C. for 2 h. The reaction mixture was allowed to cool to room temperature and the MeOH evaporated under reduced pressure. The aqueous phase was diluted with brine (5 mL) and adjusted to pH=5 by the addition of saturated aqueous citric acid. The aqueous was extracted with DCM containing 5% MeOH (3×10 mL). The combined organic extracts were dried (MgSO$_4$) and filtered. The aqueous was further acidified to pH=3 by the addition of formic acid then re-extracted with EtOAc (4×10 mL). The EtOAc extracts were combined, dried (MgSO$_4$), filtered, combined with the DCM/MeOH extracts then evaporated under reduced pressure. The gummy residue was concentrated twice from Et$_2$O to give 2-[4-fluoro-3-(3-methoxyazetidin-1-yl)phenyl]-2-methoxy-acetic acid (221 mg, 93%) as a pale yellow glassy solid. $^1$H NMR (400 MHz, CDCl$_3$, 21° C.) δ3.33 (3H, s), 3.41 (3H, s), 3.80-3.83 (2H, m), 4.19-4.23 (2H, m), 4.29-4.33 (1H, m), 4.68 (1H, s), 6.50 (1H, dd), 6.75 (1H, ddd), 6.94 (1H, dd). m/z: ES-[M+H]$^+$ 270.1.

Intermediate 35

Methyl 2-[4-fluoro-3-(3-methoxyazetidin-1-yl)phenyl]-2-methoxy-acetate

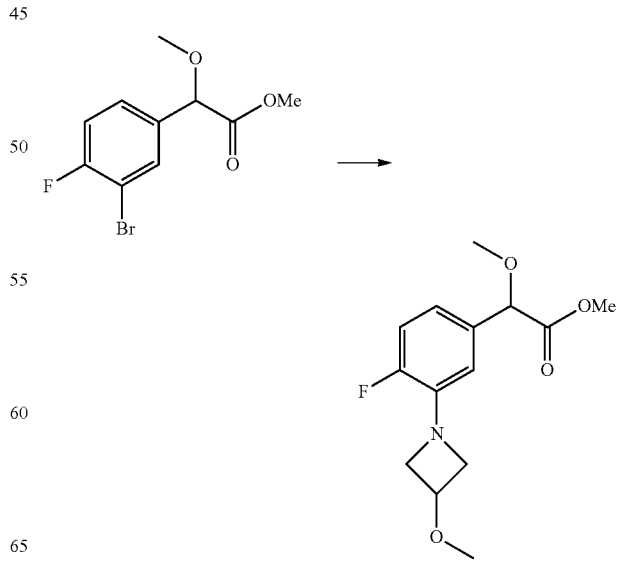

Methyl 2-(3-bromo-4-fluoro-phenyl)-2-methoxy-acetate (Intermediate 36, 600 mg, 2.17 mmol) was weighed into a 3 neck round bottomed flask fitted with a suba seal, $N_2$ inlet and reflux condenser. The flask was flushed with $N_2$ for 5 minutes then 3-methoxyazetidine hydrochloride (0.27 g, 2.17 mmol) and caesium carbonate (2.47 g, 7.58 mmol) were added. In a separate flask 2-dicyclohexylphosphino-2,6-di-iso-propoxybiphenyl, (Ruphos, 0.04 g, 0.087 mmol) and Ruphos Pd G2 (0.06 g, 0.077 mmol) were dissolved in dry toluene. The solution was degassed with $N_2$ for 5 minutes through a needle and then added to the other reagents in the 3 neck round bottom flask through the suba seal. The reaction mixture was heated at 90° C. for 20 h. The reaction mixture was allowed to cool to room temperature and diluted with EtOAc (20 mL) and water (20 mL). The organic layer was collected and the aqueous was washed with a further portion of EtOAc (20 mL). The organics were washed with brine (50 mL), separated and evaporated under reduced pressure. The residue was purified by FCC ($SiO_2$, 0-70% EtOAc in petroleum ether). Pure fractions were combined and evaporated under reduced pressure to give methyl 2-[4-fluoro-3-(3-methoxyazetidin-1-yl)phenyl]-2-methoxy-acetate (136 mg, 22%) as a colourless oil. $^1$H NMR (400 MHz, $CDCl_3$, 21° C.) δ3.33 (3H, s), 3.38 (3H, s), 3.72 (3H, s), 3.78-3.83 (2H, m), 4.19-4.23 (2H, m), 4.29-4.33 (1H, m), 4.67 (1H, s), 6.55 (1H, dd), 6.75 (1H, ddd), 6.92 (1H, dd). m/z: $ES^+$ $[M+H]^+$ 284.0.

Intermediate 36

Methyl 2-(3-bromo-4-fluoro-phenyl)-2-methoxy-acetate

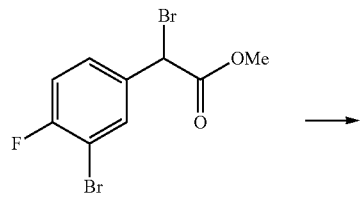

Sodium (93 mg, 4.05 mmol) was dissolved in MeOH (12 mL) under $N_2$. A solution of methyl 2-bromo-2-(3-bromo-4-fluoro-phenyl)acetate (Intermediate 37, 1.20 g, 3.68 mmol) in MeOH (3 mL) was added and the reaction mixture heated to 40° C. for 2 h. The reaction mixture was cooled to r.t. and evaporated under reduced pressure. The residue was treated with saturated $NH_4Cl$ (aq) (10 mL) and extracted with EtOAc (3×10 mL). The combined organic extracts were dried ($MgSO_4$), filtered and evaporated under reduced pressure. The residue was purified by FCC ($SiO_2$, 0-10% EtOAc in petroleum ether). Pure fractions were combined and evaporated under reduced pressure to give methyl 2-(3-bromo-4-fluoro-phenyl)-2-methoxy-acetate (616 mg, 60%) as a colourless oil. $^1$H NMR (400 MHz, $CDCl_3$, 21° C.) δ3.42 (3H, s), 3.74 (3H, s), 4.73 (1H, s), 7.12 (1H, t), 7.37 (1H, ddd), 7.67 (1H, dd).

Intermediate 37

Methyl 2-bromo-2-(3-bromo-4-fluoro-phenyl)acetate

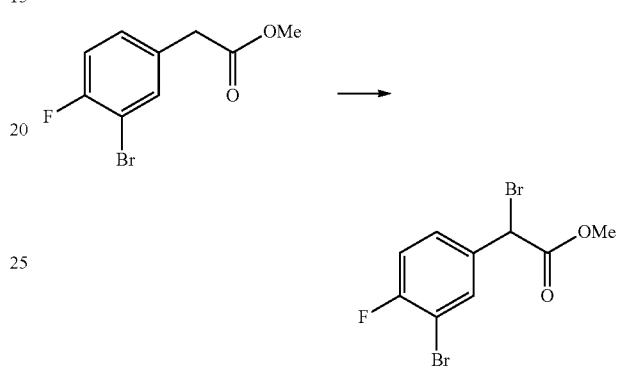

A solution of methyl 2-(3-bromo-4-fluoro-phenyl)acetate (5.0 g, 20.24 mmol) in carbon tetrachloride (50 mL) was prepared and N-bromosuccinimide (3.78 g, 21.25 mmol) was added followed by 2,2'-azobis(2-methylpropionitrile) (0.17 g, 1.01 mmol). The reaction was heated to reflux for 4 hours and allowed to cool to room temperature. The precipitate was filtered off and the solution was evaporated under reduced pressure. The crude residue was purified by FCC ($SiO_2$, 0-10% EtOAc in petroleum ether). Pure fractions were combined and evaporated under reduced pressure to give methyl 2-bromo-2-(3-bromo-4-fluoro-phenyl)acetate (5.30 g, 80%) as a colourless oil. $^1$H NMR (400 MHz, $CDCl_3$, 21° C.) δ3.81 (3H, s), 5.28 (1H, s), 7.12 (1H, t), 7.49 (1H, ddd), 7.78 (1H, dd).

Intermediate 38

Lithium 2-[4-fluoro-3-(3-fluoroazetidin-1-yl)phenyl]-2-methoxy-acetate

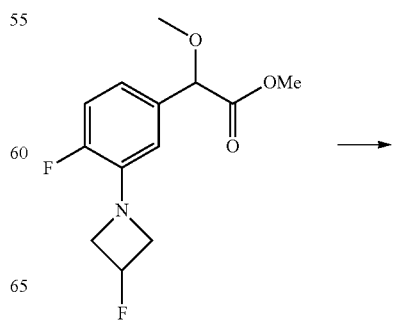

-continued

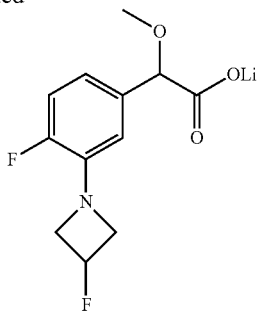

Lithium hydroxide (99.86 mg, 4.16 mmol) was suspended in water (10 mL) and methanol (33 mL), treated with methyl 2-[4-fluoro-3-(3-fluoroazetidin-1-yl)phenyl]-2-methoxy-acetate (Intermediate 39, 565 mg, 2.08 mmol) and heated at 45° C. under nitrogen for 2 hours. The reaction mixture was allowed to cool to room temperature and the MeOH and water were removed under reduced pressure before being dried in a vacuum oven for 1 day. This gave lithium 2-[4-fluoro-3-(3-fluoroazetidin-1-yl)phenyl]-2-methoxy-acetate (0.60 g, 75%). $^1$H NMR (400 MHz, DMSO-d6) δ 3.18 (3H, s), 3.95-3.50 (3H, m), 4.18-4.11 (1H, m), 4.21 (1H, s), 5.58-5.32 (1H, m), 6.60 (1H, dd), 6.77-6.70 (1H, m), 6.96-6.88 (1H, m). m/z: ES$^+$ [M+H]$^+$ 263.1.

Intermediate 39

Methyl 2-[4-fluoro-3-(3-fluoroazetidin-1-yl)phenyl]-2-methoxy-acetate

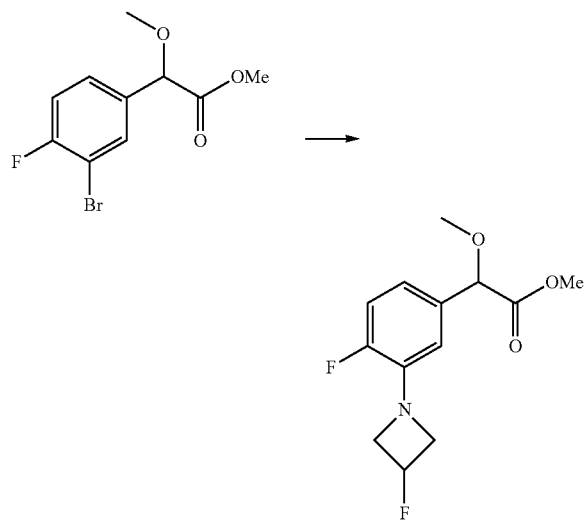

Into a 2 neck round bottomed flask fitted with a suba seal, magnetic stirrer bar nitrogen inlet and reflux condenser was added Ruphos Pd G1 methyl-t-butylether adduct (0.16 g, 0.193 mmol), 2-dicyclohexylphosphino-2,6-diisopropoxy-biphenyl, (Ruphos, 0.09 g, 0.193 mmol), 3-fluoroazetidine hydrochloride (0.5 g, 4.461 mmol) and caesium carbonate (4.24 g, 13.01 mmol) the flask was flushed with nitrogen gas for 5 minutes then in a separate round bottomed flask was placed methyl 2-(3-bromo-4-fluoro-phenyl)-2-methoxy-acetate (Intermediate 36, 1.03 g, 3.717 mmol). The flask was fitted with a suba seal and toluene (25 mL) was added under nitrogen. The resultant solution was degassed by bubbling nitrogen through it for 5 minutes then it was added under nitrogen to the 2 neck round bottomed flask containing the other reagents. The reaction mixture was heated at 90° C. for 48 hours and then allowed to cool to room temperature and evaporated under reduced pressure. The residue was partitioned between EtOAc (100 mL) and water (100 mL). The aqueous layer was extracted with a further portion of EtOAc (200 mL). The organics were combined, dried with MgSO4, filtered and evaporated under reduced pressure to yield a light brown oil which was dissolved in EtOAc and absorbed onto silica, then purified by flash column chromatography, eluting with 0-100% EtOAc in cyclohexane. Evaporation of the appropriate fractions provided methyl 2-[4-fluoro-3-(3-fluoroazetidin-1-yl)phenyl]-2-methoxy-acetate, (565 mg, 33%) as a pale yellow liquid. 1H NMR (400 MHz, DMSO-d6) δ 3.28 (3H, s), 3.63 (3H, s), 4.02-3.84 (2H, m), 4.31-4.17 (2H, m), 4.84 (1H, s), 5.57-5.31 (1H, m), 6.62-6.53 (1H, m), 6.79-6.71 (1H, m), 7.07 (1H, dd). m/z: ES$^+$ [M+H]$^+$ 271.2.

Intermediate 40

Lithium 2-[3-(3-fluoroazetidin-1-yl)-5-methoxy-phenyl]-2-methoxy-acetate

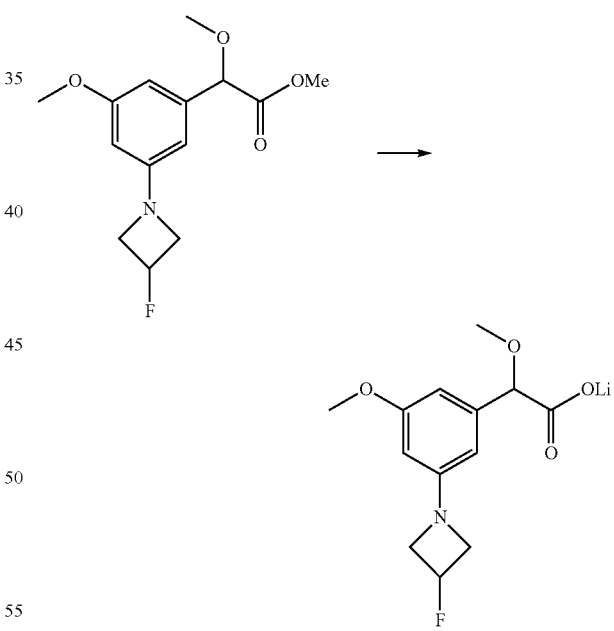

Lithium hydroxide (0.02 g, 0.932 mmol) was suspended in water (1 mL) and MeOH (3 mL) and treated with methyl 2-[3-(3-fluoroazetidin-1-yl)-5-methoxy-phenyl]-2-methoxy-acetate (Intermediate 41, 0.13 g, 0.466 mmol), The mixture was heated to 45° C. under N$_2$ for 2 h. It was then allowed to cool to r.t. and the solvents removed under reduced pressure before being dried in vacuo for 3 days to yield lithium 2-[3-(3-fluoroazetidin-1-yl)-5-methoxy-phenyl]-2-methoxy-acetate (137 mg, 101%). m/z: ES$^+$ [M+H]$^+$ 269.3.

Intermediate 41

Methyl 2-[3-(3-fluoroazetidin-1-yl)-5-methoxy-phenyl]-2-methoxy-acetate

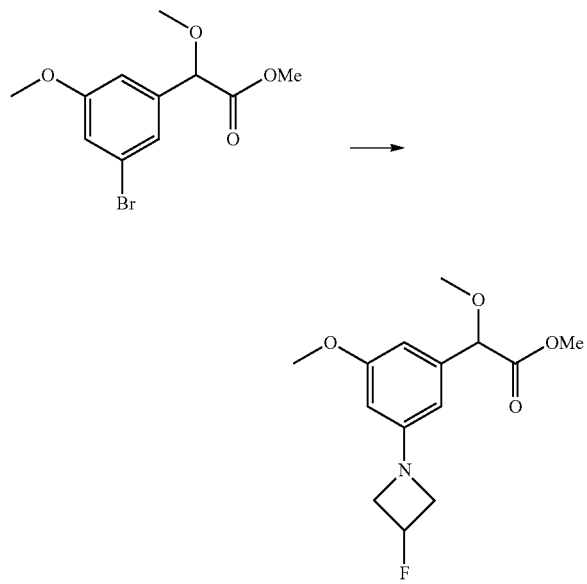

In a round bottomed flask was placed methyl 2-(3-bromo-5-methoxy-phenyl)-2-methoxy-acetate (Intermediate 42, 0.3 g, 1.038 mmol). The flask was fitted with a suba seal and toluene (6.5 mL) was added under $N_2$. The resultant solution was degassed by bubbling $N_2$ through for 5 minutes. Into a 2 neck round bottomed flask fitted with a suba seal, magnetic stirrer bar, nitrogen inlet and reflux condenser was added Ruphos Pd G1 methyl-t-butylether adduct (0.04 g, 0.054 mmol), 2-dicyclohexylphosphino-2,6-diisopropoxybiphenyl, (Ruphos, 0.03 g, 0.054 mmol), 3-fluoroazetidine hydrochloride (0.14 g, 1.245 mmol) and caesium carbonate (1.18 g, 3.632 mmol). The flask was flushed with $N_2$ for 5 min before addition of the degassed solution of methyl 2-(3-bromo-5-methoxy-phenyl)-2-methoxy-acetate (0.3 g, 1.038 mmol) in toluene through the suba seal. The reaction mixture was heated at 90° C. for 48 hours and then allowed to cool to room temperature and evaporated under reduced pressure. The residue was partitioned between EtOAc (100 mL) and water (100 mL). The aqueous layer was extracted with a further portion of EtOAc (200 mL). The organics were combined, dried ($MgSO_4$), filtered and evaporated to yield a light brown oil which was dissolved in EtOAc and absorbed onto silica. It was purified by FCC ($SiO_2$, 0-50% EtOAc in cyclohexane). Evaporation of the appropriate fractions provided methyl 2-[3-(3-fluoroazetidin-1-yl)-5-methoxy-phenyl]-2-methoxy-acetate (132 mg, 42%) as a pale yellow liquid. $^1$H NMR (400 MHz, DMSO-d6, 30° C.) δ3.27 (3H, s), 3.62 (3H, s), 3.71 (3H, s), 3.78-3.96 (2H, m), 4.05-4.21 (2H, m), 4.77 (1H, s), 5.35-5.57 (1H, m), 5.98 (1H, s), 6.05 (1H, s), 6.29 (1H, s). m/z: $ES^+$ $[M+H]^+$ 283.3.

Intermediate 42

Methyl 2-(3-bromo-5-methoxy-phenyl)-2-methoxy-acetate

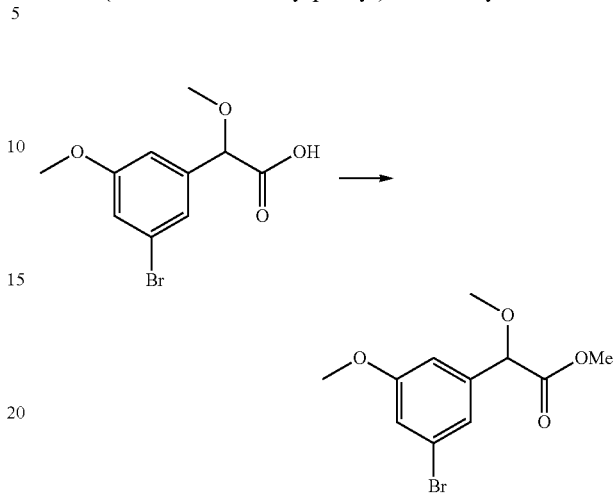

2-(3-Bromo-5-methoxy-phenyl)-2-methoxy-acetic acid (Intermediate 43, 2.77 g, 10.06 mmol) was dissolved in MeOH (30 mL), treated with concentrated sulfuric acid (0.17 mL, 2.014 mmol), and then heated to 65° C. for 2 h. The mixture was cooled to r.t. evaporated then diluted with water (5 mL) followed by saturated aqueous sodium bicarbonate (20 mL). The aqueous was extracted into DCM followed by EtOAc. The combined organics were evaporated and the crude material purified by FCC ($SiO_2$, 0-40% EtOAc in cyclohexane). Fractions containing the product were evaporated to give methyl 2-(3-bromo-5-methoxy-phenyl)-2-methoxy-acetate (1.2 g, 41%). (400 MHz, DMSO-d6, 30° C.) δ3.31 (s, 3H), 3.65 (3H, s), 3.78 (3H, s), 4.94 (1H, s), 6.90-6.95 (1H, m), 7.11-7.14 (1H, m), 7.15 (1H, dd). m/z: $ES^+$ $[M+H]^+$290.

Intermediate 43

2-(3-Bromo-5-methoxy-phenyl)-2-methoxy-acetic Acid

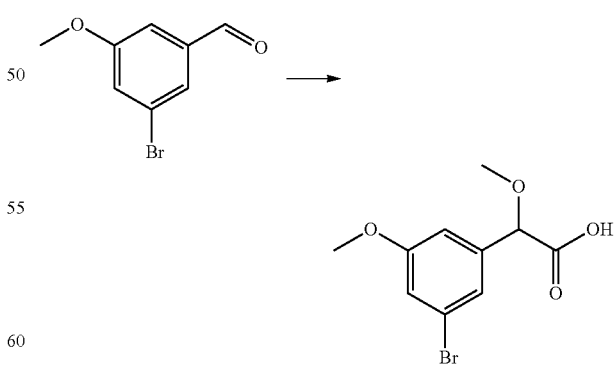

To a stirred mixture of potassium hydroxide (2.87 g, 51.15 mmol) and bromoform (0.98 mL, 11.16 mmol) in methanol (15 mL) at 0° C. was added, over a 10 mins period a suspension of 3-bromo-5-methoxy-benzaldehyde (0.75 mL, 9.301 mmol) in methanol (60 mL). After addition the mixture left to stir as it warmed to room temperature overnight. The reaction mixture was then treated with DCM (60 mL) and the precipitate was removed by filtration. The filtrate was evaporated to give a paste which was taken up in water (200 mL) and extracted with DCM (200 mL). The aqueous phase was then acidified to pH 2 with 2M HCl and extracted with DCM (2×100 mL) and EtOAc (2×100 mL). The combined organics were evaporated under reduced pressure and chromatographed (SiO$_2$, 0-30% EtOAc-cyclohexane). The fractions containing the product were evaporated to give 2-(3-bromo-5-methoxy-phenyl)-2-methoxy-acetic acid (0.84 g, 33%). $^1$H NMR (400 MHz, DMSO-d6) δ 3.30 (s, 3H) 3.77 (s, 3H), 4.78 (s, 1H), 6.94-6.91 (m, 1H), 7.14-7.10 (m, 2H), 13.04 (s, 1H). m/z: ES$^+$ [M+H]$^+$ 275.1.

Intermediate 44

2-Methoxy-2-[3-methoxy-5-(trifluoromethoxy)phenyl]acetic Acid

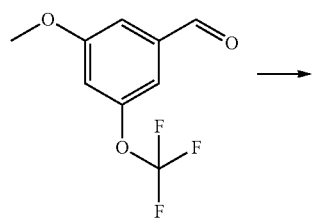

To a stirred mixture of 3-methoxy-5-(trifluoromethoxy)benzaldehyde (Intermediate 45, 0.15 g, 0.681 mmol) and bromoform (0.07 mL, 0.81 mmol) in MeOH (1 mL) at 0° C. was added, dropwise over 30 mins, a solution of potassium hydroxide (0.207 g, 3.75 mmol) in MeOH (2 mL). The mixture was stirred and warmed to r.t. overnight. The resulting precipitate was removed by filtration. The filtrate was evaporated to give a paste which was taken up in water (100 mL) and extracted with EtOAc (2×100 mL) to remove unreacted aldehyde. The aqueous phase was then acidified to pH=2 with 2N hydrochloric acid and extracted with EtOAc (2×100 mL). The combined organics were dried (MgSO$_4$), filtered and evaporated under reduced pressure to afford crude product which was purified by FCC (SiO$_2$, 0-10% MeOH in DCM) to give 2-methoxy-2-[3-methoxy-5-(trifluoromethoxy)phenyl]acetic acid (191 mg, 34%) as a yellow solid. m/z: ES$^+$ [M+H]$^+$ 280.

Intermediate 45

3-Methoxy-5-(trifluoromethoxy)benzaldehyde

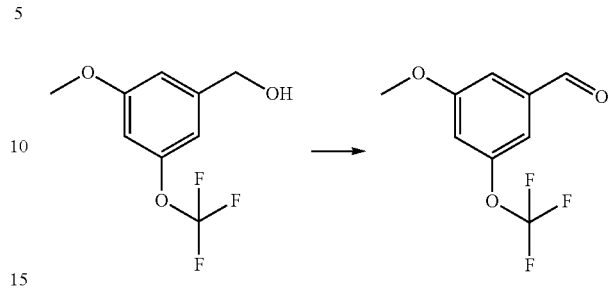

To a stirred solution of [3-methoxy-5-(trifluoromethoxy)phenyl]methanol (Intermediate 46, 330 mg, 1.49 mmol) in DCM (18 mL) was added activated manganese dioxide (646 mg, 7.43 mmol) and the reaction mixture was stirred at r.t. for 3 hours. The reaction mixture was diluted with water (50 mL), extracted with DCM (3×50 mL), washed with brine (100 mL), dried (MgSO$_4$), filtered and evaporated under reduced pressure to afford crude product which was purified by FCC (SiO$_2$, 0-50% EtOAc in cyclohexane) to give 3-methoxy-5-(trifluoromethoxy)benzaldehyde, (0.15 g, 45%) as a colourless oil. $^1$H NMR (400 MHz, DMSO-d6, 21° C.) δ3.83 (3H, s), 7.24-7.27 (1H, m), 7.39-7.42 (1H, m), 7.46-7.48 (1H, m), 9.94 (1H, s). m/z: ES$^+$ [M+H]$^+$ 222.

Intermediate 46

[3-Methoxy-5-(trifluoromethoxy)phenyl]methanol

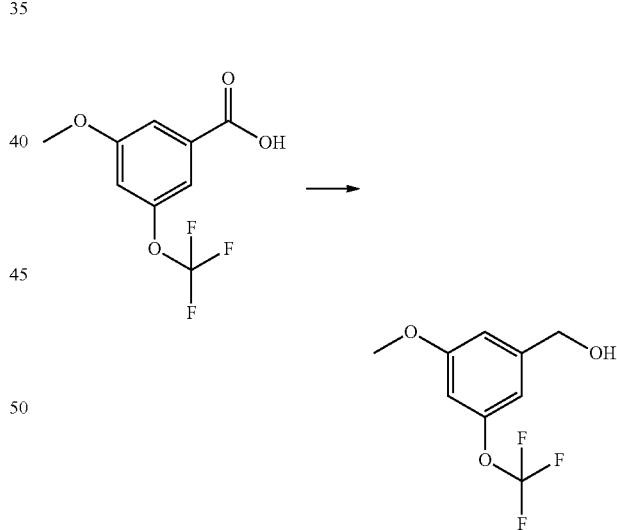

To a stirred solution of 3-methoxy-5-(trifluoromethoxy)benzoic acid (0.50 g, 2.12 mmol) in THF (10 mL) at 0° C. under nitrogen was added, dropwise over 10 mins, lithium aluminium hydride (1M in THF, 2.33 mL, 2.33 mmol). The reaction mixture was stirred and warmed to r.t. under nitrogen for 3 hours. The reaction mixture was diluted with water (10 mL), followed by of 2N NaOH (30 mL) solution and the salts formed were removed by filtration. The filtrate was extracted with DCM (3×100 mL), dried (MgSO$_4$), filtered and evaporated under reduced pressure to afford crude product which was purified by FCC (SiO$_2$, 0-50%

EtOAc in cyclohexane) to give [3-methoxy-5-(trifluoromethoxy)phenyl]methanol (0.33 g, 67%) as a white solid. m/z: ES+ [M+H]+ 222.

Intermediate 47

2-[3-(Difluoromethoxy)phenyl]-2-ethoxy-acetic Acid

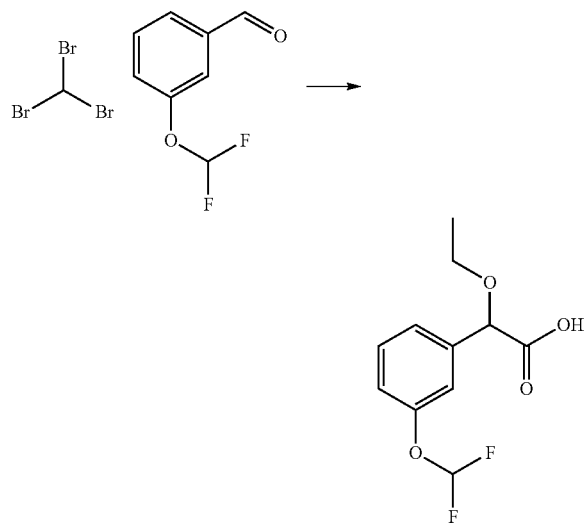

To a stirred mixture of 3-(difluoromethoxy)benzaldehyde (2.0 g, 11.619 mmol) and bromoform (1.22 mL, 13.94 mmol) in ethanol (40 mL) at 0° C. was added, dropwise over 1 hour, a solution of potassium hydroxide (3.59 g, 63.90 mmol) in ethanol (20 mL). After addition the mixture was left to stir and warmed to r.t. overnight. The precipitate was removed by filtration and the filtrate evaporated under reduced pressure to give a paste which was taken up in water (100 mL) and extracted with EtOAc (2×75 mL). The aqueous phase was then acidified to pH=1 with 2M HCl and extracted with EtOAc (2×75 mL). The combined organics were dried (MgSO$_4$), filtered and evaporated to give a pale brown oil which was purified by FCC (SiO$_2$, 95:5 cyclohexane: EtOAc+0.1% formic acid increasing to 8:2 EtOAc:cyclohexane+0.1% formic acid). Appropriate fractions were evaporated under reduced pressure to provide 2-[3-(difluoromethoxy)phenyl]-2-ethoxy-acetic acid as a colourless oil (1.8 g, 62%). $^1$H NMR (400 MHz, CDCl$_3$, 21° C.) δ1.29 (3H, t), 3.49-3.70 (2H, m), 4.89 (1H, s), 6.52 (1H, t), 7.07-7.15 (1H, m), 7.21-7.26 (1H, m), 7.28-7.35 (1H, m), 7.34-7.41 (1H, m). m/z: ES− [M−H]− 245.

Intermediate 48

2-Methoxy-2-[3-(oxetan-3-yl)phenyl]acetic Acid

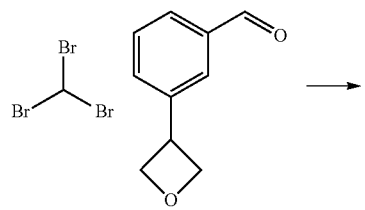

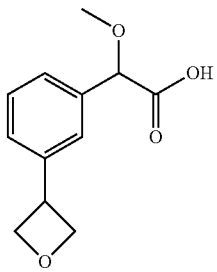

A solution of potassium hydroxide (1.427 g, 25.43 mmol) in MeOH (30 mL) was added over 2 hours in small portions to a stirred mixture of 3-(oxetan-3-yl)benzaldehyde (Intermediate 49, 750 mg, 4.62 mmol) and bromoform (0.485 mL, 5.55 mmol) in MeOH (15 mL) at 0° C. The mixture was then allowed to warm to room temperature and left to stir overnight. The solids were filtered under reduced pressure, rinsing the solids with MeOH (15 mL). The filtrate was evaporated to a thick white paste then re-dissolved in water (150 mL). This was washed with Et2O (200 mL) and then acidified to pH=2 with 2M. The aqueous phase was extracted into EtOAc (300 mL) and the combined organics were dried (MgSO$_4$), filtered and evaporated under reduced pressure to give 2-methoxy-2-[3-(oxetan-3-yl)phenyl]acetic acid as a colourless oil (1.0 g, 97%) which was used without further purification. $^1$H NMR (400 MHz, DMSO, 30° C.) δ 3.31 (3H, s), 4.18-4.35 (1H, m), 4.58 (2H, m), 4.77 (1H, s), 4.94 (1H, m), 7.22-7.57 (4H, m).

Intermediate 49

3-(Oxetan-3-yl)benzaldehyde

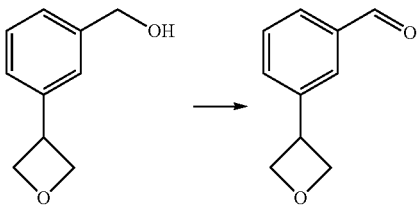 [SMILES: OCc1cccc(C2COC2)c1 ; O=Cc1cccc(C2COC2)c1]

Manganese (IV) oxide (14.30 g, 164.43 mmol) was added to (3-(oxetan-3-yl)phenyl)methanol (Intermediate 50, 1.5 g, 8.22 mmol) in DCM (70 mL) at 21° C. under nitrogen. The resulting mixture was stirred at 21° C. for 16 hours. The reaction was then filtered through celite, washed with DCM and evaporated to a gum. The crude product was purified by FCC (SiO$_2$, 10-60% EtOAc in heptanes). Pure fractions were evaporated to dryness to afford 3-(oxetan-3-yl)benzaldehyde (800 mg, 60%) as a colourless gum. $^1$H NMR (400 MHz, DMSO, 30° C.) δ4.21-4.51 (1H, m), 4.64 (2H, m), 4.98 (2H, m), 7.60 (1H, t), 7.74 (1H, d), 7.79-7.85 (1H, d), 7.94 (1H, s), 10.03 (1H, s).

Intermediate 50

(3-(Oxetan-3-yl)phenyl)methanol

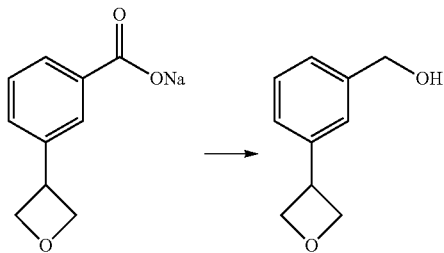

Lithium aluminium hydride (1M in THF, 1.94 mL, 1.95 mmol) was added dropwise to sodium 3-(oxetan-3-yl)benzoate (300 mg, 1.50 mmol) in THF (10 mL) at 0° C. under nitrogen. The resulting mixture was stirred at 0° C. for 20 minutes, then at 25° C. for 18 hours. 5% aqueous HCl was added and the mixture extracted with EtOAc (100 mL), washed with 2M aqueous $Na_2CO_3$ solution, before the organic layer was dried ($Na_2SO_4$), filtered and evaporated. The crude product was purified by FCC ($SiO_2$, 50-100% EtOAc in heptane followed by 10% 1M $NH_3$ in MeOH in EtOAc). Pure fractions were evaporated to dryness to afford (3-(oxetan-3-yl)phenyl)methanol (140 mg, 57%) as a colourless gum. $^1$H NMR (400 MHz, DMSO, 30° C.) δ 4.20 (1H, m), 4.51 (2H, d), 4.62 (2H, m), 4.95 (2H, m), 5.16 (1H, t), 7.17-7.29 (2H, m), 7.31-7.41 (2H, m).

Intermediate 51

2-Ethoxy-2-[3-(trifluoromethoxy)phenyl]acetic Acid

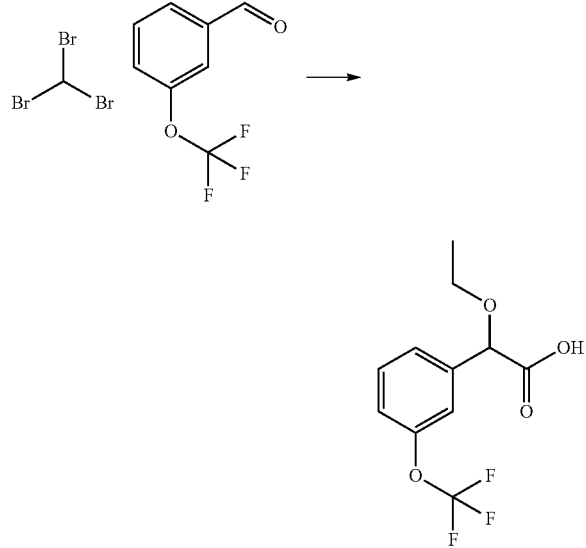

To a stirred mixture of potassium hydroxide (1.62 g, 28.93 mmol) and bromoform (0.55 mL, 6.31 mmol) in ethanol (15 mL) at 0° C. was added, slowly over a 10 min period, a solution of 3-(trifluoromethoxy)benzaldehyde (0.75 mL, 5.26 mmol) in ethanol (30 mL). After addition the mixture was left to stir and warmed to room temperature overnight. The precipitate was removed by filtration. The filtrate was evaporated to give a paste which was taken up in water (200 mL) and extracted with DCM (100 mL). This formed an emulsion, the aqueous phase was then acidified with 2M HCl (10 mL) and separated. It was then further extracted with EtOAc (100 mL). The combined organics were evaporated under reduced pressure and purified by FCC ($SiO_2$, 0-50% EtOAc in cyclohexane). Pure fractions were combined and evaporated under reduced pressure to give 2-ethoxy-2-[3-(trifluoromethoxy)phenyl]acetic acid (690 mg, 49%). $^1$H NMR (400 MHz, DMSO-d6, 21° C.) δ1.16 (3H, t), 3.38-3.50 (1H, m), 3.53-3.66 (1H, m), 4.99 (1H, s), 7.28-7.39 (2H, m), 7.45 (1H, d), 7.53 (1H, t), 13.04 (1H, s). m/z: $ES^+[M+H]^+$ 265.

Intermediate 52

2-[4-Fluoro-3-(trifluoromethoxy)phenyl]-2-methoxy-acetic Acid

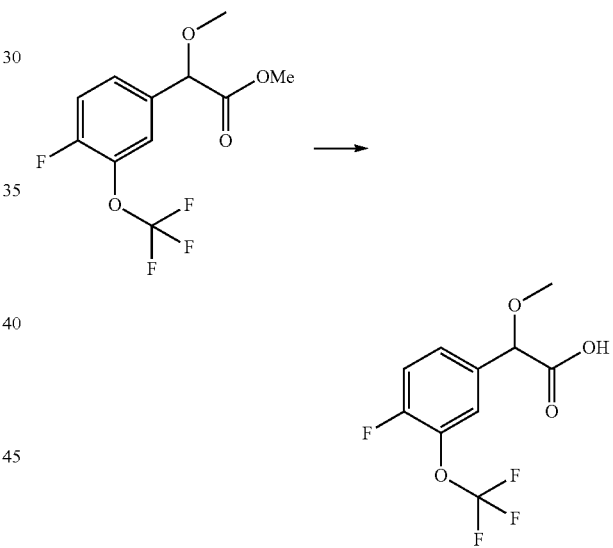

Lithium hydroxide (0.02 g, 0.9 mmol) was suspended in water (1 mL) and methanol (3 mL) and treated with ethyl 2-[4-fluoro-3-(trifluoromethoxy)phenyl]-2-methoxy-acetate (Intermediate 53, 0.13 g, 0.45 mmol) and heated at 45° C. for 2 hours. The reaction mixture was allowed to cool to room temperature and the MeOH removed under reduced pressure. The aqueous phase was diluted with brine (20 mL) and adjusted to pH 3 by the addition of formic acid then extracted with EtOAc (3×20 mL). The combined EtOAc extracts were washed with brine (30 mL) dried over $MgSO_4$, filtered and the solvent was removed under reduced pressure to yield 2-[4-fluoro-3-(trifluoromethoxy)phenyl]-2-methoxy-acetic acid (0.127 g, 105%). $^1$H NMR (400 MHz, $CDCl_3$-d6, 25° C.) δ3.47 (3H, s), 4.78 (1H, s), 7.23 (1H, dd), 7.37-7.46 (2H, m). m/z: ES+ $[M+H]^+$ 268.98.

Intermediate 53

Ethyl 2-[4-fluoro-3-(trifluoromethoxy)phenyl]-2-methoxy-acetate

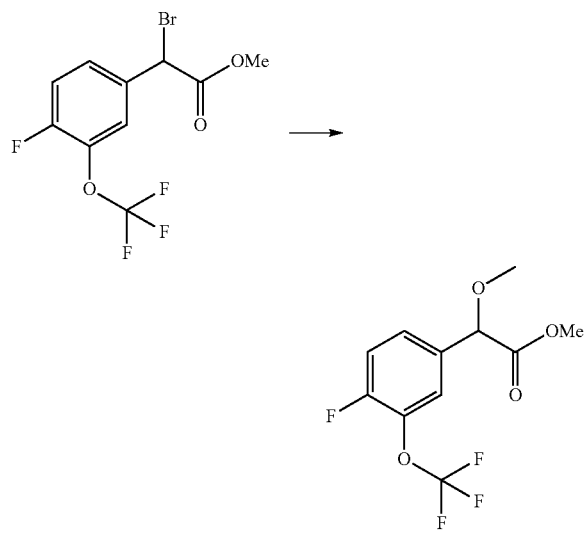

In a round bottomed flask under N$_2$ was added sodium (0.04 g, 1.66 mmol) to dry methanol (12 mL). To this solution was added methyl 2-bromo-2-[4-fluoro-3-(trifluoromethoxy)phenyl]acetate (Intermediate 54, 0.5 g, 1.51 mmol) in methanol (3 mL) under N$_2$. The reaction mixture was heated at 40° C. for 2 hours. The solvent was removed under reduced pressure and the remaining gum was partitioned between saturated ammonium chloride solution (50 mL) and EtOAc (50 mL). The aqueous layer was extracted with a further portion of EtOAc (50 mL). The organics were combined dried with MgSO$_4$, filtered and the solvent was removed under reduced pressure. The residual oil was purified by flash column chromatography eluting with 100% cyclohexane to 15% EtOAc in cyclohexane. Evaporation of the appropriate fractions provided ethyl 2-[4-fluoro-3-(trifluoromethoxy)phenyl]-2-methoxy-acetate (0.127 g, 28%).
$^1$H NMR (400 MHz, CDCl$_3$-d6, 25° C.) δ1.23 (3H, t), 3.44 (3H, s), 4.12-4.28 (2H, m), 4.74 (1H, d), 7.20 (1H, dd), 7.39 (1H, dddd), 7.42-7.48 (m, 1H).

Intermediate 54

Methyl 2-bromo-2-[4-fluoro-3-(trifluoromethoxy)phenyl]acetate

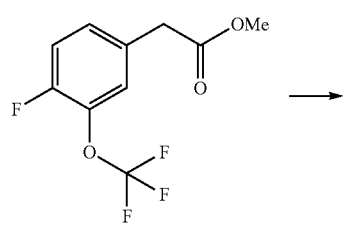

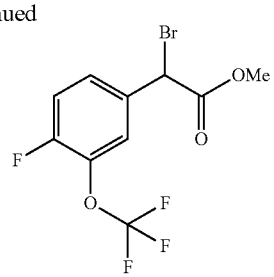

Methyl 2-[4-fluoro-3-(trifluoromethoxy)phenyl]acetate (Intermediate 55, 0.65 g, 2.578 mmol) and N-bromosuccinimide (4.08 g, 22.919 mmol) were weighed into a round bottomed flask and 2,2-azobis(2-methylpropionitrile), (AIBN, 0.02 g, 0.129 mmol) in carbon tetrachloride (6 mL) were added. The reaction was heated to reflux for 4 hours and allowed to cool to room temperature. The precipitate was filtered off and the solution was treated with silica and evaporated under reduced pressure and was purified by flash column chromatography eluting with 100% cyclohexane gradually increasing to 30% EtOAc in cyclohexane. Appropriate fractions were evaporated under reduced pressure to yield methyl 2-bromo-2-[4-fluoro-3-(trifluoromethoxy)phenyl]acetate as a pale yellow oil (1.1 g, 129%).
$^1$H NMR (400 MHz, CDCl$_3$-d6, 25° C.) δ3.81 (3H, s), 5.29 (1H, s), 7.17-7.24 (1H, m), 7.46-7.52 (1H, m), 7.53-7.59 (1H, m).

Intermediate 55

Methyl 2-[4-fluoro-3-(trifluoromethoxy)phenyl]acetate

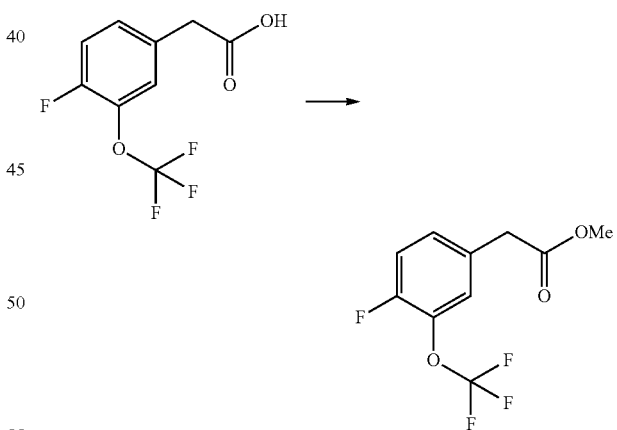

4-Fluoro-3-(trifluoromethoxy)phenylacetic acid (1.0 g, 4.199 mmol) was suspended in methanol (10 mL) and treated with sulfuric acid (0.07 mL, 0.84 mmol) and heated at 45° C. for 2 hours. The reaction mixture was allowed to cool to room temperature and the methanol removed under reduced pressure. The residue was diluted with brine (20 mL) and then extracted with EtOAc (3×20 mL). The combined EtOAc extracts were washed with brine (30 mL) dried over MgSO$_4$, filtered and the solvent was removed under reduced pressure to yield methyl 2-[4-fluoro-3-(trifluoromethoxy)phenyl]acetate, (0.65 g, 61%)

¹H NMR (400 MHz, DMSO-d6) δ 3.63 (3H, s), 3.78 (2H, s), 7.33-7.39 (1H, m), 7.42-7.53 (2H, m). m/z: ES⁺ [M+H]⁺ 253.

Biological Assays

The following assays were used to measure the effects of the compounds described herein: a) GLS Enzyme Potency Assay; b) GLS Cell Potency Assay; c) GLS Cell Proliferation Assay. During the description of the assays, generally:
  i. The following abbreviations have been used: $CO_2$=Carbon dioxide; DMEM=Dulbecco's Modified Eagle Medium; DMSO=Dimethyl sulphoxide; EDTA=Ethylenediaminetetraacetic acid; EGTA=Ethylene glycol tetraacetic acid; FCS=Foetal calf serum; h=Hour(s); NBS=Non-binding surface; SDS=Sodium dodecyl sulphate; TRIS=Tris(Hydroxymethyl)aminomethane.
  ii. $IC_{50}$ values were calculated using a smart fitting model in Genedata. The $IC_{50}$ value was the concentration of test compound that inhibited 50% of biological activity.

Assay a): GLS Enzyme Potency Assay

A Glutamate Oxidase/AmplexRed coupled assay was used to measure the ability of compounds to bind to and inhibit the activity of GLS1 in vitro. 6His tagged GLS protein (amino acids 63-669) expressed in *E. Coli* was purified and stored at −80° C. in aliquots. GLS1 was diluted to 2× working concentration and incubated at room temperature to allow the tetrameric/dimeric forms to reach steady state. Assay measurements were performed in buffer comprising 50 mM TRIS pH 7.8, 100 mM $NaPO_4$, pH 7.8, 0.001% v/v Tween20. Purified recombinant GLS1 protein was diluted in assay buffer to 12 nM and pre-incubated at room temperature for 30 minutes. Test compounds were prepared by dilution in 100% DMSO to give the correct dose range for 12 point concentration response and an appropriate volume (2.5-60 nl) dispensed into 384 well micro assay plates (Greiner product code 784900) using a Labcyte Echo 555 acoustic dispenser. DMSO concentration was maintained at 2% by back filling with DMSO solution. 3 μL of diluted GLS1 protein (12 nM) was then dispensed into each well using a BioRaptr automated dispenser (Beckman-Coulter) and incubated for 15 minutes at room temperature. 3 μL of 100 mM glutamine diluted in assay buffer was then added and the reaction incubated at room temperature for 60 minutes. The reaction was then stopped by addition of 45 μM 6-(2-bromoethynyl)-2,3-dimethyl-quinazolin-4-one, 75 μM Amplex Red, 0.375 units/mL Horseradish Peroxidase, 0.12 units/mL Glutamate Oxidase in 100 mM TRIS pH7.5. After 30 minutes at room temp in the dark, plates were read on a Perkin Elmer EnVision using 535/590 nm optic filters and raw data analysed using Genedata to generate $IC_{50}$ values. An artefact version of the assay where the 6His tagged GLS protein and glutamine were replaced with assay buffer was also used to rule out non specific effects on the assay components.

Assay b): GLS Cell Potency Assay

Compounds were assessed for their potential to inhibit cellular GLS activity by use of a PC3 coupled assay measuring cellular glutamate depletion. Test compounds were prepared by dilution in 100% DMSO to give the correct dose range for 12 point concentration response and an appropriate volume (5-120 nl) dispensed into 384 well micro assay plates (Corning product code 3712) using a Labcyte Echo 555 acoustic dispenser. DMSO concentration was maintained at 0.3% by back filling with DMSO solution. PC3 cells were grown in phenol free DMEM, 10% dialyzed FCS, 2 mM glutamine and following dispersal by trypsinisation were plated at 5.6×10³ cells per well in 40 μl of growth medium directly into the 384 well assay plates containing dispensed compound. After incubation for 6 h at 37° C., 5% $CO_2$ growth media was aspirated and cells lysed in 15 μl of buffer containing 10 mM TRIS pH7.4, 100 mM NaCl, 1 mM EDTA, 1 mM EGTA, 1 mM NaF, 20 mM $Na_4P_2O_7$, 2 mM $Na_3VO_4$, 1% Triton X-100, 10% glycerol, 0.1% SDS and 0.5% deoxycholate. 4 μl Of cell lysate was then transferred to a 384 well NBS plate (Corning product code 3575) and 35 μl of 27.5 μM Amplex Red, 0.1375 U/mL Horseradish Peroxidase, 0.044 U/mL glutamate oxidase, 100 mM TRIS pH7.5 was added. After 30 minutes at room temp in the dark, plates were read on a Perkin Elmer EnVision using 535/590 nm optic filters and raw data analysed using proprietary software to generate $IC_{50}$ values.

Assay c): GLS Cell Proliferation Assay

The ability of compounds to inhibit cell growth was measured using a 384 well plate NCI-H1703 cell proliferation assay. NCI-H1703 cells were grown in phenol red free RPMI1640, 10% FCS and 2 mM glutamine and seeded at a density of 750 cells per well in 40 μl of growth medium into clear-bottom 384 well assay plates (Corning product code 3712) and incubated for 24 h at 37° C., 5% $CO_2$. Test compounds were prepared by dilution in 100% DMSO to give the correct dose range for 12 point concentration response and an appropriate volume (5-120 nl) dispensed directly into the assay plates containing plated cells. DMSO concentration was maintained at 0.3% by back filling with DMSO solution. Plates were incubated for 5 days at 37° C., 5% $CO_2$, Sytox Green and Saponin added to final concentration of 2 μM and 0.25% respectively and incubated for 6 h prior to analysis. Plates were read on an Acumen eX3 (TTP Labtech) using 488 nm excitation and FITC filter set (500-530 nm) for emission. $IC_{50}$ values were calculated by curve fitting to max inhibition of day zero growth using GeneData software analysis.

Results from assays a)-c) are shown in Table 1.

TABLE 1

| | Assay data | | |
|---|---|---|---|
| Example | Assay a) enz $IC_{50}$ μM | Assay b) GLS cell MOA Mean $IC_{50}$ μM | Assay c) Prolif Mean $IC_{50}$ μM |
| 1(a) | 0.0206 | 0.00083 | 0.00255 |
| 1(b) | 0.0726 | 0.0184 | 0.133 |
| 2(a) | 0.0872 | 0.000245 | 0.0025 |
| 2(b) | 0.121 | 0.00411 | 0.0286 |
| 3(a) | 0.0308 | 0.000823 | 0.00265 |
| 3(b) | 0.0721 | 0.014 | 0.272 |
| 4(a) | 0.0423 | 0.000809 | 0.00295 |
| 4(b) | 0.0596 | 0.00608 | 0.0273 |
| 5(a) | 0.0288 | 0.00122 | 0.0117 |
| 5(b) | 0.13 | 0.0181 | 0.12 |
| 6(a) | 0.028 | 0.000659 | 0.0022 |
| 6(b) | 0.213 | 0.0226 | 0.0659 |
| 7(a) | — | — | 0.00164 |
| 7(b) | 0.192 | 0.0485 | 0.151 |
| 8(a) | 0.0649 | 0.000664 | 0.0576 |
| 8(b) | 0.19 | 0.0326 | 0.0385 |
| 9(a) | 0.0591 | 0.00102 | 0.0049 |
| 9(b) | 0.519 | 0.0364 | 0.122 |
| 10(a) | 0.0349 | — | — |
| 10(b) | 0.0722 | 0.00787 | 0.0434 |
| 11(a) | 0.00635 | 0.000229 | 0.0017 |
| 11(b) | 0.00611 | 0.000309 | 0.00104 |
| 12(a) | 0.0438 | 0.00193 | 0.0329 |
| 12(b) | 0.971 | 0.0836 | 0.524 |
| 13(a) | 0.0751 | 0.00273 | 0.0142 |
| 13(b) | 1.42 | 0.0499 | 0.497 |
| 14(a) | 0.0915 | 0.000872 | 0.00589 |
| 14(b) | 0.66 | 0.0146 | 0.156 |

TABLE 1-continued

Assay data

| Example | Assay a) enz IC$_{50}$ μM | Assay b) GLS cell MOA Mean IC$_{50}$ μM | Assay c) Prolif Mean IC$_{50}$ μM |
| --- | --- | --- | --- |
| 15(a) | 0.0776 | 0.00174 | 0.0116 |
| 15(b) | 1.31 | 0.0757 | 0.376 |
| 16(a) | 0.0252 | 0.000664 | 0.00349 |
| 16(b) | 0.689 | 0.0384 | — |
| 17(a) | 0.0504 | — | 0.00156 |
| 17(b) | 0.157 | 0.00711 | 0.0349 |
| 18(a) | 0.0226 | 0.00213 | 0.0135 |
| 18(b) | 0.129 | 0.0546 | 0.699 |
| 19(a) | 0.0401 | 0.000473 | 0.00261 |
| 19(b) | 0.0961 | 0.00307 | 0.00759 |
| 20(a) | 0.0693 | 0.00207 | 0.00657 |
| 20(b) | 0.0641 | 0.000841 | 0.00265 |
| 21(a) | 0.02 | 0.000292 | 0.00224 |
| 21(b) | 0.0482 | 0.00885 | 0.0591 |
| 22(a) | 0.0685 | — | 0.00535 |
| 22(b) | 0.131 | 0.0106 | 0.178 |
| 23 | 0.0482 | 0.00885 | 0.0591 |
| 24 | 0.0526 | 0.00348 | 0.0291 |
| 25 | 1.84 | 0.0861 | 0.831 |
| 26 | 0.0235 | 0.000334 | 0.0042 |
| 27 | 0.149 | 0.0014 | 0.0135 |
| 28 | 0.195 | 0.0515 | 0.262 |
| 29 | 0.0511 | 0.000404 | 0.00196 |
| 30 | 1.37 | 0.00322 | 0.0377 |
| 31 | 0.0968 | 0.000573 | 0.00321 |
| 32 | 0.188 | 0.0146 | 0.0987 |
| 33 | 0.0685 | — | 0.00535 |
| 34 | 0.131 | 0.0106 | 0.018 |
| 35 | 0.077 | 0.00121 | 0.00903 |
| 36 | 0.612 | 0.0218 | 0.394 |
| 37 | 0.147 | 0.000556 | 0.0211 |
| 38 | 0.19 | — | 0.303 |
| 39 | 0.13 | 0.000405 | 0.00594 |
| 40 | 0.311 | — | 0.0825 |
| 41 | 0.0467 | 0.000468 | 0.00146 |
| 42 | 0.206 | — | 0.0815 |
| 43 | 0.02 | 0.000292 | 0.00224 |
| 44 | 0.0482 | 0.00885 | 0.0591 |
| 45(a) | 1.60 | 0.147 | 2.27 |
| 45(b) | 0.146 | 0.0113 | 0.00922 |

The invention claimed is:

1. A compound of Formula (I):

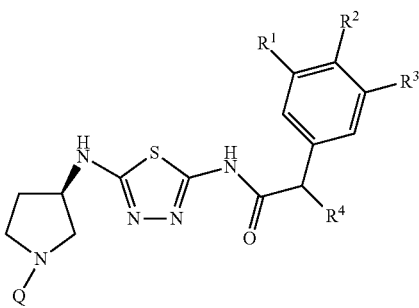

or a pharmaceutically acceptable salt thereof, wherein:
Q is 1,2,4-triazin-3-yl, pyridazin-3-yl, 6-methylpyridazin-3-yl, or 6-fluoropyridazin-3-yl;
$R^1$ is hydrogen, methoxy, trifluoromethoxy, oxetan-3-yl, 3-fluoroazetidin-1-yl, 3-methoxyazetidin-1-yl, or 3,3-difluoroazetidin-1-yl;
$R^2$ is hydrogen or fluoro;
$R^3$ is hydrogen or methoxy; and
$R^4$ is methoxy, ethoxy, or methoxymethyl;

provided that when $R^1$ is hydrogen, methoxy or trifluoromethoxy, then $R^3$ is not hydrogen, and/or $R^4$ is methoxymethyl.

2. The compound of claim 1, or a pharmaceutically acceptable salt thereof, wherein $R^1$ is methoxy and $R^3$ is methoxy.

3. The compound of claim 1, or a pharmaceutically acceptable salt thereof, wherein $R^1$ is oxetan-3-yl, 3-fluoroazetidin-1-yl; 3-methoxyazetidin-1-yl, or 3,3-difluoroazetidin-1-yl.

4. The compound of claim 1, or a pharmaceutically acceptable salt thereof, wherein $R^2$ is H.

5. The compound of claim 1, or a pharmaceutically acceptable salt thereof, wherein $R^3$ is methoxy.

6. The compound of claim 1, or a pharmaceutically acceptable salt thereof, wherein $R^4$ is methoxy.

7. The compound of claim 1, or a pharmaceutically acceptable salt thereof, wherein Q is 1,2,4-triazin-3-yl, or pyridazin-3-yl.

8. The compound of claim 1, or a pharmaceutically acceptable salt thereof, wherein the compound is selected from the group consisting of:

(2S)-2-[3-(3-fluoroazetidin-1-yl)phenyl]-2-methoxy-N-[5-[[(3R)-1-pyridazin-3-ylpyrrolidin-3-yl]amino]-1,3,4-thiadiazol-2-yl]acetamide;

(2S)-2-(3,5-dimethoxyphenyl)-2-methoxy-N-[5-[[(3R)-1-(6-methylpyridazin-3-yl)pyrrolidin-3-yl]amino]-1,3,4-thiadiazol-2-yl]acetamide;

(2S)-2-[3-(3,3-difluoroazetidin-1-yl)phenyl]-2-methoxy-N-[5-[[(3R)-1-pyridazin-3-ylpyrrolidin-3-yl]amino]-1,3,4-thiadiazol-2-yl]acetamide;

(2S)-2-methoxy-2-[3-(3-methoxyazetidin-1-yl)phenyl]-N-[5-[[(3R)-1-pyridazin-3-ylpyrrolidin-3-yl]amino]-1,3,4-thiadiazol-2-yl]acetamide;

(2S)-2-(3,5-dimethoxyphenyl)-2-methoxy-N-[5-[[(3R)-1-(1,2,4-triazin-3-yl)pyrrolidin-3-yl]amino]-1,3,4-thiadiazol-2-yl]acetamide;

(2R)-3-methoxy-2-(3-methoxyphenyl)-N-[5-[[(3R)-1-pyridazin-3-ylpyrrolidin-3-yl]amino]-1,3,4-thiadiazol-2-yl]propanamide;

(2S)-2-(3,5-dimethoxyphenyl)-2-ethoxy-N-[5-[[(3R)-1-pyridazin-3-ylpyrrolidin-3-yl]amino]-1,3,4-thiadiazol-2-yl]acetamide;

(2S)-2-[4-fluoro-3-(3-methoxyazetidin-1-yl)phenyl]-2-methoxy-N-[5-[(3R)-3-(pyridazin-3-ylamino)pyrrolidin-1-yl]-1,3,4-thiadiazol-2-yl]acetamide;

(2S)—N-[5-[[(3R)-1-(6-fluoropyridazin-3-yl)pyrrolidin-3-yl]amino]-1,3,4-thiadiazol-2-yl]-2-methoxy-2-[3-(3-methoxyazetidin-1-yl)phenyl]acetamide;

(2S)-2-[3-(3-fluoroazetidin-1-yl)-5-methoxy-phenyl]-2-methoxy-N-[5-[[(3R)-1-pyridazin-3-ylpyrrolidin-3-yl]amino]-1,3,4-thiadiazol-2-yl]acetamide;

(2S)-2-methoxy-2-[3-methoxy-5-(trifluoromethoxy)phenyl]-N-[5-[[(3R)-1-pyridazin-3-ylpyrrolidin-3-yl]amino]-1,3,4-thiadiazol-2-yl]acetamide;

(2R)-2-methoxy-2-[3-methoxy-5-(trifluoromethoxy)phenyl]-N-[5-[[(3R)-1-pyridazin-3-ylpyrrolidin-3-yl]amino]-1,3,4-thiadiazol-2-yl]acetamide;

(2S)-2-(4-fluorophenyl)-2-methoxy-N-[5-[[(3R)-1-(5-methylpyridazin-3-yl)pyrrolidin-3-yl]amino]-1,3,4-thiadiazol-2-yl]acetamide;

(2S)-2-methoxy-2-[3-(3-methoxyazetidin-1-yl)phenyl]-N-[5-[[(3R)-1-(6-methylpyridazin-3-yl)pyrrolidin-3-yl]amino]-1,3,4-thiadiazol-2-yl]acetamide;

(2S)-2-[4-fluoro-3-(3-fluoroazetidin-1-yl)phenyl]-2-methoxy-N-[5-[[(3R)-1-pyridazin-3-ylpyrrolidin-3-yl]amino]-1,3,4-thiadiazol-2-yl]acetamide;

(2S)-2-[3-(3,3-difluoroazetidin-1-yl)phenyl]-2-methoxy-N-[5-[[(3R)-1-(1,2,4-triazin-3-yl)pyrrolidin-3-yl]amino]-1,3,4-thiadiazol-2-yl]acetamide;

(2S)-2-methoxy-2-[3-(3-methoxyazetidin-1-yl)phenyl]-N-[5-[[(3R)-1-(1,2,4-triazin-3-yl)pyrrolidin-3-yl]amino]-1,3,4-thiadiazol-2-yl]acetamide;

(2S)-2-[3-(3-fluoroazetidin-1-yl)phenyl]-2-methoxy-N-[5-[[(3R)-1-(1,2,4-triazin-3-yl)pyrrolidin-3-yl]amino]-1,3,4-thiadiazol-2-yl]acetamide; and (2S)-2-methoxy-2-[3-(oxetan-3-yl)phenyl]-N-[5-[[(3R)-1-pyridazin-3-ylpyrrolidin-3-yl]amino]-1,3,4-thiadiazol-2-yl]acetamide.

9. A pharmaceutical composition comprising the compound of claim 1, or a pharmaceutically acceptable salt thereof, and at least one pharmaceutically acceptable diluent or carrier.

* * * * *